(12) United States Patent
Clinton

(10) Patent No.: US 7,396,810 B1
(45) Date of Patent: Jul. 8, 2008

(54) COMPOSITIONS AND METHODS FOR TREATING CANCER BY MODULATING HER-2 AND EGF RECEPTORS

(75) Inventor: Gail M. Clinton, Portland, OR (US)

(73) Assignee: Oregon Health Sciences University, Portland, OR (US)

(*) Notice: Subject to any disclaimer, the term of this patent is extended or adjusted under 35 U.S.C. 154(b) by 382 days.

(21) Appl. No.: 09/638,834

(22) Filed: Aug. 14, 2000

(51) Int. Cl.
*A61K 38/17* (2006.01)
*A61K 39/395* (2006.01)
*C07K 14/705* (2006.01)
*C07K 14/435* (2006.01)

(52) U.S. Cl. .................. 514/2; 424/130.1; 530/300; 530/350

(58) Field of Classification Search .................. 514/2; 424/130.1; 530/300, 350
See application file for complete search history.

(56) References Cited

U.S. PATENT DOCUMENTS

| | | | |
|---|---|---|---|
| 4,376,110 A | 3/1983 | David et al. | |
| 4,933,294 A | 6/1990 | Waterfield et al. | |
| 4,946,778 A | 8/1990 | Ladner et al. | |
| 5,401,638 A | 3/1995 | Carney et al. | 435/7.23 |
| 5,464,751 A | 11/1995 | Greene et al. | |
| 5,514,554 A | 5/1996 | Bacus | |
| 5,571,894 A | 11/1996 | Wels et al. | |
| 5,578,482 A | 11/1996 | Lippman et al. | |
| 5,604,107 A | 2/1997 | Carney et al. | 435/7.23 |
| 5,677,171 A | 10/1997 | Hudziak et al. | |
| 5,705,157 A * | 1/1998 | Greene | |
| 5,720,937 A | 2/1998 | Hudziak et al. | 424/9.34 |
| 5,747,261 A | 5/1998 | King et al. | |
| 5,756,456 A | 5/1998 | Ho et al. | |
| 5,763,213 A | 6/1998 | Ho et al. | |
| 5,783,186 A | 7/1998 | Arakawa et al. | 424/143.1 |
| 5,811,098 A | 9/1998 | Plowman et al. | |
| 5,837,523 A | 11/1998 | Greene et al. | |
| 5,861,301 A | 1/1999 | Terman et al. | |
| 5,874,528 A | 2/1999 | Lupu et al. | |
| 5,876,712 A | 3/1999 | Cheever et al. | |
| 5,910,583 A | 6/1999 | Marks et al. | |
| 5,919,764 A | 7/1999 | Greene et al. | |
| 5,985,553 A | 11/1999 | King et al. | |
| 6,015,567 A | 1/2000 | Hudziak et al. | 424/277.1 |
| 6,020,306 A | 2/2000 | Boyd et al. | |
| 6,045,797 A | 4/2000 | Margolis et al. | |
| 6,054,561 A | 4/2000 | Ring | |
| 6,166,082 A | 12/2000 | Kluender et al. | |
| 6,174,889 B1 | 1/2001 | Cockerill et al. | |
| 6,204,011 B1 | 3/2001 | Kendall et al. | |
| 6,267,958 B1 | 7/2001 | Andya et al. | |
| 6,333,169 B1 | 12/2001 | Hudziak et al. | |
| 6,359,115 B1 | 3/2002 | Kendall et al. | |
| 6,375,929 B1 | 4/2002 | Thomas, Jr. et al. | |
| 6,387,371 B1 | 5/2002 | Hudziak et al. | |
| 6,399,063 B1 | 6/2002 | Hudziak et al. | |
| 6,399,743 B1 | 6/2002 | Majumdar | |
| 6,414,130 B1 * | 7/2002 | Doherty et al. | |
| 6,417,168 B1 | 7/2002 | Greene et al. | |
| 6,441,143 B1 | 8/2002 | Koski | |
| 6,541,214 B1 | 4/2003 | Clinton | |
| 2001/0014326 A1 | 8/2001 | Andya et al. | |
| 2001/0021505 A1 | 9/2001 | Morris et al. | |
| 2002/0045215 A1 | 4/2002 | Majumdar | |
| 2002/0064785 A1 | 5/2002 | Mass | |
| 2002/0146420 A1 | 10/2002 | Bennett et al. | |
| 2002/0155527 A1 | 10/2002 | Stuart et al. | |

(Continued)

FOREIGN PATENT DOCUMENTS

AU    B-64135    3/1991

(Continued)

OTHER PUBLICATIONS

Baselga (J. Nat. Cancer Inst., 85: 1327-1333, 1993).*

(Continued)

*Primary Examiner*—Alana M. Harris
*Assistant Examiner*—Anne L. Holleran
(74) *Attorney, Agent, or Firm*—Barry L. Davison; Davis Wright Tremaine LLP

(57) ABSTRACT

An alternative HER-2/neu product, herstatin, consists of subdomains I and II from the ectodomain of p185HER-2 and a unique 79 amino acid C-terminus encoded by intron 8. Recombinant herstatin added to cells was found to bind to and inhibit p185HER-2. The effects of ectopic expression of herstatin in combination with either p185HER-2 or with its homolog, the EGF receptor, in several cell lines was studied. Cotransfection of herstatin with HER-2 inhibited p185HER-2 levels and caused an approximate 8 fold reduction in p185 tyrosine phosphorylation. Inhibition of p185HER-2 tyrosine phosphorylation corresponded to a dramatic decline in colony formation by cells that coexpressed p185HER-2 and herstatin. Herstatin also interfered with EGF activation of the EGF receptor in cotransfected cells demonstrated by impaired receptor tyrosine phosphorylation, reduced receptor down-regulation, and growth suppression. For both p185HER-2 and the EGF receptor, the extent of inhibition was affected by the expression levels of herstatin relative to the receptor. Herstatin is an autoinhibitor of p185HER-2 and expands its inhibitory activity to another member of the group I family of receptor tyrosine kinases, the EGF receptor.

20 Claims, 14 Drawing Sheets

U.S. PATENT DOCUMENTS

| | | | |
|---|---|---|---|
| 2002/0165193 | A1 | 11/2002 | Greene et al. |
| 2002/0172984 | A1 | 11/2002 | Holland et al. |
| 2002/0173458 | A1 | 11/2002 | Ruben et al. |
| 2003/0036179 | A1 | 2/2003 | Baker et al. |
| 2003/0044842 | A1 | 3/2003 | Desnoyers et al. |
| 2003/0044945 | A1 | 3/2003 | Baker et al. |
| 2003/0055239 | A1 | 3/2003 | Kendall et al. |
| 2003/0059863 | A1 | 3/2003 | Clinton |
| 2003/0078222 | A1 | 4/2003 | Ghildyal et al. |
| 2004/0022785 | A1 | 2/2004 | Clinton |
| 2004/0052796 | A1 | 3/2004 | Clinton et al. |
| 2005/0239088 | A1 | 10/2005 | Shepard et al. |

FOREIGN PATENT DOCUMENTS

| | | |
|---|---|---|
| CA | 2055441 | 11/1990 |
| CA | 2042064 | 2/1991 |
| CA | 2187781 | 9/1995 |
| CA | 2260061 | 1/1998 |
| CA | 2418083 | 2/2002 |
| EP | 0412116 | 4/1989 |
| EP | 0494135 | 9/1989 |
| EP | 0 119 528 B1 | 5/1992 |
| EP | 0 491 675 A1 | 6/1992 |
| EP | 0 171 407 B1 | 11/1993 |
| EP | 0 474 727 B1 | 7/1997 |
| EP | 0 600 744 B1 | 3/1998 |
| EP | 1 006 194 A2 | 6/2000 |
| EP | 1 114 863 A2 | 7/2001 |
| EP | 0 444 181 B1 | 10/2001 |
| EP | 1 304 110 A2 | 4/2003 |
| EP | 1 308 455 A2 | 5/2003 |
| WO | WO 85/03357 | 8/1985 |
| WO | WO 89/10412 | 11/1989 |
| WO | WO 90/14357 | 11/1990 |
| WO | WO 91/02062 | 2/1991 |
| WO | WO 91/05264 | 4/1991 |
| WO | WO 91/11715 | 8/1991 |
| WO | WO 92/14748 | 9/1992 |
| WO | WO 92/20798 | 11/1992 |
| WO | WO 93/14124 | 7/1993 |
| WO | WO 95/25166 | 9/1995 |
| WO | WO 95/30331 | 11/1995 |
| WO | WO 98/23782 | 6/1996 |
| WO | WO 98/02438 | 1/1998 |
| WO | WO 99/19732 | 4/1999 |
| WO | WO 99/39729 | 8/1999 |
| WO | WO 00/27426 | 5/2000 |
| WO | WO 00/29609 | 5/2000 |
| WO | WO 00/44403 | 8/2000 |
| WO | WO 01/01748 | 1/2001 |
| WO | WO 01/26607 | 4/2001 |
| WO | WO 01/61356 | 8/2001 |
| WO | WO 01/89566 | 11/2001 |
| WO | WO 02/11677 | 2/2002 |
| WO | WO 02/12335 | 2/2002 |
| WO | WO 02/14470 | 2/2002 |
| WO | WO 02/090991 | 11/2002 |
| WO | WO 03/025141 | 3/2003 |
| WO | WO 03/035843 | 5/2003 |
| WO | WO 2003/060071 A3 | 7/2003 |
| WO | WO 05/16966 | 2/2005 |

OTHER PUBLICATIONS

Fan (Cancer Res., 53: 4637-4642, 1993).*
Baselga (Breast Cancer Res. Treatment, 29: 127-138, 1994).*
Prewett (International J. Oncology, 9(2): 217-224, 1996).*
Lazar, E. et al, Molecular and Cellular Biology, 8(3): 1247-1252, 1988.*
Burgess, W.H. et al., J. Cell Biology, 111:2129-2138, 1990.*
Bowie et al, Science, 247: 1306-1310, 1990.*
Burgess et al, J. Cell Biology, 111:2129-2138, 1990.*
Lazar et al, Molecular and Cellular Biology, 8: 1247-1252, 1988.*
Hwang, S.L. et al. Kaohsiung J. Md. Sci., 13(7): 417-424, 1997; abstract only.*
Stedman's Medical Dictionary 27th Edition, Lippicott Williams & Wilkins, 2000, defintion for astrocyte.*
Stedman's Medical Dictionary 27th Edition, Lippicott Williams & Wilkins, 2000, defintion for glial.*
Shamieh et al., Receptor binding specificities of Herstatin and its intron 8-encoded domain, FEBS Letters 568:163-166, 2004.
Basu, A. et al., "Inhibition of tyrosine kinase activity of the epidermal growth factor (EGF) receptor by a truncated receptor form that binds to EGF: role for interreceptor interaction in kinase regulation," Mol. Cell. Biol. 9:671-677 (1989).
Bird, R.E. "Single-chain antigen-binding proteins," Science 242:423-426 (1988).
Bond, C.T. et al., "Cloning and functional expression of the cDNA encoding an inwardly-rectifying potassium channel expressed in pancreatic beta-cells and in the brain," FEBS Letters 367:61-66 (1995).
Bork, P., "Powers and pitfalls in sequence analysis: the 70% hurdle," Genome Research 10: 398-400 (2000).
Brodowicz et al, "Soluble HER-2/neu neutralizes biologic effects of anti-HER-2/neu antibody on breast cancer cells in vitro," Int. J Cancer. 73(6):875-879 (1997).
Brown et al., "Antibodies against highly conserved sites in the epidermal growth factor receptor tyrosine kinase domain as probes for structure and function," Biochemistry 32(17):4659-64 (1993).
Carraway, K.L. 3rd, and Cantley, L.C., "A neu acquaintance for erbB3 and erbB4: a role for receptor heterodimerization in growth signaling," Cell 78:5-8 (1994).
Carter, T.H. and Kung H.J. "Tissue-specific transformation by oncogenic mutants of epidermal growth factor receptor," Crit Rev Oncog. 5(4):389-428 (1994).
Clinton et al. "Estrogen action in human ovarian cancer."Crit Rev Oncol. Heamatol. Jan.; 25(1):1-9 (1997).
Clinton et al. "Estrogens increase the expression of fibulin-1, an extracellular matrix protein secreted by human ovarian cancer cells." PNAS USA Jan. 9;93(1):316-320 (1996).
Clinton, G.M. and N.A. Brown, "Generation and use of anti-peptide antibodies directed against catalytic domain of protein kinases," Methods in Enzymology 200:463-74 (1991).
Codony-Servant J et al "Cleavage of the HER2 ectodomain is a pervanadate-activable process that is inhibited by the tissue inhibitor of metalloproteases-1 in breast cancer cells." Cancer Research 59 (6): 1196-1201 (1999).
Cole et al. "Monoclonal Antibodies And Cancer Therapy." Alan R. Liss, Inc., pp. 77-96 (1985).
Cote, R.A. et al. "Generation of Human Monoclonal Antibodies Reactive with Cellular Antigens ," Proc. Natl. Acad. Sci. USA 80:2026-2030 (1983).
Dermer et al. "Another Anniversary for the War on Cancer." Bio/Technology 12:320 (1994).
Di Fiore, P.P. et al., "erbB-2 is a potent oncogene when overexpressed in NIH/3T3 cells," Science 237:178-182 (1987).
Dillman, R.O. "Antibodies as cytotoxic therapy." J. Clin. Oncol. 12:1497-1515 (1994).
Dougall et al., "The neu-oncogene: signal transduction pathways, transformation mechanisms and evolving therapies," Oncogene 9:2109-2133 (1994).
Earp, H.S., et al., "Heterodimerization and functional interaction between EGF receptor family members: a new signaling paradigm with implications for breast cancer research," Breast Cancer Res. Treat. 35:115-132 (1995).
Fitzpatrick, V.D. et al., "Formation of a high affinity heregulin binding site using the soluble extracellular domains of ErbB2 with ErbB3 or ErbB4," FEBS Letters 431:102-106 (1998).
Flickinger, T.W. et al., "An alternatively processed mRNA from the avian c-erbB gene encodes a soluble, truncated form of the receptor that can block ligand-dependent transformation," Mol. Cell. Biol. 12:883-893 (1992).
Greenspan, N.S., and Bona, C.A., "Idiotypes: structure and immunogenicity," FASEB J 7 5:437-444 (1993).

Greenspan et al., "Defining epitopes: It's not as easy as it seems," Nature Biotech. 7: 936-937 (1999).

Groenen, L.C. et al., "Structure-function relationships for the EGF/TGF-alpha family of mitogens," Growth Factors 11:235-257 (1994).

Hansen et al., "Re-examination and further development of a precise and rapid dye method for measuring cell growth/cell kill." Immunol. Methods. 119(2):203-210, (1989).

Heldin, C.H., and Ostman, A., "Ligand-induced dimerization of growth factor receptors: variations on the theme," Cytokine Growth Factor Rev. 7:33-40 (1996).

Hudziak et al., "Increased expression of the putative growth factor receptor p185HER2 causes transformation and tumorigenesis of NIH 3T3 cells," Proc Natl Acad Sci U S A 84(20):7159-63 (1987).

Hurwitz, E. et al. "Suppression and promotion of tumor growth by monoclonal antibodies to ErbB-2 differentially correlated with cellular uptake." Proc Natl Acad Sci U S A. Apr. 11;92(8):3353-7 (1995).

Huse, W.D. et al., "Generation of a large combinatorial library of the immunoglobulin repertoire in phage lambda," Science, 246:1275-1281 (1989).

Huston, J.S. et al., "Protein engineering of antibody binding sites: recovery of specific activity in an anti-digoxin single-chain Fv analogue produced in *Escherichia coli*," Proc. Natl. Acad. Sci. USA 85:5879-5883 (1988).

Hynes, N.E., Stern, D.F., "The biology of erbB-2/neu/HER-2 and its role in cancer," Biochem. et Biophys. Acta 1198:165-184 (1994).

Jhabvala-Romero et al., "Herstatin inhibits heregulin-mediated breast cancer cell growth and overcomes tamoxifen resistance in breast cancer cells that overexpress HER-2," Oncogene 22:8178-8186 (2003).

Justman, Q.A. and G.M. Clinton, "Herstatin, an autoinhibitor of the human epidermal growth factor receptor 2 tyrosine kinase, modulates epidermal growth factor signaling pathways resulting in growth arrest," J. Biol. Chem. 277:20618-20624 (2002).

Kern et al., "Inhibition of human lung cancer cell line growth by an anti-p185HER2 antibody," Am. J. Respir. Cell. Mol. Biol. 9(4):448-54 (1993).

Kohler, G., and Milstein, C., "Continuous cultures of fused cells secreting antibody of predefined specificity," Nature 256:495-497 (1975).

Kozbor, D. and Roder, J.C., "The production of monoclonal antibodies from human lymphocytes," Immunology Today 4:72 (1983).

Krainer, M. et al, "Tissue Expression and Serum Levels of HER-2/neu in Patients with Breast Cancer," Oncology 54:475-481 (1997).

Kraus, M.H. et al., "Overexpression of the EGF receptor-related proto-oncogene erbB-2 in human mammary tumor cell lines by different molecular mechanisms." EMBO J 6:605-610 (1987).

Kurokawa, H., "Inhibition of HER2/neu (erbB-2) and mitogen-activated protein kinases enhances tamoxifen action against HER2-overexpressing, tamoxifen-resistant breast cancer cells," Cancer Res., 60:5887-94 (2000).

Langton et al. "An antigen immunologically related to the external domain of gp185 is shed from nude mouse tumors overexpressing the c-ERBB-2 (Her-2/Neu) oncogene." Canc. Res. 51:2593-2598 (1991).

Lax, I. et al., "Localization of a major receptor-binding domain for epidermal growth factor by affinity labeling," Mol. Cell. Biol. 8:1831-1834 (1988).

Lee, H., and Maihle, N.J., "Isolation and characterization of four alternate c-erbB3 transcripts expressed in ovarian carcinoma-derived cell lines and normal human tissues," Oncogene 16:3243-3252 (1998).

Lee et al., "A naturally occurring secreted human ErbB3 receptor isoform inhibits heregulin-stimulated activation of ErbB2, ErbB3, and ErbB4," Cancer Research 61:4467-4473 (2001).

Lee et al. "Serum tyrosine kinase activity and neoplastic disease." Recent Results Cancer Res. 113:32-40 (1989).

Lee, K.F., et al., "Requirement for neuregulin receptor erbB2 in neural and cardiac development." Nature 378:394-398 (1995).

Leitzel, K. et al., "Elevated soluble c-erbB-2 antigen levels in the serum and effusions of a proportion of breast cancer patients." J Clin. Oncol. 10: 1436-1443 (1992).

Lemmon, M.A. et al., "Two EGF molecules contribute additively to stabilization of the EGFR dimer." EMBO J. Jan. 15;16(2):281-94 (1997).

Lewis et al., "Differential responses of human tumor cell lines to anti-p185HER2 monoclonal antibodies," Cancer Immunol. Immunother. 37(4):255-63 (1993).

Libermann, T.A. et al., "Amplification, enhanced expression and possible rearrangement of EGF receptor gene in primary human brain tumours of glial origin." Nature. Jan. 10-18;313(5998):144-7, (1985).

Lin et al. "Human prostatic acid phosphatase has phosphotyrosyl protein phosphatase activity." Biochem J. Apr. 15;235(2):351-7 (1986).

Lin et al. "Developmental expression of tyrosyl kinase activity in human serum." Hum Biol. Jun.;59(3):549-56 (1987).

Lin et al. "Characterization of tyrosyl kinase activity in human serum." J Biol Chem. Feb. 10;260(3):1582-7 (1985).

Lin et al., "Disulfide-linked and noncovalent dimmers of p185HER-2 in human breast carcinoma cells," J. Cell. Biochem. 49(3):290-5 (1992).

Lin et al. "Tyrosyl kinase activity is inversely related to prostatic acid phosphatase activity in two human prostate carcinoma cell lines.". Mol Cell Biol Dec.;6(12):4753-7 (1986).

Lin et al. "The epidermal growth factor receptor from prostate cells is dephosphorylated by a prostate-specific phosphotyrosyl phosphatase." Mol Cell Biol. Dec;8(12):5477-85 (1988).

Lin et al., "Insulin and epidermal growth factor stimulate phosphorylation of p185HER-2 in the breast carcinoma cell line, BT474," Molecular and Cellular Endocrinology, 69(2-3):111-119 (1990).

Lin et al., "A soluble protein related to the HER-2 proto-oncogene product is released from human breast carcinoma cells," Oncogene 6(4):639-643 (1991).

Liu, Y., et al., "MCF-7 breast cancer cells overexpressing transfected c-erbB-2 have an in vitro growth advantage in estrogen-depleted conditions and reduced estrogen-dependence and tamoxifen-sensitivity in vivo," Breast Cancer Res. Treat., 34:97-117 (1995).

Maisonpierre, P.C. et al., "Angiopoietin-2, a natural antagonist for Tie2 that disrupts in vivo angiogenesis," Science 277:55-60 (1997).

Meden, H. et al, "Prognostic significance of p105 (c-erbB-2 HER2/neu) serum levels in patients with ovarian cancer," Anticancer Res. 17:757-760 (1997).

Molina et al., "NH2-terminal truncated HER-2 protein but not full-length receptor is associated with nodal metastasis in human breast cancer," Clinical Cancer Research 8:347-353 (2002).

Morrison, S.L. et al., "Chimeric Human Antibody Molecules: Mouse Antigen-Binding Domains with Human Constant Region Domains," Proc. Natl. Acad. Sci. USA, 81:6851-6855 (1984).

Moscatello, D.K. et al., "Transformation and altered signal transduction by a naturally occurring mutant EGF receptor," Oncogene. Jul. 4;13(1):85-96 (1996).

Myers et al. "Elevated serum levels of p105(erbB-2) in patients with advanced-stage prostatic adenocarcinoma." Int. J. Cancer (Pred. Oncol.) 69:398-402, (1996).

Natali et al., "Expression of the p185 encoded by HER2 Oncogene in normal and transformed human tissues," Int. J. Cancer 45:457-461 (1990).

Neuberger, M.S. et al., "Recombinant antibodies possessing novel effector functions," Nature, 312:604-608 (1984).

Nisonoff, A., "Idiotypes: concepts and applications," J Immunol. 147:2429-2438 (1991).

O'Rourke et al., "Trans receptor inhibition of human glioblastoma cells by erbB family ectodomains," Proc Natl Acad Sci U S A. 94(7):3250-5 (1997).

Pavelic, K. et al., "Evidence for a role of EGF receptor in the progression of human lung carcinoma," Anticancer Res. Jul.-Aug.; 13(4):1133-7 (1993).

Pegram et al., "Biological rationale for HER2/new (c-erbB2) as a target for monoclonal antibody therapy," Seminars in Oncology 27(5 Suppl. 9):13-19 (2000).

Petch et al., "A truncated, secreted form of the epidermal growth factor receptor is encoded by an alternatively spliced transcript in normal rat tissue," Mol. Cell. Biol. 10:2973-2982 (1990).

Pietras, R. J., et al., "HER-2 tyrosine kinase pathway targets estrogen receptor and promotes hormone-independent growth in human breast cancer cells," Oncogene, 10:2435-46 (1995).

Pupa, S.M. et al., "The extracellular domain of the c-erbB-2 oncoprotein is released from tumor cells by proteolytic cleavage," Oncogene 8:2917-2923 (1993).

Qian, X. et al., ""Intermolecular association and trans-phosphorylation of different neu-kinase forms permit SH2-dependent signaling and oncogenic transformation,"" Oncogene 10:211-219 (1995).

Schweitzer, R. et al., "Inhibition of Drosophila EGF receptor activation by the secreted protein Argos," Nature 376:699-702 (1995).

Segatto, O. et al. "Different Structural Alterations Upregulate In Vitro Tyrosine Kinase Activity and Transforming Potency of the erbB-2 Gene." Mol. Cell. Biol. 8(12):5570-5574 (1988).

Sharp, P.A., and Burge, C.B., "Classification of introns: U2-type or U12-type," Cell 91:875-879 (1997).

Shepard et al. "Monoclonal antibody therapy of human cancer: taking the HER2 protooncogene to the clinic," J. Clin. Immunol. 11(3): 117-127 (1991).

Slamon, D.J. et al., "Human breast cancer: correlation of relapse and survival with amplification of the HER-2/neu oncogene," Science 235:177-182 (1987).

Slamon, D.J. et al., "Studies of the HER-2/neu proto-oncogene in human breast and ovarian cancer," Science 244:707-712 (1989).

Staverosky et al., "Herstatin, an autoinhibitor of the epidermal growth factor (EGF) receptor family, blocks the intracranial growth of glioblastoma," Clin. Canc. Res. 11(1):335-40 (2005).

St-Jacques, S. et al., "Molecular characterization and in situ localization of murine endoglin reveal that it is a transforming growth factor-beta binding protein of endothelial and stromal cells," Endocrinology 134:2645-2657 (1994).

Stern, D.F. et al., "p185, a product of the neu proto-oncogene, is a receptorlike protein associated with tyrosine kinase activity," Mol. Cell. Biol. 6:1729-1740 (1986).

Takeda, S. et al., "Construction of chimaeric processed immunoglobulin genes containing mouse variable and human constant region sequences," Nature, 314: 452-454 (1985).

Tal, M., King, C.R., Kraus, M.H., Ullrich, A., Schlessinger, J. and Givol, D., "Human HER2 (neu) promoter: evidence for multiple mechanisms for transcriptional initiation," Mol. Cell. Biol. 7 (7), 2597-2601 (1987).

Tanner K.G., and Kyte, J., "Dimerization of the extracellular domain of the receptor for epidermal growth factor containing the membrane-spanning segment in response to treatment with epidermal growth factor," J Biol Chem. Dec. 10;274(50):35985-90 (1999).

Tyson, F.L. et al., "Expression and amplification of the HER-2/neu (c-erbB-2) protooncogene in epithelial ovarian tumors and cell lines," Am. J Obstet. Gynecol. 165:640-646 (1991).

Tzahar, E. et al., "Bivalence of EGF-like ligands drives the ErbB signaling network," EMBO J. 16:493 8-4950 (1997).

Ullrich, A. et al., "Human epidermal growth factor receptor cDNA sequence and aberrant expression of the amplified gene in A431 epidermoid carcinoma cells," Nature. May 31-Jun. 6;309(5967):418-25 (1984).

Vecchi, M., and Carpenter, G., "Constitutive proteolysis of the ErbB-4 receptor tyrosin kinase by a unique, sequential mechanism," J Cell Biol. 139:995-1003 (1997).

Vecchi, M. et al., "Selective cleavage of the heregulin receptor ErbB-4 by protein kinase C activation," J Biol. Chem. 271:18989-18995 (1996).

Ward, E.S. et al., "Binding activities of a repertoire of single immunoglobulin variable domains secreted from *Escherichia coli*," Nature 334:544-546 (1989).

Woltjer, R.L. et al. "Direct identification of residues of the epidermal growth factor receptor in close proximity to the amino terminus of bound epidermal growth factor." Proc Natl Acad Sci U S A. Aug 15;89(16):7801-5 (1992).

Wu, D. et al., "Human Epidermal Growth Factor Receptor Residue Covalently Cross-Linked to Epidermal Growth Factor," Proc Natl Acad Sci U S A. Apr.;87(8):3151-5 (1990).

Xia et al., "Combination of EGFR, HER-2/neu, and HER-3 is a stronger predictor for the outcome of oral squamous cell carcinoma than any individual family members," Clin. Canc. Res. 5:4164-4174 (1999).

Xu et al., "Antibody-induced growth inhibition is mediated through immunochemically and functionally distinct epitopes on the extracellular domain of the c-erbB-2 (HER-2/neu) gene product p185," Int. J. Canc. 53:401-408 (1993).

Baasner, S. et al., "Reversible tumorigenesis in mice by conditional expression of the HER2/c-erbB2 receptor tyrosine kinase," Oncogene 13:901-911 (1996).

Bargman, C.I. et al. "Oncogenic activation of the neu-encoded receptor protein by point mutation and deletion." EMBO 7(7):2043-2052 (1988).

Baselga, J., et al., "Phase II study of weekly intravenous receombinant humanized anti-p185HER2 monoclonal antibody in patients with HER2/neu-overexpressing metastatic breast cancer," J Clin. Oncol. 14:737-744 (1996).

"Circulatory HER2 extracellular domain (CCD) levels in Multiple Tumor Xenograft Models of HER-overexpressing Breast Cancer," Park, J.W., G. Colbern, A. Duijens, J. Baselga, D. Papahadjopoulos, C.C. Benz, UCSF, California; Geraldine Brush Cancer Research Institute, CPMC, SF, CA; Genentech, Inc. So. S.F., CA; Memorial Sloan-Kettering Cancer Center, NY, NY. 1997.

Christianson, Tracy A. et al., "$NH_2$-terminally truncated HER-2/neu Protein: Relationship with Shedding of the Extracellular Domain and with Prognostic Factors in Breast Cancer," *Cancer Research 58*, 5123-5129, Nov. 15, 1998.

Doherty et al., The HER-2/neu receptor tyrosine kinase gene encodes a secreted autoinhibitor. Proc. Natl. Acad. Sci. 96:10869-10874, 1999.

Valeron et al., Quantitative analysis of $p185^{HER-2/neu}$ protein in breast cancer and its association with other prognostic factors. Intl. J. Cancer (Pred. Oncol) 74:175-179, 1997.

Zebrecky et al., The extracellular domain of p185/neu is released from the surface of human breast carcina cells, SK-BR-3. J. Biol. Chem. 266(3):1716-1720, 1991.

Press et al., Her-2/*neu* expression in node-negative breast cancer: direct tissue quantitation by computerized image analysis and association of overexpression with increased risk of recurrent disease. Cancer Res. 53:4960-4970, 1993.

Reiter et al., A 1.8 kb alternative transcript from the human epidermal growth factor receptor gene encodes a truncated form of the receptor. Nucl. Acids. Res. 24(20):4050-4056, 1996.

Ross et al., The Her-2/neu oncogene in breast cancer: Prognostic factor, predictive factor, and target for therapy. *Stem Cells*, Alphamed Press, Dayton, OH US, vol. 16 No. 6, pp. 413-428, 1998.

Scott et al., A truncated intracellular HER2/neu receptor produced by alternative RNA Processing affects growth of human carcinoma cells, Molec. And Cellular Biol. 13(4): 2247-2257, 1993.

Yamamoto et al., Similarity of protein encoded by the human c-*erb-B-2* gene to epidermal growth factor receptor, Nature 319:230-234, 1986.

Coussens, et al., Tyrosine Kinase Receptor with Extensive Homology to EGF Receptor Shares Chromosomal Location with *neu* Oncogene, Science 230:1132-1139, 1985.

Azios et al., Expression of herstatin, an autoinhibitor of HER-2/neu, inhibits transactivation of HER-3 by HER-2 and blocks EGF activation of the EGF receptor, Oncogene 20:5199-5209, 2001.

Aigner et al., Expression of a truncated 100 kDa HER2 splice variant acts as an endogenous inhibitor of tumour cell proliferation, Oncogene 20:2101-2111, 2001.

Baselga and Mendelsohn, The epidermal growth factor receptor as a target for therapy in breast carcinoma, Breast Cancer Research and Treatment 29:127-138, 1994.

Baselga et al., Antitumor Effects of Doxorubicin in Combination With Anti-epidermal Growth Factor Receptor Monoclonal Antibodies, Journal of the national Cancer Institute, vol. 85, No. 16, Aug. 18, 1993.

Fan et al., Antitumor Effect of Anti-Epidermal Growth Factor Receptor Monoclonal Antibodies plus cis-Diamminedichloroplatinum on Well Established A431 Cell Xenografts, Cancer Res. 53:4637-4642, 1993.

Gleason et al., Platelet Derived Growth Factor (PDGF), Androgens and Inflammation: Possible Etiologic Factors in the Development of Prostatic Hyperplasia, J. Urol. 149:1586-1592, 1993.

Pegram et al., The Molecular and Cellular Biology of HER2/neu Gene Amplification/Overexpression and the Clinical Development of Herceptin (Trastuzumab) Therapy for Breast Cancer, Chapter 4: Clinical Development of Herceptin Therapy for Breast Cancer, pp. 58-75, 2000.

Prewett et al., Anti-tumor and cell cycle responses in KB cells treated with a chimeric anti-EGFR monoclonal antibody in combination with cisplatin, International Journal of Oncology 9:217-224, 1996.

Reiter and Maihle, A 1.8 kb alternative transcript from the human epidermal growth factor receptor gene encodes a truncated form of the receptor, Nucl. Acids Res. 24:20) 4050-4056, 1996.

Ross and Fletcher, The HER-2/new Oncogene in Breast Cancer: Prognostic Factor, Predictive Factor and Target for Therapy, Stem Cells 16:413-428, 1998.

Burdick et al., Treatment of Ménétrier's Disease with a Monoclonal Antibody against the Epidermal Growth Factor Receptor, New Engl. J. Med. 343(23):1697-1701, 2000.

* cited by examiner

HER-2 Intron 8 Polymorphisms

```
1    G  T  H  S  L  P  P  R  P  A  A  V  P  V  P  L  R  M  Q  P  G
1    GGTACCCACTCACTGCCCCCGAGGCCAGCTGCAGTTCCTGTCCCTCTGCGCATGCAGCCTGGC
        X       X  X                             X     X        X

22   P  A  H  P  V  L  S  F  L  R  P  S  W  D  L  V  S  A  F  Y  S
64   CCAGCCCACCCTGTCCTATCCTTCCTCAGACCCTCTTGGGACCTAGTCTCTGCCTTCTACTCT
                                                X

43   L  P  L  A  P  L  S  P  T  S  V  P  I  S  P  V  S  V  G  R  G
127  CTACCCCTGGCCCCCCTCAGCCCTACAAGTGTCCCTATATCCCCTGTCAGTGTGGGGAGGGGC
                                        X

64   P  D  P  D  A  H  V  A  V  D  L  S  R  Y  E  G stop 80
190  CCGGACCCTGATGCTCATGTGGCTGTTGACCTGTCCCGGTATGAAGGCTGA 240
        X                 X
```

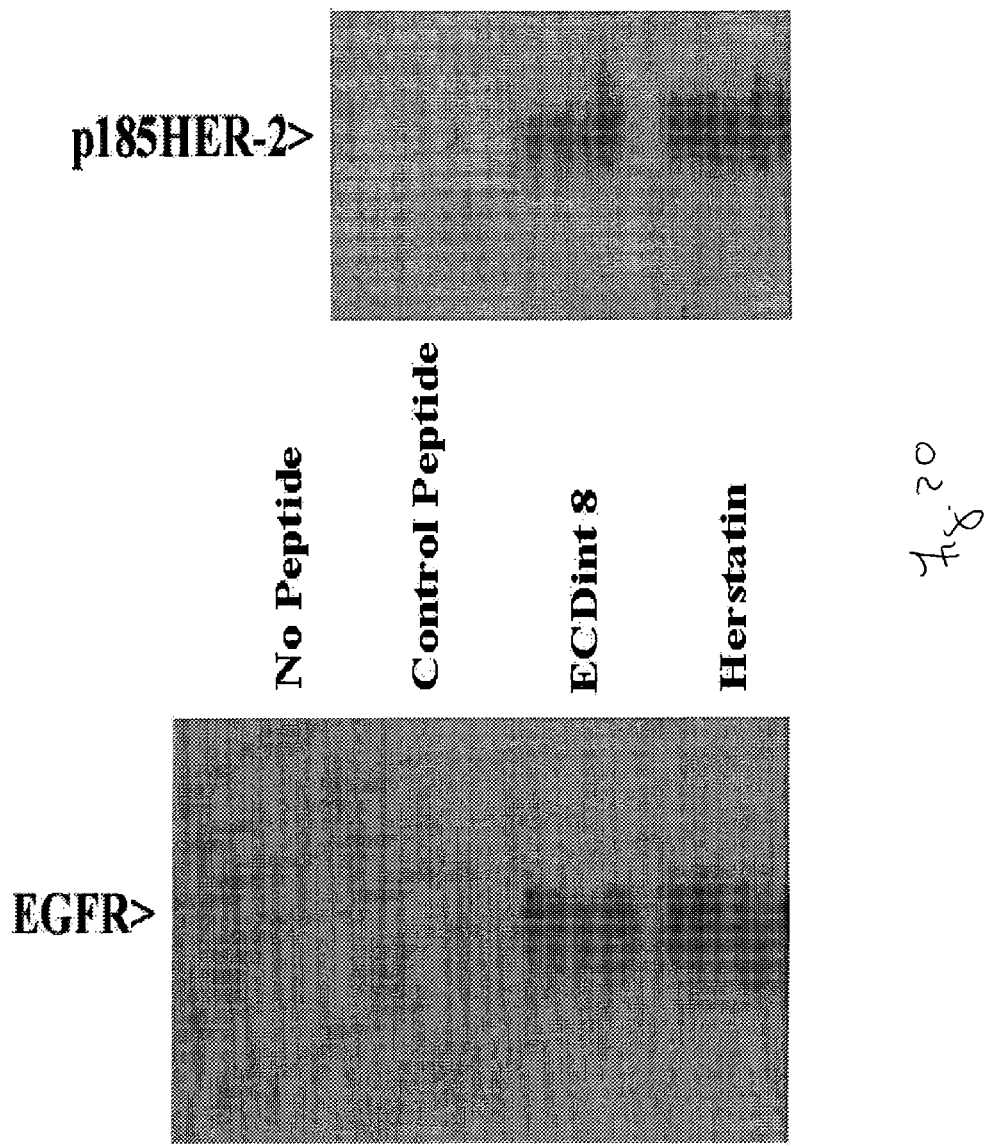

COMPOSITIONS AND METHODS FOR TREATING CANCER BY MODULATING HER-2 AND EGF RECEPTORS

This work was supported by a grant from the Department of Defense (DOD) Breast Cancer Research Program. The United States Government has certain rights in this invention.

TECHNICAL FIELD OF THE INVENTION

This invention relates generally to signaling through ErbB family member receptors, and to novel methods and compositions for modulating HER-2, and EGF receptor-mediated signaling.

BACKGROUND OF THE INVENTION

A HER-2 binding antagonist is described and provided. Specifically, intron retention has generated a novel HER-2 antagonist polypeptide that binds to the HER-2 receptor.

The HER-2/neu (erbB-2) oncogene encodes a receptor-like tyrosine kinase (RTK) that has been extensively investigated because of its role in several human carcinomas (Hynes and Stem, *Biochim. et Biophys. Acta* 1198:165-184, 1994; and Dougall et al., *Oncogene* 9:2109-2123, 1994) and in mammalian development (Lee et al., *Nature* 378:394-398, 1995). The sequence of the HER-2 protein was determined from a cDNA that was cloned by homology to the epidermal growth factor receptor (EGFR) mRNA from placenta (Coussens et al., *Science* 230:1132-1139, 1985) and from a gastric carcinoma cell line (Yamamoto et al., *Nature* 319:230-234, 1986). The HER-2 mRNA was shown to be about 4.5 kb (Coussens et al., *Science* 230:1132-1139, 1985; and Yamamoto et al., *Nature* 319:230-234, 1986) and encodes a transmembrane glycoprotein of 185 kDa in normal and malignant human tissues (p185HER-2) (Hynes and Stern, *Biochim. et Biophys. Acta* 1198:165-184, 1994; and Dougall et al., *Oncogene* 9:2109-2123, 1994). The function of the HER-2 gene has been examined mainly by expressing the cDNA corresponding to the 4.5 kb transcript in transfected cells and from the structure and biochemical properties of the 185 kDa protein product. P185HER-2 consists of a large extracellular domain, a transmembrane segment, and an intracellular domain with tyrosine kinase activity (Hynes and Stern, *Biochim. et Biophys. Acta* 1198:165-184, 1994; and Dougall et al., *Oncogene* 9:2109-2123, 1994). Overexpression of p185HER-2 causes phenotypic transformation of cultured cells (DiFiore et al., *Science* 237:178-182, 1987; and Hudziak et al., *Proc. Natl. Acad. Sci. USA* 84:7159-7163, 1987) and has been associated with aggressive clinical progression of breast and ovarian cancer (Slamon et al., *Science* 235:177-182, 1987; and Slamon et al., *Science* 244:707-712, 1989). p185HER-2 is highly homologous to the EGFR. However, a ligand that directly binds with high affinity to p185HER-2 has not yet been identified. Moreover, the signaling activity of HER-2 may be mediated through heterodimerization with other ligand-binding members of the EGFR family (Carraway and Cantley, *Cell* 78:5-8, 1994; Earp et al., *Breast Cancer Res. Treat.* 35:115-132, 1995; and Qian et al., *Oncogene* 10:211-219, 1995).

Divergent proteins, containing regions of the extracellular domains of HER family RTKs, are generated through proteolytic processing of full length receptors (Lin and Clinton, *Oncogene* 6:639-643, 1991; Zabrecky et al., *J. Biol. Chem.* 266:1716-1720, 1991; Pupa et al., *Oncogene* 8:2917-2923, 1993; Vecchi et al., *J. Biol. Chem.* 271:18989-18995, 1996; and Vecchi and Carpenter, *J. Cell Biol.* 139:995-1003, 1997) and through alternative RNA processing (Petch et al., *Mol. Cell. Biol.* 10:2973-2982, 1990; Scott et al., *Mol. Cell. Biol.* 13:2247-2257, 1993; and Lee and Maihle, *Oncogene* 16:3243-3252, 1998). The extracellular domain of p185HER-2 is proteolytically shed from breast carcinoma cells in culture (Petch et al., *Mol. Cell. Biol.* 10:2973-2982, 1990; Scott et al., *Mol. Cell. Biol.* 13:2247-2257, 1993; and Lee and Maihle, *Oncogene* 16:3243-3252, 1998), and is found in the serum of some cancer patients (Leitzel et al., *J. Clin. Oncol.* 10:1436-1443, 1992) where it is may be a serum marker of metastatic breast cancer (Leitzel et al., *J. Clin. Oncol.* 10:1436-1443, 1992) and may allow escape of HER-2-rich tumors from immunological control (Baselga et al., *J. Clin. Oncol.* 14:737-744, 1966; and Brodowicz et al., *Int. J. Cancer* 73:875-879, 1997).

A truncated extracellular domain of HER-2 is also the product of a 2.3 kb alternative transcript generated by use of a polyadenylation signal within an intron (Scott et al., *Mol. Cell. Biol.* 13:2247-2257, 1993). The alternative transcript was first identified in the gastric carcinoma cell line, MKN7 (Yamamoto et al., *Nature* 319:230-234, 1986; and Scott et al., *Mol. Cell. Biol.* 13:2247-2257, 1993) and the truncated receptor was located within the perinuclear cytoplasm rather than secreted from these tumor cells (Scott et al., *Mol. Cell. Biol.* 13:2247-2257, 1993). However, no particular therapeutic, diagnostic or research utility has been ascribed to this truncated extracellular domain polypeptide. A truncated extracellular domain of the EGFR, generated by alternative splicing (Petch et al., *Mol. Cell. Biol.* 10:2973-2982, 1990) is secreted, exhibits ligand-binding, and dimerization properties (Basu et al., *Mol. Cell. Biol.* 9:671-677, 1989), and may have a dominant negative effect on receptor function (Basu et al., *Mol. Cell. Biol.* 9:671-677, 1989; and Flickinger et al., *Mol. Cell. Biol.* 12:883-893, 1992).

Group I receptor tyrosine kinases including the EGF-receptor (HER-1, erbB-1), HER-2 (erbB-2), HER-3 (erbB-3), and HER-4 (erbB-4) are widely expressed in epithelial, mesenchymal, and neuronal tissues and play fundamental roles in proliferation and differentiation. With the exception of p185HER-2, receptor tyrosine kinases are activated by binding to a variety of EGF-related growth factors. Ligand binding is coupled to receptor dimerization, tyrosine autophosphorylation, and signal activation. Independently of a specifically binding growth factor, p185HER-2 dimerizes with itself or is recruited as the preferred heterodimer partner where it transactivates receptor family members.

Enhanced amounts of group receptors at the cell membrane occurs frequently in human carcinomas. This elevation in number of receptors is likely to favor the formation of receptor oligomers resulting in amplified signaling. The EGF-receptor and p185 HER-2 have been most frequently and clearly associated with human malignancies. HER-2 is overexpressed in breast, ovarian, gastric, and endometrial carcinomas Elevated levels of p185HER-2 in 25-30% of breast and ovarian cancers predicts significantly lower survival rates and shorter time to relapse. Amplification and alteration of the EGF-receptor gene is often observed in squamous cell carcinoma of the lung (Pavelic et al., 1993) and in glial tumors (Libermann et al., 1985), particularly in glioblastoma, the most malignant glial tumor.

There have been extensive efforts directed toward defining the structure and function of the group I receptor extracellular domains in the interests of understanding the mechanism of receptor activation and in blocking receptor action at the cell surface. Receptor mutants consisting of the extracellular domain and a membrane anchor, in the absence of the cytoplasmic domain, are capable of dimerizing (Lemmon et al., 1997; Tzahar et al., 1997;Tanner and Kyte 1999) and forming kinase inactive complexes with cell surface receptors (Greene). The ectodomains of group I receptors have been divided into subdomains I, beginning at the N-terminus, through IV ending at the juxtamembrane position. Domains II and IV contain multiple cysteine residues that are conserved amongst the four group I receptors. Subdomains I and II appear to be a repeating unit of III and IV that may have arose by a gene duplication event (Ullrich et al., 1984). Deletion of subdomains I and II from the EGF receptor results in constitutive dimerization and oncogenic transformation in a ligand-independent fashion (Hayely et al., 1989; Carter and Kung 1994; Qian et al., 1994; Moscatello et al., 1996), and allows ligand independent heterodimer formation with the membrane anchored p185neu ectodomain mutant (Greene). While subdomain III contains the high affinity ligand binding site as shown for EGF binding to the EGF receptor (Wu et al., 1990 Woltjer et al., 1992 Lax et al., 1989; 1991), subdomain I has been suggested to serve as a low affinity site that is promiscuous in its ligand recognition (Lax et al., 1989; 1991 Tzahar et al., 1997). According to this model EGF-like ligands are bivalent with a high affinity site that binds to the direct receptor in subdomain III and a second, low affinity site with broad specificity for subdomain I that prefers interaction with p185HER-2, thereby explaining the status of p185HER-2 as the preferred dimer partner. Taken together these results suggest that subdomains I and II may exert a negative constraint on dimerization in the absence of ligand and could be important for recruitment of receptors into heterodimers.

Monoclonal antibodies against the ectodomains of p185HER-2 and the EGF-receptor have been shown to be effective in limiting growth of tumors. These antibodies bind to their receptor targets with high affinity and specificity and their toxicity is low. The mechanisms underlying the antitumorigenic effects of antibodies are unclear. The rhuMAb4D5 (HERCEPTIN®) antibody may act by downregulation of p185HER-2 at the cell surface (Hurwitz et al., 1995), which causes a reversible cytostatic effect on HER-2 mediated cell growth. Systemic administration of the monoclonal antibody rhuMAb4D5 (HERCEPTIN®) has been shown to have therapeutic efficacy, since it increases the time to recurrence in a subset of patients with metastatic breast cancer. High affinity humanized, monoclonal antibodies against the EGF receptor have also been used as antitumor agents. While the molecular mechanisms underlying the activity of EGF receptor antibodies remain elusive, those tested compete with growth factor binding. Antibody strategies that target p185HER-2 and the EGF-receptor, as well as heterodimers between these two receptors, have also been attempted. Preliminary evidence suggests that targeting both receptors may significantly augment antiproliferative effects.

Mutant receptors consisting of ectodomains have proved to be effective in inhibition of tumorigenesis. The membrane-anchored ectodomain of p185 neu, ectopically expressed in cells, functions as a dominant negative inhibitor based on its ability to dimerize with the ectodomains of group I receptors forming a kinase-inactive complex. P185neu ectodomain mutants are capable of specific inhibition of p185HER-2 homodimer signaling as well as trans-inhibition of EGF receptor signaling. Since p185HER-2 is the preferred heterodimer partner of group I RTKs, then the p185-ectodomain is capable of suppressing the activation of all group I receptors. However, membrane anchoring of ectodomain mutants is required to exert a dominant negative effect since interactions between soluble ectodomains and cell surface receptors are too weak to achieve complex formation.

SUMMARY OF THE INVENTION

The present invention is directed to a A naturally occurring inhibitor of the HER-2 receptor tyrosine kinase called herstatin which consists of the first 340 α-residues identical to N-terminal subdomains I and II of p185HER-2, followed by a novel C-terminus of 79 aa-residues and a stop codon specified by the inserted sequence. In contrast to soluble ectodomains, herstatin binds with high affinity (~14 nM Kd) to cell surface p185HER-2. Although herstatin is secreted and complexes with p185HER-2 at the cell surface, it differs from other EGR-like ligands in its ability to inhibit the activity of p185HER-2. In the current study we find that coexpression of herstatin with p185HER-2 causes a striking reduction in cell growth that corresponds with suppression of p185 autophosphorylation. Moreover the inhibitory activity of herstatin is extended to EGF activation of the EGF-receptor.

In another embodiment, a method for treating a solid tumor characterized by overexpression of EGF receptor is disclosed including administering an agent that binds to the extracellular domain (ECD) of EGF receptor. The agent is selected from the group consisting of (a) an isolated polypeptide having from about 50 to 79 amino acids taken from the sequence of SEQ ID NO. 1, wherein the polypeptide binds to the extracellular domain ECD of EGF receptor with an affinity binding constant of at least $10^8$ $M^{-1}$, (b) an isolated and glycosylated polypeptide having from about 80 to 419 amino acids taken from the sequence of SEQ ID NO. 2, wherein the C terminal 79 amino acids are present, and wherein at least three N-linked glycosylation sites are present, (c) a monoclonal antibody that binds to the ECD of EGF receptor, and (d) combinations thereof. The agent cannot be the monoclonal antibody alone.

In yet another embodiment, a pharmaceutical composition for treating solid tumors that overexpress EGF receptor is disclosed including an agent selected from the group consisting of (a) an isolated polypeptide having from about 50 to 79 amino acids taken from the sequence of SEQ ID NO. 1, wherein the polypeptide binds to the extracellular domain ECD of EGF receptor with an affinity binding constant of at least $10^8$ $M^{-1}$, (b) an isolated and glycosylated polypeptide having from about 80 to 419 amino acids taken from the sequence of SEQ ID NO. 2, wherein the C terminal 79 amino acids are present, and wherein at least three N-linked glycosylation sites are present, (c) a monoclonal antibody that binds to the ECD of EGF receptor, and (d) combinations thereof. The agent cannot be the monoclonal antibody alone, and pharmaceutically acceptable carrier.

An even further embodiment, a method for targeting a therapeutic agent to solid tumor tissue is disclosed. The method includes targeting a therapeutic agent to a solid tumor wherein the solid tumor tissue is characterized by overexpression of EGF receptor. The method includes attaching the therapeutic agent to an isolated polypeptide having from about 50 to 79 amino acids taken from the sequence of SEQ ID NO. 1. The polypeptide binds to the extracellular domain ECD of EGF receptor with an affinity binding constant of at least $10^8$ $M^{-1}$.

In yet another embodiment, a method for determining the prognosis of tumor treatment in a patient for a tumor that overexpresses EGF receptor is disclosed including: (a) obtaining a bodily fluid sample from a patient, wherein the bodily fluid is selected from the group consisting blood, serum, urine, lymph, saliva, tumor tissue, placental tissue, umbilical cord tissue, amniotic fluid, chorionic villi tissue and combinations thereof; (b) measuring the amount of p68HER-2 receptor expressed using an anti-p68HER-2 receptor antibody-based assay, wherein the assay is selected from the group consisting of ELISA, immunoprecipitation, immunohistocytochemistry, and Western analysis; (c) measuring the amount of EGF receptor ECD in the bodily fluid; and (d) determining a ratio between the amount of p68HER-2 and EGF receptor, whereby the higher the p68HER-2 to EGF receptor ratio, the better the prognosis of the patient.

One advantage of herstatin is in the development of therapeutics, particularly against human cancers that involve group I receptor tyrosine kinases. Another advantage of herstatin is its ability to suppress the growth of p185HER-2 or EGF receptor overexpressing cells.

BRIEF DESCRIPTION OF THE DRAWINGS

FIG. 8 shows the nucleotide (SEQ ID NO:16) and deduced amino acid sequence (SEQ ID NO:11) of HER-2 Intron 8. Human genomic DNA was subjected to PCR using primers that flank intron 8. PCR parameters were 30 cycles of 94° C. for 1 min, 62° C. for 1 min, 72° C. for 30 s, followed by 1 cycle of 72° C. for 7 min. A 410 bp product was gel purified and sequenced in the forward and reverse directions. The sequence shown is the most common sequence found within intron 8 from about 15 different individuals. Positions of sequence variation resulting in amino acid substitutions as disclosed herein are marked by Xs below the sequence.

In FIG. 9, upper panel, the transfected cells were analyzed at 48 hrs as a Western blot and reacted with antibodies against p185HER-2, anti-neu (C), or in the lower panel with antibodies against the intron 8-encoded C-terminal sequence of herstatin (anti-Hst). In FIG. 10, the transfections were conducted in triplicate using the indicated plasmids with the inclusion of 0.5 ug of β-galactosidase galactosidase expression plasmid driven by a CMV promoter. At 48 hrs, the cells were extracted, cell protein was quantitated by BioRad protein dye kit, and the β-galactosidase activity was measured as described. The β-galactosidase activity was normalized to protein amounts and the mean results with the standard deviations are plotted. A similar result was obtained when β-galactosidase activity was normalized to number of cells originally plated into each well.

In FIG. 13, Panel a, cells in duplicate wells were transfected with 0.25, 0.5, 1.0, and 3 μg of fluorescent green protein (FGP) expression plasmid. Empty vector was added to make the total amount of DNA equal to 3 μg in each well. At 48 hrs, the fluorescent signal was quantitated at a wavelength of 520 nM for emission and 490 mM for excitation for emission and for excitation using a fluorescent plate reader. In FIGS. 14 and 15, cells were transfected with 0.5 μg of FGP plasmid with or without 1.5 μg of HER-2 plasmid and with the indicated amounts of herstatin expression plasmid. Empty vector was added to make the total amount of DNA at 5 μg in each well. At 48 hrs, the cells were washed twice with PBS, extracted in 100 μg of modified RIPA containing 1 mM phenylmethylsulfonylfluoride and 2 mM orthovanadate. The protein concentration in the clarified extracts was determined using the BioRad protein dye kit. The extracted protein, 20 μg, was resolved in 7.5% polyacrylamide SDS gels and analyzed as a Western blot as described in Materials and Methods first using 1 μg/ml of anti-phosphotyrosine antibody (anti-PTyr) (Panel C). The blot was stripped and then was reacted with antibodies against p185HER-2 (anti-neu(C)). The blots were developed using chemiluminescent reagent (Pierce) and exposed to Kodak film.

In FIGS. 16 and 17 the cultures were incubated in the absence or presence of 100 ng/ml of EGF for 20 minutes and then extracted in modified RIPA as in FIGS. 13-15. 20 μg of protein from each well were resolved in 7% polyacrylamide SDS-gels and analyzed as a Western blot, first with 1 μg/ml of anti-phosphotyrosine antibody (FIG. 17). The blot was then stripped and probed with anti-EGF receptor antibody. In FIG. 18 the cultures were incubated in the absence or presence of 100 ng/ml of EGF for 24 hrs. The cell extracts were then analyzed as a Western blot using anti-EGF receptor antibody.

FIG. 20 shows immobilized intron 8-encoded peptide or herstatin pulls-down the EGF receptor and p185HER-2. About 100 μl of a 50% suspension of S-protein agarose (Novagen) was incubated with no peptide, with 50 μg of TBpex14 peptide (provided by Dr. B. Ullman, OHSU), 50 μg of intron 8-encoded peptide, or 50 μg full length recombinant herstatin at room temperature for 1 hr. Each of these peptides contained an S-protein tag encoded by the pET 30 expression plasmid (Novagen). The agarose samples were then washed twice with PBS and incubated at room temperature for 1 hr with 100 μg of A431 cell extract, for the EGF receptor, or 17-3-1 extract, for p185HER-2, solubilized in PBS containing 1% nonidet-p40 (PBSNP-40). After incubation with the cell extracts, the agarose samples were washed twice with 500 μl of PBS-NP40 and the proteins associated with the resin were eluted at 92° C. for 2 min in 40 µl of SDS-sample buffer. To ensure that equal amounts of the original peptides were complexed to the agarose, an aliquot extracted in SDS-sample buffer was analyzed by SDS-PAGE and Coomassie staining of a 17% polyacrylamide gel for TBpex14 and intron 8-encoded peptide, and a 10% polyacrylamide gel for p50 herstatin. To analyze receptor binding, an aliquot eluted from the agarose was analyzed as a Western blot using anti-EGFR or anti-p185HER-2.

DETAILED DESCRIPTION OF THE INVENTION

Figure 1:
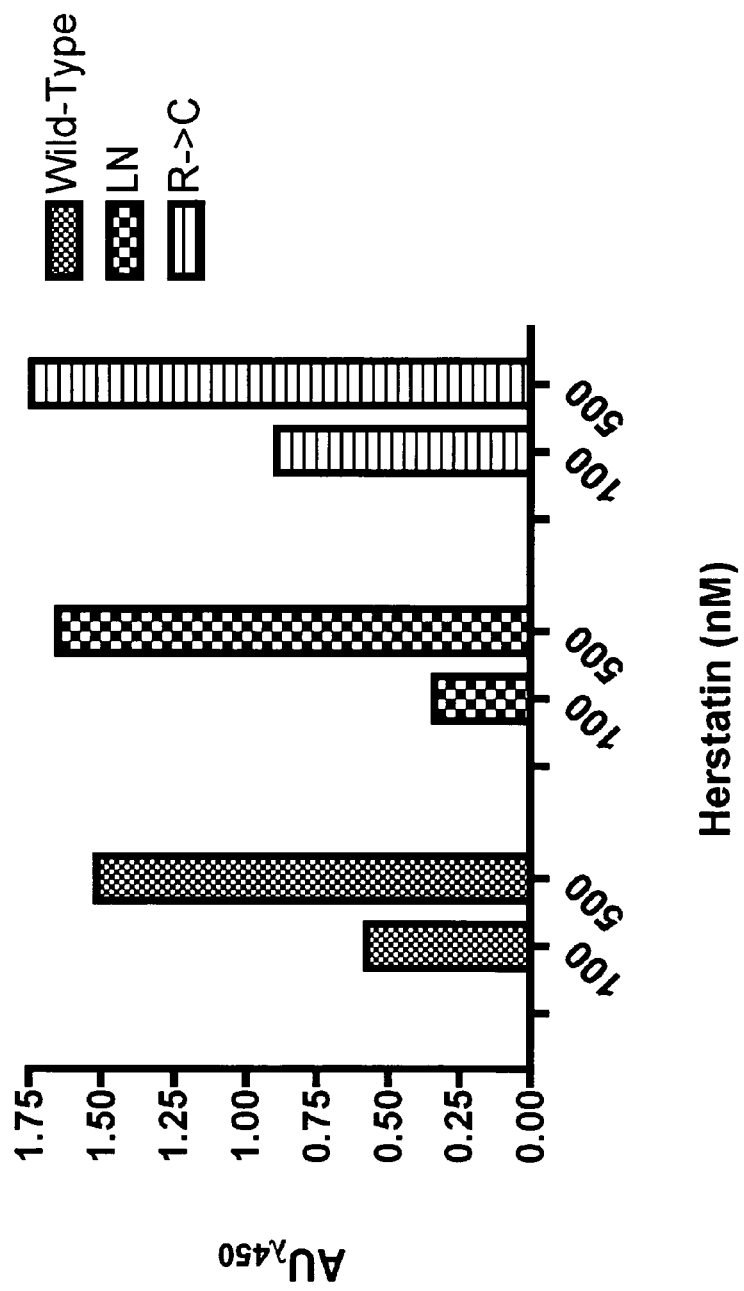
FIG. 1 shows a nucleotide sequence and amino acid of the insert in the extracellular domain of HER-2. The HER-2 ECD coding sequence from exon 1-9 (primers A and B) was amplified by PCR from a cDNA library from SKOV-3 cells. A product of ~1420 bp was found to be HER-2-specific by Southern blot analysis. This product was subcloned and the nucleotide sequence was determined. In panel A, a nucleotide sequence (287 bp: SEQ ID NO:13) is shown for the 275 bp insert (within the open-ended boxes) plus the immediately adjacent 5' and 3' sequences (framed by the open-ended boxes). The 275 bp insert sequence, using the numbering of Coussens et al. (*Science* 230:1132-1139, 1985), is located between nucleotide residues 1171 and 1172 and following amino acid residue 340 in p185HER-2. SEQ ID NO:14 (276 bp) shows the 275 bp insert sequence plus the immediately 5' nucleotide ("G"). The consensus 5' and 3' splice sites at the arrows are shown in larger print. The inserted sequence is in-frame with 5' HER-2 exon sequence and is deduced to encode a 79 amino acid extension (SEQ ID NO:15) following Arg 340 ($R^{340}$). The novel 79 aa sequence (SEQ ID NO:15) encoded by the insert is proline-rich (19%) and has a consensus asparagine linked glycosylation site, which is underlined. A stop codon was found at nucleotides 236-238 within the inserted sequence. In panel B, the predicted product of the alternative transcript is a truncated secreted protein which contains subdomains I and II identical to p185 and is missing the transmembrane domain and cytoplasmic domain. If fully glycosylated, the expected size is 65-70 kDa. This polypeptide product is referred to as p68HER-2. Thus, the product will be a truncated secreted protein which is missing the transmembrane domain and cytoplasmic domain found in p185HER-2.

The present invention is based upon the initial discovery of an alternative HER-2 mRNA of 4.8 kb with a 274 bp insert identified as intron 8. The retained intron is in-frame and encodes 79 amino acids (SEQ ID NO:1) followed by a stop codon at nucleotide 236. The alternative mRNA predicts a truncated HER-2 protein that lacks the transmembrane and intracellular domains and contains 419 amino acids (SEQ ID NO:2); 340 residues that are identical to the N-terminus of p185HER-2 (SEQ ID NO:13) and 79 unique residues at the C-terminus (SEQ ID NO:1). Using specific antibodies against either the novel 79 amino acid residue C-terminal sequence [SEQ ID NO:1] or the N-terminus of p185HER-2, a 68 kDa protein product was identified (SEQ ID NO:2). This 68 kDa protein is the product of an alternative HER-2 transcript, and is found in cell extracts and in extracellular media from several cell lines. Expression of the alternative transcript was highest in a nontransfected human embryonic kidney cell line.

Figure 2:
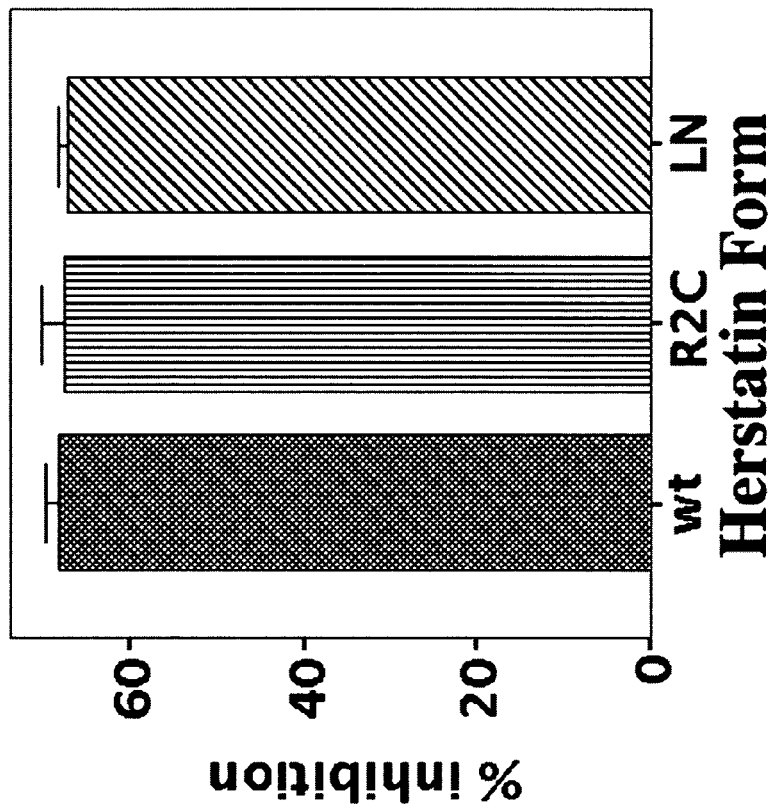
FIG. 2 shows the detection of alternative HER-2 transcripts containing the ECDIIIa sequence by Northern blot analysis. PolyA+ mRNA (2.5 µg) from different human fetal tissues (Clontech) or isolated from HEK-293 cells was resolved in a formalin agarose gel and transferred to a BrightStar® membrane (Ambion) in 10×SSC. The membrane was hybridized with a $^{32}$P-labeled antisense RNA probe complimentary to the ECDIII sequence, stripped and reprobed with a $^{32}$P-labeled cDNA probe specific for the 5' HER-2 exon sequence. The membranes were washed under high stringency conditions and analyzed by phosphorimaging (Molecular Dynamics).
Figure 3:
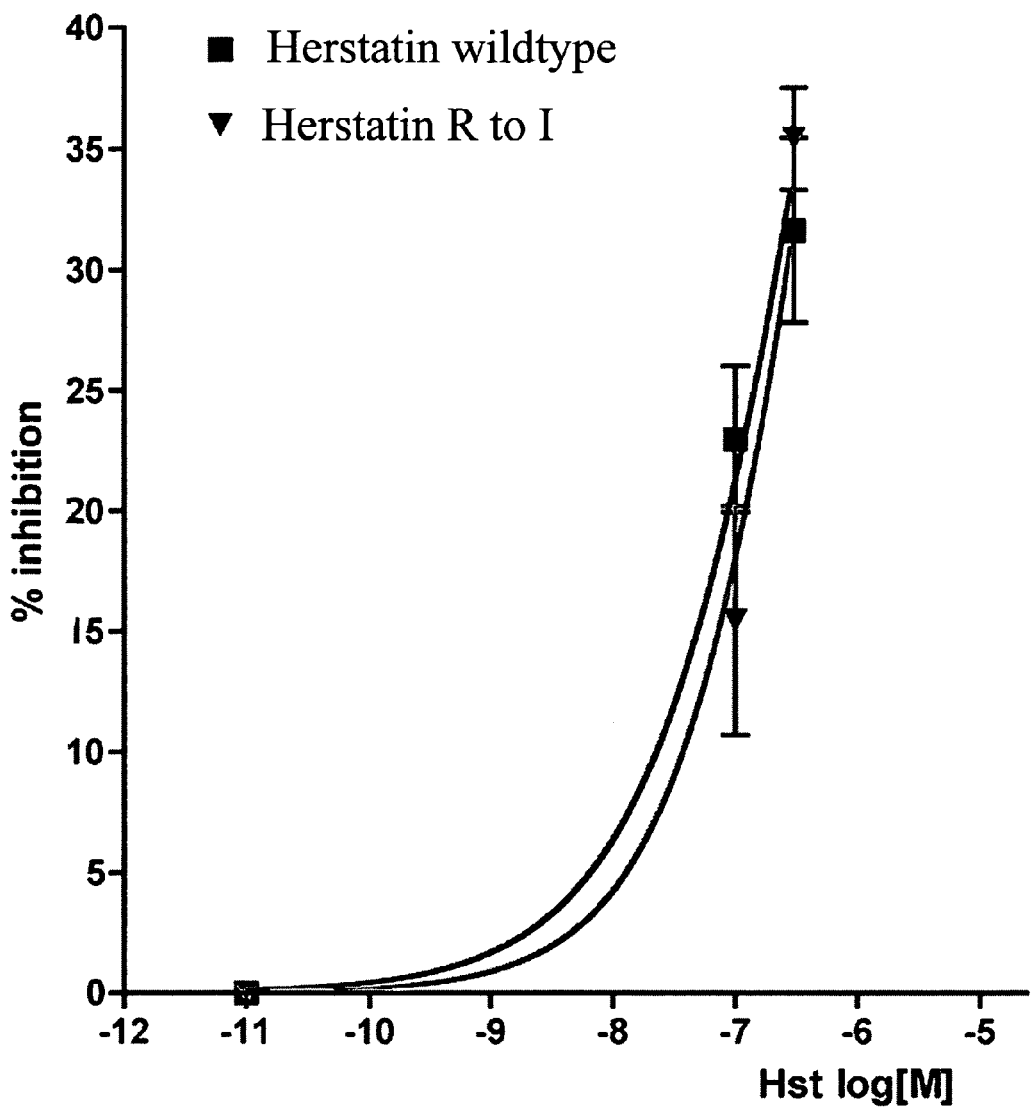
FIG. 3 shows a sequence-specific reactivity of anti-ECDIIIa with a protein of ~68 kDa in a human embryonic kidney cell line (HEK293). Cell extract protein (20 µg) and 20 µl of media conditioned by HEK-293 cells were Western blotted and probed with anti-ECDIIIa diluted 1:10,000 (lanes 1 and 2) or with anti-ECDIIa diluted 1:10,000 containing 50 µg/ml purified His-tagged ECDIIIa peptide (lanes 3, 4).
Figure 5:
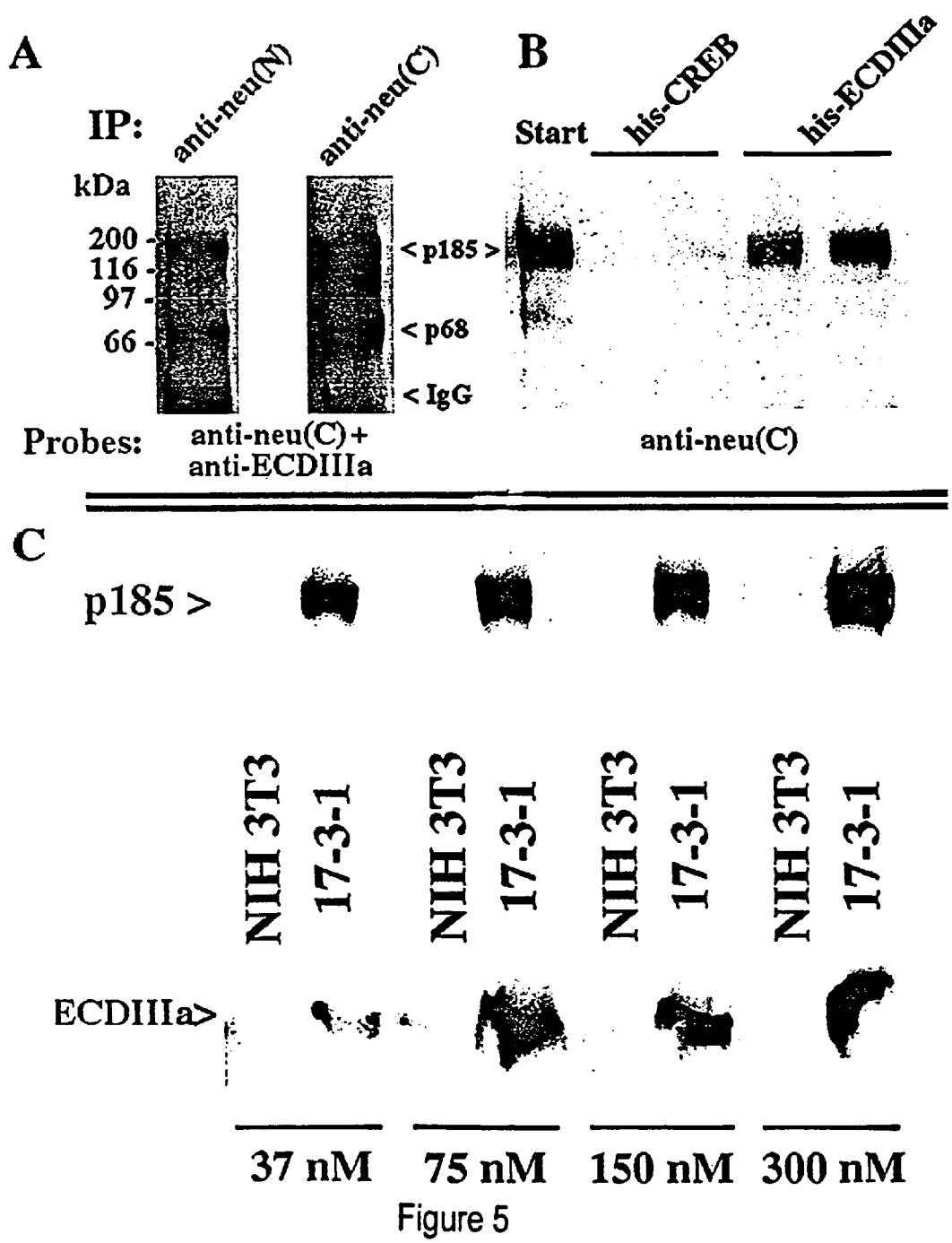
FIG. 5 shows that p68ECDIIIa binds to p185HER-2. In panel A: Two mg of SKBR-3 cells extracted in nondenaturing buffer were immunoprecipitated with 511 anti-neu(N) specific for the N-terminal sequence of p68HER-2 and p185HER-2, or with 5 µl anti-neu(C) specific for the C-terminus of p185HER-2 and then probed as a Western blot with both anti-ECDIIIa specific for p68HER-2 and with anti-neu (C) specific for p185HER-2. In panel B: 100 µg of 17-3-1 cell extract were incubated in duplicate with 50 µl packed volume of NiNTA agarose (Qiagen) coupled to 20 µg of His-tagged ECDIIIa or to 20 µg His-tagged CREB fragment in 200 µl of wash buffer (20 mM Tris pH 8.0, 300 mM NaCl) at room temperature for 1 hr with shaking. The resin was then washed 4 times with 500 µl of wash buffer and proteins were eluted by incubation with 50 µl SDS-sample buffer at 100° C. for 2 min. Eluted proteins were analyzed by Western blot analysis using antibodies against the C-terminus of p185HER-2, anti-neu (C). In panel C: Monolayers of ~$10^5$ 3T3 cells or HER-2 transfected 17-3-1 cells in 12 well plates were washed twice with PBS and then incubated with 0.5 ml of serum-free media with 1% BSA and 39, 75, 150, and 300 nM of purified recombinant His-tagged ECDIIIa for 2 hrs at 4° C. Cells were washed 1 time in PBS containing 1% BSA and twice in PBS and then were extracted in denaturing buffer. Equal aliquots (20 µg protein) were analyzed by western blotting with antibodies specific for ECDIIIa (anti-ECDIIIa) or, in the upper panel, with antibodies specific for p185HER-2 (anti-neu(C)).

The results presented here show expression of alternative HER-2 mRNA, which contains an additional 274 nucleotides, probably intron 8. Consistent with this finding, an alternative transcript of ~4.8 kb was detected in human fetal kidney tissue and in the human embryonic kidney cell line, HEK 293. Moreover, a transcript of 2.6 kb, which is the size expected if the sequence is retained in the 2.3 kb truncated HER-2 mRNA (Yamamoto et al., *Nature* 319:230-234, 1986; and Scott et al., *Mol. Cell. Biol.* 13:2247-2257, 1993), was detected in human fetal liver tissue by Northern blot analysis using a probe specific for the inserted sequence or for the HER-2 ECD coding sequence (FIG. 2). The inserted sequence introduces a termination codon and predicts a novel 79 amino acid extension designated ECDIIIa at residue 340 of the p185HER-2 protein. The predicted protein therefore lacks the transmembrane and intracellular domains, but contains subdomains I and II of the extracellular domain of p185HER-2. As predicted, a secreted protein that contains N-terminal sequence of p185HER-2 and the C-terminal extension provided by the inclusion of the novel sequence was detected (FIGS. 3 and 5). The ECDIIIa protein was found to be 68 kDa which is the approximate size expected of the protein encoded by the alternative transcript if the five N-linked glycosylation sites found in subdomains I and II of p185HER-2 are glycosylated (Stern et al., *Mol. Cell. Biol.* 6:1729-1740, 1986).

The data presented herein demonstrate that p68HER-2 specifically binds to p185HER-2. The association with p185HER-2 may be conferred by the novel proline rich ECDIIIa domain rather than the N-terminal subdomains I and II of p68HER-2. While the HER-2 ECD, generated by in vitro deletion mutagenesis, also contains subdomains I and II, it does not associate with the extracellular domain of p185HER-2 unless engineered to enhance their proximity (Tzahar et al., *EMBO J.* 16:4938-4950, 1997; O'Rourke et al., *Proc. Natl. Acad. Sci. USA* 94:3250-3255, 1997; and Fitzpatrick et al., *FEBS Letters* 431:102-106, 1998). However, the unique ECDIIIa peptide binds with high affinity (nM concentrations) to p185HER-2 and to transfected 17-3-1 cells that overexpress p185HER-2 (FIG. 5). Preferential binding of the ECDIIIa domain peptide to 17-3-1 cells indicates that secreted p68HER-2 interacts with the extracellular region of p185HER-2 at the cell surface. Therefore, p68HER-2 and fragments thereof appear to be a naturally occurring HER-2 binding protein, encoded by the HER-2 gene. In contrast to EGFR family ligands (Groenen et al., *Growth Factors* 11:235-257, 1994), p68HER-2 lacks an EGF homology domain and contains the first 340 amino acids of the receptor itself, p185HER.

Previously described putative HER-2 ligands were found to associate indirectly with p185HER-2 only in a heterodimer with an EGFR family member (Heldin and Ostman, *Cytokine Growth Factor Rev.* 7:33-40, 1996). Although it is possible that ECDIIIa binds indirectly to p185HER-2 through a coreceptor, this seems unlikely since detergent solubilized p185HER-2 was specifically and efficiently "pulled down" by immobilized ECDIIIa peptide (FIG. 5B).

For all naturally occurring or engineered ligands for mammalian EGFR family members, binding is tightly coupled to stimulation of receptor dimerization and tyrosine phosphorylation (Hynes and Stern, *Biochim. et Biophys. Acta* 1198:165-184, 1994; Dougall et al., *Oncogene* 9:2109-2123, 1994; and Groenen et al., *Growth Factors* 11:235-257, 1994). Although they bind, neither p68HER-2 nor the ECDIIIa peptide was found to activate p185HER-2. Activation was assessed in two different cell lines that differ in the extent of p185HER-2 tyrosine phosphorylation, transfected 17-3-1 cells as well as SKOV-3 ovarian carcinoma cells. Furthermore in vitro self-phosphorylation activity, which is enhanced in dimeric forms of p185HER-2 (Dougall et al., *Oncogene* 9:2109-2123, 1994; and Lin et al., *J. Cell. Biochem.* 49, 290-295, 1992), was not stimulated by p68HER-2 or ECDIIIa. Similarly, the Argos protein, which is an extracellular inhibitor of the *Drosophila* EGF receptor and the only known antagonist of class I RTKs, did not simulate tyrosine phosphorylation of the receptor (Schweitzer et al., *Nature* 376:699-702, 1995). Likewise, Angiopoietin-2, a natural antagonist for the Tie 2 RTK, bound the endothelial receptor but failed to activate it (Maisonpierre et al., *Science* 277:55-60, 1997).

Without being bound by theory, since p68HER-2 occupies but does not activate, it could block dimerization of p185HR-2. By analogy, HER-2 ECD, when engineered to enhance its binding to RTKs, prevented the formation of productive dimers required for transphosphorylation and receptor activation thereby having a dominant negative effect (O'Rourke et al., *Proc. Natl. Acad. Sci. USA* 94:3250-3255, 1997). In contrast to the HER-2 ECD, soluble p68HER-2 exhibited strong binding to p185HER-2, yet also contains subdomain I and II of the ECD. Since subdomain I may be the low affinity, promiscuous ligand binding site required for recruitment of p185HER-2 into heteromeric complexes (Tzahar et al., *EMBO J.* 16:4938-4950, 1997), p68HER-2 could block this site and thereby obstruct recruitment of p185HER-2 into dimers. Alternatively, p68HER-2 could compete with an uncharacterized ligand for binding to p185HER-2. The tissue-specific expression of p68HER-2 in human fetal liver and kidney may function to modulate the extent to which p185HER-2 is occupied during development of these organs. Moreover, the overexpression of p185HER-2, relative to p68HER-2 in tumor cells with HER-2 gene amplification (FIG. 3), could occur though a selective pressure based on overcoming the effects of a binding protein such as p68HER-2. Therefore, p68HER-2 is the first example of a naturally occurring p185HER-2 binding protein that may prevent activation of p185HER-2.

Pharmaceutical Composition

The present invention further provides a pharmaceutical composition for treating solid tumors that overexpress HER-2, comprising an agent selected from the group consisting of (a) an isolated polypeptide having from about 50 to 79 amino acids taken from the sequence of SEQ ID NO. 1, wherein the polypeptide binds to the extracellular domain ECD of HER-2 with an affinity binding constant of at least $10^8$ $M^{-1}$ at an affinity of at least 110, (b) an isolated and glycosylated polypeptide having from about 80 to 419. or about 300 to 419 amino acids taken from the sequence of SEQ ID NO. 2, wherein the C terminal 79 amino acids are present, and wherein at least three N-linked glycosylation sites are present, (c) a monoclonal antibody that binds to the ECD of HER-2, and (d) combinations thereof, with the proviso that the agent cannot be the monoclonal antibody alone, and pharmaceutically acceptable carrier. Preferably, the agent is the isolated polypeptide having from about 50 to 79 amino acids taken from the sequence of SEQ ID NO. 1. Most preferably, the agent is a combination of the isolated polypeptide having from about 50 to 79 amino acids taken from the sequence of SEQ ID NO. 1 and the monoclonal antibody that binds to the ECD of HER-2.

The inventive pharmaceutical composition, comprising either or both of the inventive polypeptides and/or monoclonal antibody, can be administered to a patient either by itself (complex or combination) or in pharmaceutical compositions where it is mixed with suitable carriers and excipients. Inventive polypeptide can be administered parenterally, such as by intravenous injection or infusion, intraperitoneal injection, subcutaneous injection, or intramuscular injection. Inventive polypeptide can be administered orally or rectally through appropriate formulation with carriers and excipients to form tablets, pills, capsules, liquids, gels, syrups, slurries, suspensions and the like. Inventive polypeptide can be administered topically, such as by skin patch, to achieve consistent systemic levels of active agent. Inventive polypeptide is formulated into topical creams, skin or mucosal patch, liquids or gels suitable to topical application to skin or mucosal membrane surfaces. Inventive polypeptide can be administered by inhaler to the respiratory tract for local or systemic treatment of cancers characterized by overexpressing HER-2.

The dosage of inventive polypeptide suitable for use with the present invention can be determined by those skilled in the art from this disclosure. Inventive polypeptide will contain an effective dosage (depending upon the route of administration and pharmacokinetics of the active agent) of inventive polypeptide and suitable pharmaceutical carriers and excipients, which are suitable for the particular route of administration of the formulation (i.e., oral, parenteral, topical or by inhalation). The active inventive polypeptide is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the inventive polypeptide in water-soluble form. Additionally, suspensions of the inventive polypeptide may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

Pharmaceutical formulations for oral administration can be obtained by combining the active compound with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelaten, gums, or polyvinylpyrrolidone. In addition, a desintegrating agent may be added, and a stabilizer may be added.

Processes for Synthesizing p68 and 79 aa C Terminal Region

Polypeptide synthesis is done by a group of standard procedures for polypeptide synthesis by sequential amino acids building through peptide synthesis equipment, following manufacturer's instructions for synthesizing peptides. Preferably, shorter polypeptides, of less than 100 amino acids, are best suited for the method of synthesis through sequential amino acid building of polypeptides. In addition, heterologous polypeptides can be expressed by transformed cells using standard recombinant DNA techniques to transform either prokaryotic or eukaryotic cells, provide appropriate growth media for their expression, and then purify the inventive polypeptide either from the media or from intracellular contents depending upon the type of cell used and its expression characteristics.

Methods for Treating Cancer with p68, 79 aa C Terminal Region, and Combinations The present invention provides a method for treating a solid tumor characterized by overexpression of HER-2, or HER-2 variants (see Example 8) comprising administering an agent that binds to the extracellular domain (ECD) of HER-2, wherein the agent is selected from the group consisting of (a) an isolated polypeptide having from about 50 to 79 amino acids taken from the sequence of SEQ ID NO. 1, wherein the polypeptide binds to the extracellular domain ECD of HER-2 with an affinity binding constant of at least $10^8$ $M^{-1}$, (b) an isolated and glycosylated polypeptide having from about 80 to 419. or about 300 to 419 amino acids taken from the sequence of SEQ ID NO. 2, wherein the C terminal 79 amino acids are present, and wherein at least three N-linked glycosylation sites are present, (c) a monoclonal antibody that binds to the ECD of HER-2, and (d) combinations thereof, with the proviso that the agent cannot be the monoclonal antibody alone. Preferably, the solid tumor that overexpresses HER-2 is selected from the group consisting of breast cancer, small cell lung carcinoma, ovarian cancer, prostate cancer, gastric carcinoma, cervical cancer, esophageal carcinoma, and colon cancer. Preferably, the agent is the isolated polypeptide having from about 50 to 79 amino acids taken from the sequence of SEQ ID NO. 1. Most preferably, the agent is a combination of the isolated polypeptide having from about 50 to 79 amino acids taken from the sequence of SEQ ID NO. 1 and the monoclonal antibody that binds to the ECD of HER-2.

The p68HER-2 polypeptide described herein was found to bind to HER-2 and prevent signal transduction through the kinase domain. Without being bound by theory, the unique ECDIIIa domain mediates specific binding to p185HER-2 and the resulting interaction with p68ECDIIIa prevents p185HER-2 dimerization and subsequent signal transduction. Therefore, p68HER-2 functions as a HER-2 antagonist to prevent signal transduction by preventing dimerization as a necessary prerequisite for signal transduction. Thus, the mechanism of p68HER-2 as a HER-2 antagonist is different from the mechanism of binding agents, such as the 79 amino acid polypeptide described herein or a monoclonal antibody that binds to the EDC of HER-2. The inventive method provides that p68HER-2 inhibits tumor cell growth in tumors that overexpress HER-2 by providing a selective pressure for such tumor cells. Similarly, the HER-2 antagonists that are binding agents also inhibit tumor cell growth in tumors that overexpress HER-2 by providing selective pressure to such cells to prevent ligand binding to the ECD of HER-2 and prevent signal transduction even before potential dimerization.

Use of 79 aa C Terminal Region as a Targeting Molecule

The present invention further provides a method for targeting a therapeutic agent to solid tumor tissue, wherein the solid tumor tissue is characterized by overexpression of HER-2, comprising attaching the therapeutic agent to an isolated polypeptide having from about 50 to 79 amino acids taken from the sequence of SEQ ID NO. 1, wherein the polypeptide binds to the extracellular domain ECD of HER-2 with an affinity binding constant of at least $10^8$ $M^{-1}$. Preferably, the isolated polypeptide is from about 69 to 79 amino acids in length. Preferably, the isolated polypeptide binds to a site on the ECD of HER-2 that is different from the site of binding of HERCEPTIN® (a marketed humanized monoclonal antibody that is used for the treatment of cancer and that binds to the ECD or HER-2). It was discovered that the 79 amino acid polypeptide [SEQ ID NO. 1] exhibited surprising high affinity binding properties to the ECD of HER-2. Moreover, the site of such binding is different and unaffected by the site of binding of a marketed humanized monoclonal antibody (HERCEPTIN®). Therefore, the high binding affinity enables the 79 amino acid polypeptide to function as a targeting molecule to tumor cells expressing HER-2.

Anti-p68 Antibody as a Diagnostic/Prognostic Agent

The p68HER-2 ECDIIIa variant 3 (see TABLE 1, below) glycosylated polypeptide was expressed and used as an antigen for antibody production. Specifically, antibody specific for p68HER-2 was prepared by injecting rabbits with purified polyhistidine-tagged ECDIIIa variant 3 peptide, which is the same as the intron encoded novel C-terminus or p68HER-2, the domain that binds with high affinity to p185HER-2. The isolated polyclonal antibody detected pM quantities of ECDIIIa peptide or of p68HER-2 with high specificity (see FIGS. 3 and 5). Thus, an antibody specific for p68HER-2 is useful as a diagnostic agent for detecting p68HER-2 in bodily fluids and tumor tissues using diagnostic techniques, such as ELISA, immunoprecipitations, immunohistochemistry or Western analysis.

Antibodies that specifically recognize one or more epitopes of ECDIIIa, or epitopes of p68HER-2, or peptide fragments, and thus distinguish among ECDIIIa variants (see TABLE 1, below) are also encompassed by the invention. Such antibodies include but are not limited to polyclonal antibodies, monoclonal antibodies (mAbs), humanized or chimeric antibodies, single-chain antibodies, Fab fragments, F(ab').sub.2 fragments, fragments produced by a Fab expression library, anti-idiotypic (anti-Id) antibodies, and epitope-binding fragments of any of the above. The antibodies of the invention may be used, for example, in the detection of a particular p68HER-2 ECDIIIa variant in a biological sample and may, therefore, be utilized as part of a diagnostic or prognostic technique whereby patients or tissue samples may be tested for the presence of particular variants, or for abnormal amounts particular variants.

Such antibodies may also be utilized in conjunction with, for example, compound screening schemes for the evaluation of the effect of test compounds on expression and/or activity of particular p69HER-2 variants. Additionally, such antibodies can be used in conjunction with the cancer treatment methods described herein.

For the production of antibodies, various host animals may be immunized by injection with e.g., polyhistidine-tagged ECDIIIa variant polypeptides, truncated ECDIIIa variant polypeptides, functional equivalents of the ECDIIIa variants or mutants of the ECDIIIa region. Such host animals may include but are not limited to rabbits, mice, hamsters and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of the immunized animals. Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (Nature 256:495-497, 1975; and U.S. Pat. No. 4,376,110), the human B-cell hybridoma technique (Kosbor et al., Immunology Today 4:72, 1983; Cole et al., Proc. Natl. Acad. Sci. USA 80:2026-2030, 1983), and the EBV-hybridoma technique (Cole et al., Monoclonal Antibodies And Cancer Therapy, Alan R. Liss, Inc., pp. 77-96, 1985). Such antibodies may be of any immunoglobulin class including IgG, IgM, IgE, IgA, IgD and any subclass thereof. Hybridomas producing mAb may be cultivated in vitro or in vivo. Production of high titers of mAbs in vivo makes this the presently preferred method of production.

Additionally, techniques developed for the production of "chimeric antibodies" (Morrison et al., Proc. Natl. Acad. Sci. USA, 81:6851-6855, 1984; Neuberger et al., Nature, 312: 604-608, 1984; Takeda et al., Nature, 314: 452-454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region (humanized).

Alternatively, techniques described for the production of single-chain antibodies (U.S. Pat. No. 4,946,778; Bird, Science 242:423-426, 1988; Huston et al., Proc. Natl. Acad. Sci. USA 85:5879-5883, 1988; and Ward et al., Nature 334:544-546, 1989) can be adapted to produce single-chain antibodies against ECDIIIa variant gene products. Single-chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab').sub.2 fragments which can be produced by pepsin digestion of the antibody molecule and the Fab fragments which can be generated by reducing the disulfide bridges of the F(ab').sub.2 fragments. Alternatively, Fab expression libraries may be constructed (Huse et al., Science, 246:1275-1281, 1989) to allow rapid and easy identification of monoclonal Fab fragments with the desired specificity.

Antibodies to particular ECDIIIa variants can, in turn, be utilized to generate anti-idiotype antibodies that "mimic" the ECDIIIa variant, using techniques well known to those skilled in the art. (Greenspan & Bona, FASEB J 7 (5):437-

444, 1993; and Nissinoff, J. Immunol. 147:2429-2438, 1991). For example antibodies which bind to an ECDIIIa variant and competitively inhibit the binding of p68HER-2 to HER-2 receptor can be used to generate anti-idiotypes that "mimic" the ECDIIIa variant and, therefore, bind and neutralize HER-2 receptor. Such neutralizing anti-idiotypes or Fab fragments of such anti-idiotypes can be used in cancer therapeutic regimens.

Alternatively, antibodies to particular ECDIIIa variants that can act as agonists or antagonists of the ECDIIIa variant activity can be generated. Such antibodies will bind to the ECDIIIa variant and modulate the activity of p68HER-2 vis-à-vis p185HER-2 receptor-mediated signal transduction. Such antibodies may be particularly useful for treating particular cancers and/or modulating tumor differentiation. Accordingly, the present invention further provides a method for determining the prognosis of tumor treatment for a tumor that overexpresses HER-2, comprising: (a) obtaining a bodily fluid, wherein the bodily fluid is selected from the group consisting of blood, serum, urine, lymph, saliva, tumor tissue, and combinations thereof; and (b) measuring the amount of p68HER-2 expressed using an anti-p68HER-2 antibody-based assay, wherein the assay is selected from the group consisting of ELISA, immunoprecipitation, immunohistocytochemistry, and Western analysis. Preferably, the method for determining the prognosis of tumor treatment further comprises measuring the amount of p185HER-2 ECD in the bodily fluid, and determining a ratio between the amount of p68HER-2 and p185HER-2. The higher the ratio of p68HER-2:p185HER-2, the better the treatment prognosis.

ECDIIIa Region Variants as Diagnostic/Prognostic Agents

Example 11 (below) shows that the human sequence of intron 8 is both proline-rich and polymorphic. Sequencing of genomic DNA from fifteen different individuals resulted in the identification of 10 variable sequence regions within Her-2 Intron 8. See SEQ ID NO:10; FIG. 8, and Table 1. FIG. 8 shows the most common nucleotide and corresponding polypeptide sequences of intron 8. This region contains 10 different polymorphisms (marked by the letters W (2×), Y (3×), R, N, M (2×), and S (1×) in SEQ ID NO:10; or marked by an "X" in FIG. 8) that result in nonconservative amino acid substitutions (see legend to TABLE 1). For example, the polymorphism (C→G) at nucleotide position 161 (FIG. 8; TABLE 1) would result in a substitution of Arginine (R) for Proline (P) at amino acid residue #54 of SEQ ID NO:1, or residue #394 of SEQ ID NO:2. The N-terminal Glycine (G), designated as position 1 in FIG. 8 or SEQ ID NO:10, corresponds to amino acid residue 341 in the "herstatin" sequence (Doherty et al., Proc. Natl. Acad. Sci. USA 96:10,869-10,874, 1999). The nucleotide sequence shown in FIG. 1(A) (Doherty et al., Proc. Natl. Acad. Sci. USA 96:10,869-10,874, 1999), is a polymorphic form that differs at amino acid residues #6 and #73 from the most commonly detected sequence shown here in FIG. 8.

This result demonstrates that in the human population there are several variations in the intron-8 encoded domain that could lead to altered biochemical and biological properties among ECDIIIa-containing protein variants. An individual may, inter alia, be genetically heterozygous for two variants, homozygous for a given variant, or homozygous for a double variant. Both tumor progression and optimal treatment may vary depending upon the particular variants represented in a given individual.

This variability has both prognostic and diagnostic utility. The present invention shows that ECDIIIa-containing polypeptides can bind tightly to, and thus antagonize the HER-2 receptor. Such a specific, high-affinity interaction is dependent upon particular primary, secondary and tertiary structure of the ECDIIIa-containing polypeptide. The ECDIIIa region is proline-rich, and it is well known in the art that nonconservative substitution of proline residues, or other residues within a proline-rich sequence, in a given protein can have profound effects on its secondary and tertiary structure. Thus, the polymorphisms of the present invention are likely to embody significant structural, biochemical and biological differences relative to the most common polypeptide structure (shown in FIG. 8). Structural differences among ECDIIIa variant proteins may include for example, differences in size, electronegativity, or antigenicity. Differences in biological properties among ECDIIIa variants might be seen e.g., in the relative degree of cellular secretion, the nature and/or extent of modulation of the HER-2 receptor, pharmacokinetics (e.g., serum half-life, elimination profile), resistance to proteolysis, N-linked glycosylation patterns, etc. These biological differences, in turn, would be expected to alter tumor progression and thus optimal treatment protocols. Thus, the knowledge that an individual contains a particular ECDIIIa variant or variants (e.g., in individuals heterozygous for a given variant, or individuals with compound variants like variant 11 of Table 1), may, in itself, be prognostic of particular cancer susceptibility.

The apparent genetic heterogeneity of ECDIIIa region means that the nature of the particular ECDIIIa variation carried by an individual may have to be ascertained using sequence identity assays prior to attempting genetic diagnosis of the patient. The analysis can be carried out on any genomic DNA derived from bodily fluids of the patient, typically a blood sample from an adult or child, but alternatively may be serum, urine, lymph, saliva, tumor tissue, placental tissue, umbilical cord tissue, amniotic fluid, and chorionic villi samples. It is expected that standard genetic diagnostic methods, such as hybridization or amplification assays, can be used. Either DNA or RNA, may, for example, be used in hybridization or amplification assays of biological samples to detect particular ECDIIIa variant sequences. Such sequence identity assays may include, but are not limited to, Southern or Northern analyses, single-stranded conformational polymorphism analysis, in situ hybridization assays, and polymerase chain reaction ("PCR") analyses. Such analyses may reveal both quantitative and qualitative aspects of ECDIIIa variant sequence expression. Such aspects may include, for example, point mutations, and/or activation or inactivation of gene expression. Standard in situ hybridization techniques may be used to provide information regarding which cells within a given tissue express a particular ECDIIIa variant sequence.

Preferably, diagnostic methods for the detection of ECDIIIa variant nucleic acid molecules involve contacting and incubating nucleic acids, derived from cell types or tissues being analyzed, with one or more labeled nucleic acid reagents, or probes, specific for particular ECDIIIa variants. More preferably, PCR, or reverse transcription PCR, can be utilized to identify nucleotide variation within the ECDIIIa domain. PCR reaction conditions should be chosen which optimize amplified product yield and specificity, and, additionally, produce amplified products of lengths that may be resolved utilizing standard gel electrophoresis techniques. Such reaction conditions are well known to those of skill in the art, and important reaction parameters include, for example, length and nucleotide sequence of oligonucleotide primers, and annealing and elongation step temperatures and reaction times. Following the PCR reaction, the PCR products can be analyzed by methods such as heteroduplex detection, cleavage of RNA-DNA hybrids using Rnase A, single-stranded conformational polymorphisms, and denaturing gradient gel electrophoresis.

Additionally, if the particular ECDIIIA sequence variant is known to add or remove a restriction site, or to have significantly altered the size of a particular restriction fragment, a protocol based upon restriction fragment length polymorphism ("RFLP") analysis may be appropriate.

ECDIIIa variants can also be analyzed at the expression level using sequence identity assays with bodily fluids derived from the patient, typically a blood sample from an adult or child, but may include serum, urine, lymph, saliva, tumor tissue, placental or umbilical cord cells, amniotic fluid, and chorionic villi samples. Well-known sequence identity assays for analyzing expression include, but are not limited to, mRNA-based methods, such as Northern blots and in situ hybridization (using a nucleic acid probe derived from the relevant cDNA), and quantitative PCR (as described by St-Jacques et al., Endocrinology 134:2645-2657, 1994).

Polypeptide-based methods (e.g., including but not limited to western blot analysis) including the use of antibodies specific for the ECDIIIa variant of interest, as discussed above, could also be used. These techniques permit quantitation of the amount of expression of a given ECDIIIa variant, at least relative to positive and negative controls. Preferably, a battery of monoclonal antibodies, specific for different ECDIIIa epitopes or variants, could be used for rapidly screening cells or tissue samples to detect those expressing particular ECDIIIa variants, or for quantifying the level of ECDIIIa variant polypeptides. Preferred diagnostic methods for the quantitative or qualitative detection of ECDIIIa variant peptide molecules may involve, for example, immunoassays wherein particular ECDIIIa-containing peptides are detected by their interaction with anti-ECDIIIa variant specific antibodies. This can be accomplished for example, by immunofluorescence techniques employing a fluorescently labeled antibody coupled with light microscopic, flow cytometric, or fluorometric detection. The antibodies (or fragments thereof) useful in the present invention may, additionally, be employed histologically, as in immunofluorescence or immunoelectron microscopy, for in situ detection of ECDIIIa-containing peptides. Through the use of such procedures, it is possible to determine not only the presence of particular ECDIIIa-containing polypeptides, but also their distribution in the examined tissue.

Immunoassays for ECDIIIa variant polypeptides preferably comprise incubating a biological sample, such as the above-named bodily fluids, which have been incubated in the presence of a detectably labeled antibody capable of identifying ECDIIIa-containing peptides, and detecting bound antibody by any of a number of techniques well known in the art. The biological sample may be brought in contact with and immobilized onto a solid phase support or carrier such as nitrocellulose, or other solid support that is capable of immobilizing soluble proteins, cells, or cell particles. The support may then be washed with suitable buffers followed by treatment with the detectably labeled anti-ECDIIIa variant specific antibody. The solid phase support may then be washed with the buffer a second time to remove unbound antibody. The amount of bound label on the solid support may then be detected by conventional means.

Alternatively, anti-ECDIIIa variant specific antibodies can be detectably labeled by linking the same to an enzyme for use in an enzyme immunoassay or Enzyme Linked Immunosorbent Assay ("ELISA"). The enzyme which is bound to the antibody will react with an appropriate substrate, preferably, a chromogenic substrate, in such a manner as to produce a chemical moiety which can be detected, for example, by spectrophotometric, fluorimetirc or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

The detection can be accomplished by calorimetric methods that employ a chromogenic substrate for the enzyme. Detection may also be accomplished visually by comparison of the extent of enzymatic reaction with appropriate standards. Detection may also be accomplished using any of a variety of other immunoassays. For example, by radioactively labeling the antibodies or antibody fragments, it is possible to detect ECDIIIa-containing peptides through the use of a radioimmunoassay (RIA). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The binding activity of a given lot of anti-ECDIIIa-variant specific antibody may be determined according to well-known methods. Those skilled in the art will be able to determine operative and optimal assay conditions for each determination by employing routine experimentation.

Accordingly, the present invention, including the unexpected discovery of a plurality of variable sequence positions within the proline-rich ECDIIIa region, along with antibodies specific for particular ECDIIIa variants, provides for valuable prognostic and diagnostic information and assays.

Accordingly, the present invention further provides a method for determining the prognosis of tumor treatment in a patient for a tumor that overexpresses HER-2, comprising: (a) obtaining a bodily fluid sample from the patient, wherein the bodily fluid is selected from the group consisting of blood, serum, urine, lymph, saliva, tumor tissue, placental tissue, umbilical cord tissue, amniotic fluid, chorionic villi tissue, and combinations thereof; and (b) measuring the amount of p68HER-2 expressed using an anti-p68HER-2 antibody-based assay, wherein the assay is selected from the group consisting of ELISA, immunoprecipitation, immunohistocytochemistry, and Western analysis. Preferably, the method for determining the prognosis of tumor treatment further comprises measuring the amount of p185HER-2 ECD in the bodily fluid, and determining a ratio between the amount of p68HER-2 and p185HER-2. The higher the ratio of p68HER-2:p185HER-2, the better the treatment prognosis. Preferably, the method for determining the prognosis of tumor treatment further comprises determining which particular ECDIIIa variants are present and optimizing tumor treatment in view of particular biochemical and biological properties among ECDIIIa protein variants.

The present invention further provides an assay for cancer treatment, prognosis or diagnosis in a patient comprising: (a) obtaining a bodily fluid sample from the patient, wherein the bodily fluid is selected from the group consisting of blood, serum, urine, lymph, saliva, tumor tissue, placental tissue, umbilical cord tissue, amniotic fluid, chorionic villi tissue and combinations thereof; (b) determining whether a particular ECDIIIa variant sequence is present in the bodily fluid sample with a sequence identity assay; and (c) correlating the presence of the ECDIIIa variant sequence to cancer treatment and diagnosis using an historical database. Preferably, the sequence identity assay is selected from the group consisting of DNA sequencing, PCR assays, ELISA immunologic assays, immunoassays, hybridization assays, and combinations thereof.

The present invention further provides an assay for cancer treatment, prognosis or diagnosis in a patient comprising: (a) obtaining a bodily fluid sample from the patient, wherein the bodily fluid is selected from the group consisting of blood, serum, urine, lymph, saliva, tumor tissue, placental tissue, umbilical cord tissue, amniotic fluid, chorionic villi tissue and combinations thereof; (b) determining whether an amount of an p68HER-2 ECDIIIa variant is present in the bodily fluid sample using an anti-p68HER-2 antibody-based assay, wherein the assay is selected from the group consisting of ELISA, immunoprecipitation, immunohistocytochemistry, and Western analysis; and (c) correlating the presence or amount of the p68HER-2 ECDIIIa variant to cancer treatment and diagnosis using an historical database.

The present invention further provides for the above-mentioned cancer treatment, prognostic or diagnostic assays, further comprising measuring the amount of p185HER-2 ECD in the bodily fluid sample.

The present invention further provides for the above-mentioned cancer treatment, prognostic or diagnostic assays further comprising measuring the amount of p185HER-2 ECD in the bodily fluid sample, and determining a ratio between the amount of p185HER-2 ECD and a particular p68HER-2 ECDIIIa variant.

The present invention further provides for antibodies specific for ECDIIIa variants of the sequence in SEQ ID NO:1 or SEQ ID NO:2, below.

P68HER-2 as a Therapeutic Agent

Without being bound by theory, but it appears that p68HER-2 or ECDIIIa peptide inhibits the growth of tumor cells that overexpress HER-2 by binding to p185HER-2 at the cells surface. This hypothesis was examined by testing anchorage independent growth of cells in the presence or absence of p68HER-2 using cells that depend on p185HER-2 overexpression for their malignant growth, yet have little or no detectable p68HER-2. Anchorage independent growth of cells in soft agar was used as a predictive model for tumor cytotoxicity. This is a common and predictive procedure to examine transforming activity and reflects the tumorigenic and oncogenic potential of cells (DiFore et al., Science 237: 178-182, 1987; Hudziak et al., Proc. Natl. Acad. Sci. USA 84:7159-7163, 1987; and Baasner et al., Oncogene 13:901-911, 1996).

Figure 7:
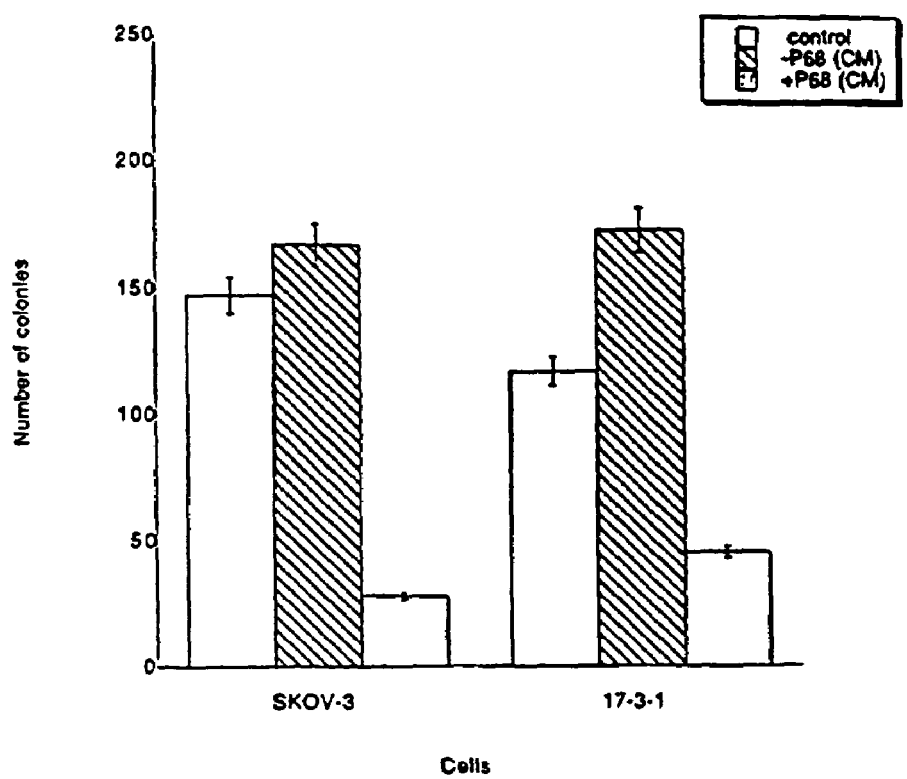
FIG. 7 shows that p68HER-2 inhibited anchorage independent growth of tumorigenic cells. SKOV-3 ovarian cancinoma cells and HER-2 transfected 17-3-1 cells were suspended in media with 10% fetal bovine serum containing 0.3% agar (control conditions) to which was added 50× concentrated media conditioned by SKOV-3 cells (which contains no detectable p68HER-2 (−p68 CM)), or 50× concentrated media conditioned by HEK-293 cells (which contains 20 nM p68HER-2 (+p68 CM)). Five times $10^3$ cells were plated in triplicate for each experimental condition onto a 0.5 ml layer of media containing 0.5% agarose in 12 well plates. The results shown are plotted as the mean and standard deviation of the number of colonies with more than 50 cells in triplicate wells counted at 21 days of incubation. Similar results were observed in three separate experiments.

The effects of p68HER-2 on anchorage independent growth in soft agar was determined using SKOV-3 carcinoma cells and HER-2 transfected 17-3-1 cells, which are both tumorigenic and overexpress p185HER-2. The cells were suspended in media supplemented with fetal calf serum in the presence or absence of p68HER-2 and incubated for 21 days in a humidified incubator. Anchorage independent growth was quantitated by counting the number of colonies that contained more than 50 cells. FIG. 7 shows that in the presence of p68HER-2, anchorage independent growth of both SKOV-3 cells and 17-3-1 cells was inhibited several fold. Accordingly, these data show that p68HER-2 is not just cytostatic, but cytotoxic and possibly apoptotic.

Coexpression of Herstatin Inhibits p185HER-2 Levels and Inhibits Colony Formation.

Figure 9:
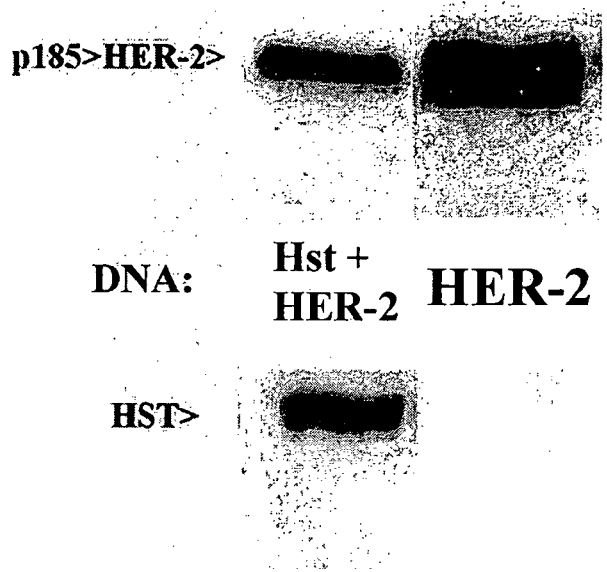
FIGS. 9 and 10 show the Expression of herstatin in combination with p185HER-2 in transfected Cos-7 cells. Cos-7 cells were plated at $2\times10^5$ cell/well into 6 well plates and transfected using Lipofectamine (BioRrad) as described in Materials and Methods. The cells were transfected with 1.5 ug of herstatin expression vector plus 1.5 ug of HER-2 expression vector, or with 1.5 ug of HER-2 expression vectors (all pcDNA3.1 from Invitrogen). In each case the total amount of DNA was adjusted to 3 ug with control empty vector.
Figure 10:
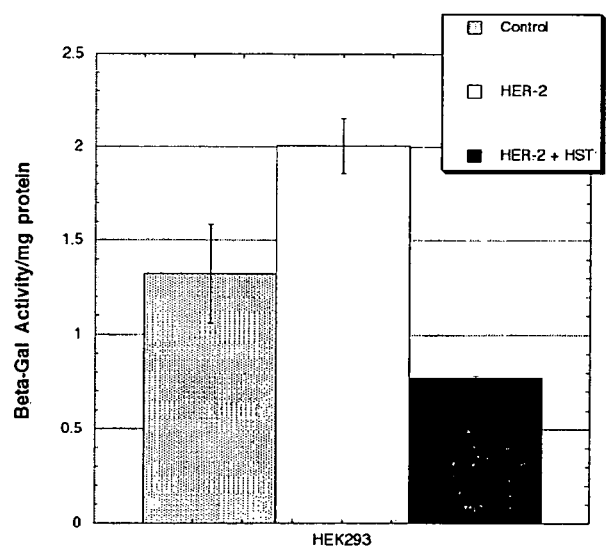

The effects of ectopic herstatin expression on p185HER-2 in transfected Cos-7 cells were examined. S shown in FIG. 9, compared to cells transfected with HER-2 alone, p185 levels were decreased about 5 fold when herstatin was coexpressed. If herstatin expression caused diminished survival of transfected cells, this may explain decreased p185HER-2 levels in the cotransfected cells. Whether expression of the marker-galactosidase plasmid was altered in the cotransfected cells was examined. FIG. 10 illustrates that the -gal activity was greatest when the -gal plasmid was cotransfected with p185HER-2, which was about 35% higher than when cotransfected with control (pcDNA empty plasmid). When cells were cotransfected with herstatin in combination with p185HER-2 and the -gal plasmid, the level of -gal activity was reduced about 3 fold. This reduction was observed in two additional cell lines, CHO and HEK-293. Moreover, a similar level of inhibition was observed when expression of an alternative marker, fluorescent green protein (FGP), was examined in the cells transfected with herstatin and HER-2 (not shown). The results show that transfection with HER-2 alone increased the level of a cotransfected marker, while coexpression with herstatin and HER-2 reduced the marker signal. One possible explanation is that survival of the transfected cells is enhanced by expression of p185HER-2 and is inhibited by coexpression of herstatin and p185HER-2.

Figure 11:
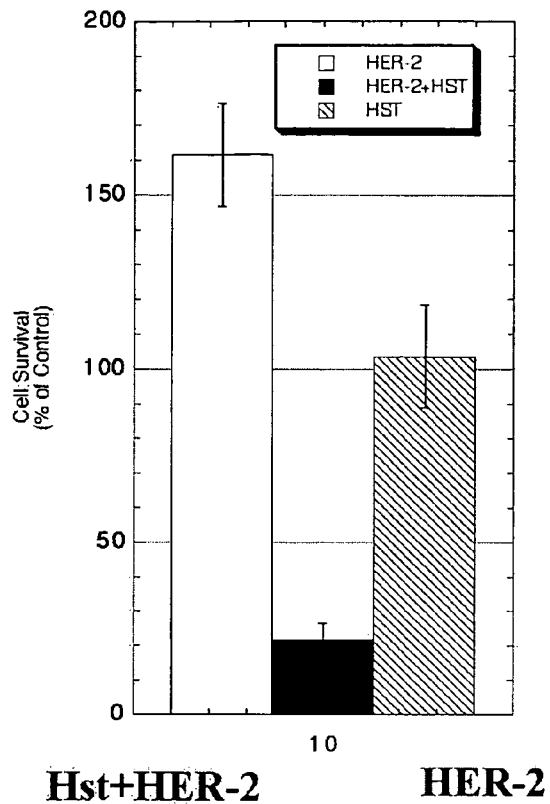
FIGS. 11 and 12 show the effects of herstatin on the growth of transfected cell colonies. CHO cells were seeded at $2\times10^5$ cell/well in 6 well plates and triplicate wells were transfected as described in Materials and Methods with 3 μg of control empty plasmid (pcDNA 3.1; Invitrogen), 1.5 mg of p185HER-2 expression plasmid plus 1.5 μg mg of control DNA; 1.5 μg of p185HER-2 plus 1.5 μg of herstatin; or 1.5 μg of herstatin plus 1.5 μg of control DNA. At 48 hours after addition of DNA, the cells were trypsinized and diluted 1:10 into 6 well plates in the presence of 0.6 mg/ml of G418. The media was changed every two days. At 14 days, the plates were stained with crystal violet and washed. In the upper panel, the crystal violet stained plates were extracted by shaking at room temperature for 30 minutes with 1 ml of 0.1 M NaPhosphate pH 4.5 in 50% ethanol. The extracted crystal violet, diluted 10 fold, was quantitated by the absorbance at 515 nM. Dilutions of 10 fold gave readings of 0.1 to 1.0 which was in the linear range of absorbance versus cell number determined in pilot studies (not shown).
Figure 12:
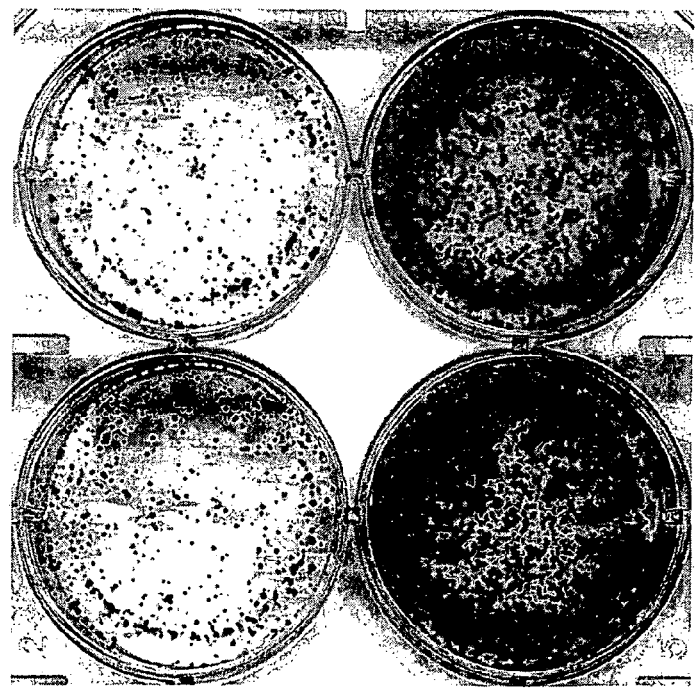

To directly measure effects on colony formation, CHO cells were transfected, subjected to selection with G418 for 20 days, and the surviving cell colonies were stained and quantitated. CHO cells are well suited for rapid growth of stably transfected cells. As shown in FIG. 11, transfection with p185HER-2 enhanced colony growth by about 60% relative to the control transfected cells while herstatin, expressed alone, did not significantly alter growth. However, also as shown in FIG. 11, cotransfection of herstatin dramatically reduced colony formation of HER-2 transfected cells by about 7 fold.

Herstatin Expression Inhibits p185HER-2 Tyrosine Phosphorylation

Figure 13:
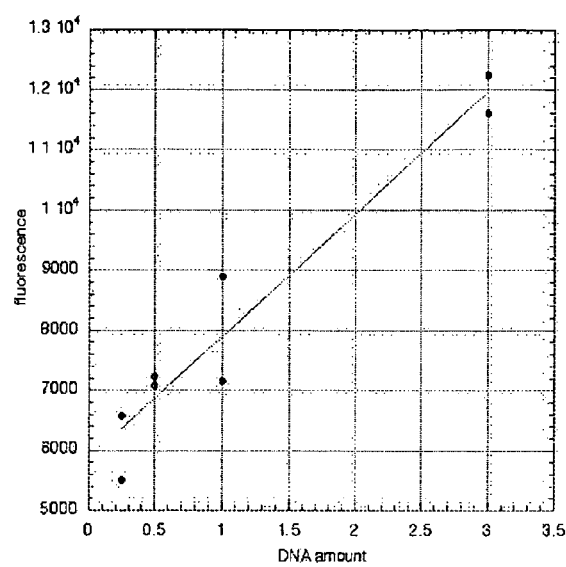
FIGS. 13, 14 and 15 show Herstatin expression inhibits p185HER-2 tyrosine phosphorylation in transfected cells. Cos-7 cells were plated into 6 well plates and transfected as in FIGS. 9 and 10.
Figure 14:
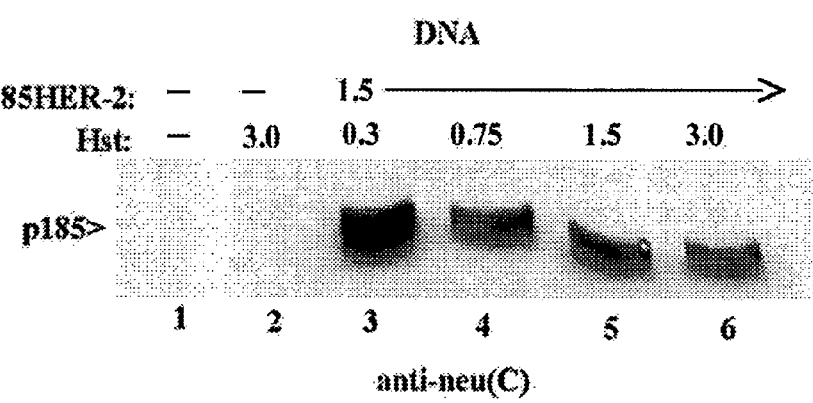
Figure 15:
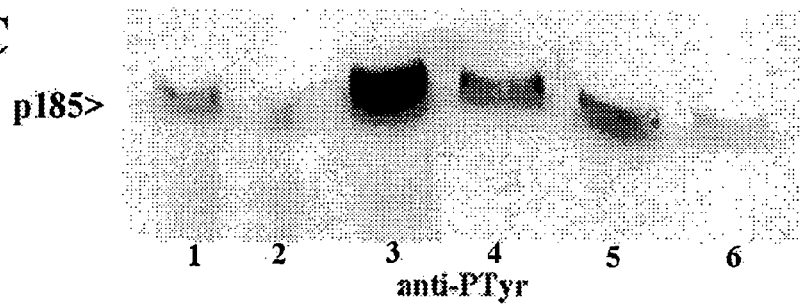

The impact of herstatin expression on p185HER-2 was further evaluated by varying the proportion of herstatin to p185HER-2 expression plasmids. When the herstatin plasmid was introduced at five fold lower levels relative to the p185HER-2 plasmid, there was little effect on p185. As shown in FIG. 14, as the amount of the herstatin plasmid was increased relative to the HER-2 plasmid, p185HER-2 levels were reduced and the expression of cotransfected marker GFP plasmid was reduced as in FIG. 1 (not shown). In contrast, as shown in FIG. 13, transfection with the control GFP expression plasmid alone, which does not affect cell survival, resulted in GFP expression that was proportional to the amount of plasmid added. Therefore, reduced levels of p185 HER-2, detected by Western analysis, appears to be related to diminished survival of the transfected cells. As shown in FIG. 15, panel 6, while there was a three fold reduction in p185HER-2 levels, p185 tyrosine phosphorylation signal was diminished by 25 fold, indicating an approximate 8 fold decrease in the level of tyrosine phosphorylation of p185HER-2. The extent of inhibition of p185 tyrosine phosphorylation was affected by the ratio of herstatin to HER-2 expression plasmid with the strongest effect observed at a ratio of 2 to 1. As sown in FIG. 15, comparing panels 1 and 6, transfection of the herstatin plasmid alone reduced the phosphotyrosine signal associated with an 185 kDa protein by about two fold. The p185 protein comigrated with p185HER-2 expressed from the transfected plasmid and may be endogenous p185HER-2. These results show that ectopic expression of herstatin reduced the tyrosine phosphorylation of exogenous p185HER-2, and that the ratio of herstatin to HER-2 expression plasmids affects the extent of inhibition of p185 HER-2 tyrosine phosphorylation and the level of expression of p185. Further these findings show that reduced p185HER-2 tyrosine phosphorylation correlated with diminished colony formation of cells cotransfected with HER-2 and herstatin.

herstatin expression strongly inhibits colony formation of cells that overexpress p185HER-2. In addition, herstatin suppresses the increased survival provided by overexpression of the EGF receptor. Diminished cell survival corresponds to a reduction in tyrosine phosphorylation of p185HER-2 and to interference with EGF activation of the EGF receptor. further evidence is disclosed of the inhibitory activity against p185HER-2 and extends the negative regulatory activity of herstatin to a second member of the group I family of receptor tyrosine kinases, the EGF receptor.

herstatin inhibits p185HER-2 tyrosine phosphorylation. Transfection of herstatin diminishes the level of constitutive tyrosine phosphorylation of ectopically expressed p185 by 8 fold. this inhibition is observed in transfected CHO cells, HEK-293 cells and Cos-7 cells. The extent of inhibition of p185 tyrosine phosphorylation by herstatin is dose dependent since it is affected by the amount of herstatin relative to HER-2 plasmid added to cells. A suggested model is that herstatin inhibits p185HER-2 receptor tyrosine phosphorylation by preventing receptor dimerization, an obligatory step in receptor transphosphorylation and activation.

Ectopic expression of herstatin also interfered with EGF-activation of the EGF receptor, a group I receptor with homology to p185HER-2. herstatin dampened EGF-induced receptor tyrosine phosphorylation, depressed EGF-stimulated tyrosine phosphorylation of two additional cytoplasmic proteins, and interfered with receptor down regulation. Receptor tyrosine phosphorylation and down regulation are hallmarks of EGF activation of the EGF receptor. The inhibition of EGF receptor by herstatin occurred at saturating concentrations of EGF. The intron 8-encoded domain at the C-terminus of herstatin, which appears to confer high affinity binding to p185HER-2, binds to the EGF receptor but does not compete with EGF binding (Doherty et al., submitted). These results suggest that herstatin blocks activation of the EGF receptor by a mechanism that does not involve competition with growth factor binding. Other studies conducted in our lab show that herstatin associates with the EGF receptor in pull-down assays (Doherty, submitted). Since herstatin appears to form a stable complex with the EGF receptor, it may inhibit EGF-induced homodimers. It is also possible that herstatin inhibits the EGF receptor indirectly by preventing EGF-induced heterodimer formation or by an alternative mechanism that does not involve complex formation with the receptors.

Overexpression of p185HER-2 or the EGF receptor enhances cell growth and/or survival. Transfection of cells with p185HER-2 enhanced the number of colonies surviving G418 selection by about 60% and transfection with the EGF receptor increased the number of cell colonies by about 40% compared to the control transfected cells. Herstatin, transfected alone, did not significantly alter the number of colonies, although it did appear to decrease the tyrosine phosphorylation associated with an endogenous protein that comigrated with p185HER-2 in CHO cells. This may have been p185HER-2 since the CHO cells have little or no group I receptors other than p185HER-2. Herstatin coexpressed with the EGF receptor suppressed colony formation relative to cells transfected with the EGF receptor alone. Since herstatin also inhibited EGF activation of the EGF receptor, and has been found to form stable complexes with the EGF receptor (Doherty, submitted), the growth inhibition may have been due to herstatin forming an inactive kinase complex with the EGF receptor or through inhibition of transactivation of the EGF receptor by forming a complex with endogenous p185HER-2. It is also possible that the growth inhibition may have been caused by a separate unknown activity of herstatin that does not directly involve interaction with the EGF receptor or p185HER-2. The most potent growth inhibitory activity was observed when herstatin was coexpressed with p185HER-2. With this combination, there was a 7 fold reduction in colony formation relative to cells transfected with p185HER-2 alone, and a 5 fold inhibition compared to cells transfected with herstatin alone or compared to control transfected cells. Overexpressed p185HER-2 is constitutively active in cells and blocking its activity may inhibit cell survival as well as growth.

In comparison to other group I RTK inhibitors that have been described, herstatin has several similarities with the p185neu ectodomain mutant, which functions as a dominant negative inhibitor. Like herstatin, the membrane anchored dominant negative neu mutant contains sequences from the receptor extracellular domain and forms complexes with RTKs (Doherty et al., and Greene). Also both p185 neu ectodomain and herstatin, ectopically expressed, are capable of inhibition of p185HER-2 as well as the EGF receptor. In contrast to the previously described p185neu ectodomain, which consists of subdomains I through IV and a membrane anchor, herstatin contains only subdomains I and II from the p185 ectodomain, and is a naturally occurring product expressed in fetal kidney and fetal liver cells (Doherty et al., 1999). Herstatin is secreted and does not require a membrane anchor to form complexes nor to exert its inhibitory activity.

EXAMPLE 1

This example provides the results from an experiment to investigate HER-2 mRNA diversity within the extracellular domain (ECD) coding sequence using polymerase chain reaction (PCR). A cDNA library from SKOV-3 cells (American Type Culture Collection (Rockville, Md.) maintained in DMEM, supplemented with 10% fetal bovine serum and 0.05% gentamycin), an ovarian carcinoma cell line in which the HER-2 gene is amplified eight times (Tyson et al., *Am. J. Obstet. Gynecol.* 165:640-646, 1991) was examined using a forward primer specific for exon 1 (Tal et al., *Mol. Cell. Biol.*

7, 2597-2601, 1987) identical to nucleotides 142-161 and a reverse primer complementary to nucleotides 1265-1286 in exon 9 (Scott et al., *Mol. Cell. Biol.* 13:2247-2257, 1993). Briefly, The SKOV-3 cDNA library was provided by Origene Technologies, Inc. (Rockville, Md.), and was prepared from RNA extracted from SKOV-3 cells. RNA was extracted from SKOV-3 cells grown to 80% confluence on 15 cm plates with TriReagent (Molecular Research Center, Inc., Cincinnati, Ohio), according to the manufacturer's protocol, to obtain total RNA. RNA was resuspended in 10mM Tris-EDTA, pH 8.0, for reverse transcription and cDNA library construction, or in RNA hybridization buffer (80% formamide, 40 mM PIPES, 4 mM NaCl, 1 mM EDTA, pH 7.5) for ribonuclease protection assay (RPA). RNA concentrations were determined spectrophotometrically at $OD_{260}$. Poly $A^+$ mRNA was selected from total RNA using a mRNA extraction kit (Oligotex, Qiagen).

A product of ~1420 bp, determined to be HER-2-specific by Southern blotting, was approximately 270 bp larger than the expected size of 1144 bp from the previously described cDNA sequence (Coussens et al., *Science* 230:1132-1139, 1985). Briefly, the Southern blotting procedure transferred nucleic acids from agarose gels under vacuum (Bio-Rad Model 785 Vacuum Blotter) in 0.4 M NaOH to Gene Screen Plus Hybridization Transfer Membrane (NEN Research Products, Boston, Mass.). Nucleic acids were fixed to membranes by UV crosslinking in a UV-Stratalinker (Stratagene, Inc., La Jolla, Calif.), and the membranes were blocked in hybridization buffer (50% formamide, 5×SSC, 1% SDS, 10 mg/ml herring sperm DNA) at 42° C. for 2 h. The membranes were hybridized at 42° C. for 16 h in hybridization buffer with $10^7$ cpm of a 220 bp Kpn-HincII fragment from ECDIIIa cDNA labelled with $(\alpha-^{32}P)dCTP$ (NEN Life Sciences) using a Random Prime DNA Labelling Kit (Boehringer Mannheim).

Templates were amplified in a Perkin Elmer GeneAmp PCR System 2400 (Perkin Elmer Cetus, Emeryville, Calif.) using the Expand High Fidelity PCR System (Boerhinger Mannheim) with 1× High Fidelity PCR buffer containing 2.5 mM $MgCl_2$, 5 µM of each primer, and 200 µM dNTPs. All primers were obtained from GIBCO BRL (Life Technologies). Numbering of nucleotide and amino acid residues is according to the HER-2 cDNA sequence reported by Coussens et al. (Coussens et al., *Science* 230:1132-1139, 1985). The HER-2 extracellular domain was targeted for amplification from an SKOV-3 cDNA library (Origene Technologies, Inc.) using a forward primer (A) identical to nucleotides (nt) 142-161 of HER-2 cDNA (5'-TGAGCACC ATGGAGCTGGC-3' [SEQ ID NO 3]), which spans the initiation codon (underlined) and a reverse primer (B) (5'-TC-CGGCAGAAATGCCAGGCTCC-3' [SEQ ID NO 4]), which is complementary to HER-2 exon sequence at nt 1265-1286. Cycling parameters were: 94° C., 30 sec; 58° C., 45 sec; 68° C., 3 min, for 30 cycles. The region spanning the alternative sequence (denoted ECDIIIa) from genomic DNA, was amplified using a forward primer (C) (5'-AACACAGCGGTGT-GAGAAGTGC-3' [SEQ ID NO 5]) identical to HER-2. exon-specific sequence at nt 1131-1152 and the reverse primer (B) [SEQ ID NO. 4] on DNA prepared as described (Bond et al., *FEBS Letters* 367:61-66, 1995) with cycling parameters: 94° C., 30 sec; 62° C., 30 sec; 72° C., 60 sec, for 25 cycles.

Reverse transcriptase-polymerase chain reaction (RT-PCR) was used to investigate the structure of mRNA containing the ECDIIIa sequence. First strand cDNA was reverse transcribed (Bond et al., *FEBS Letters* 367:61-66, 1995) using 5 µg RNA primed with 0.5 µg oligo-dT. To amplify the ECDIIIa insert and adjacent 5' HER-2 exon sequence, a forward primer (A) described above and a reverse primer (D) (5'-ATACCGGGACAGGTCAACAGC-3' [SEQ ID NO 6]) which is complementary to the 3'ECDIIIa-specific sequence were used. Cycling parameters were: 94° C., 30 sec; 60° C., 40 sec; 68° C., 2 min, for 30 cycles.

Amplification of the ECDIIIa insert and adjacent 3' HER-2 exon-specific sequence was with a forward primer (E) (5'-TCTGGGTACCCACTCACTGC-3' [SEQ ID NO 7]) which is identical to the 5'ECDIIIa-specific sequence and contains a Kpn1 restriction site and a reverse primer (F) (5'-T TCACACTGGCACGTCCAGACC-3' [SEQ ID NO 8]) which is complementary to HER-2 exon sequence at nt 3898-3919 and spans the termination codon (underlined). Cycling parameters were: 94° C., 30 sec; 60° C., 40 sec; 68° C., 5 min, for 30 cycles.

The PCR product was subcloned and the nucleotide sequence was determined.

The results showed that the normal HER-2 coding sequence was present beginning with the 5' primer sequence and continued uninterrupted through nucleotide 1171. At this position, a 274 nucleotide insertion was found, followed by the expected coding sequence, including the 3' primer sequence. Analysis of the predicted protein product showed that the 274 nucleotide insertion encodes an extension of the known HER-2 protein, beginning at residue 340 (Coussens et al., *Science* 230:1132-1139, 1985), and introduces an in-frame stop codon 79 amino acids later (FIG. 1). Comparison of the inserted nucleotides and their predicted amino acid sequence with sequences in Genbank showed no homologies. Examination of the 5' and 3' junctions of the divergent sequence revealed consensus splice donor and acceptor sites (Sharp, and Burge, *Cell* 91:875-879, 1997) and include a pyrimidine tract and potential branchpoint adenine residues near the 3' end of the insert sequence (FIG. 1). Thus, the inserted sequence is likely to be an intron.

Inspection of the predicted amino acid sequence of the novel 79 amino acids [SEQ ID NO. 1] encoded by the inserted sequence shows a consensus N-linked glycosylation site and a high proline content of 19% (FIG. 1). The inserted sequence was designated ECDIIIa since it is located at the boundary between subdomains II and III in the extracellular domain of the p185HER-2 sequence (Lax et al., *Mol. Cell. Biol.* 8:1831-1834, 1988). The insert sequence is in-frame with the adjacent 5' HER-2 exon sequence for 236 nt where there is a termination codon.

EXAMPLE 2

This example provides the results from experiments characterizing ECDIIIa as contiguous with HER-2 exons in the genome. To investigate the HER-2 gene structure in the region of the ECDIIIa sequence, a forward primer, identical to nucleotides 763-785, and a reverse primer, complementary to nucleotides 1265-1286 of the HER-2 cDNA, were used in the PCR on human genomic DNA. The amplification product was anticipated to span exon 5 (Tal et al., *Mol. Cell. Biol.* 7:2597-2601, 1987) to an exon which is immediately 3' of the ECDIIIa sequence. Intron number and sizes were estimated based on PCR product sizes, restriction digest analysis, and partial sequence analysis of amplification products.

Next, human genomic DNA was examined using HER-2 exon-specific primers that directly flank the insert to determine the sequences immediately flanking the ECDIIIa sequence. A ~430 bp product was amplified from normal human genomic DNA and from genomic DNA extracted from carcinoma cell lines SKOV-3, SKBR-3 and BT474, all of which have HER-2 gene amplification (Kraus et al., *EMBO*

*J.* 6:605-610, 1987) and were found to express ECDIIIa in their cDNA. The identities of the PCR products as HER-2 were verified by Southern blot analysis using the procedure described in Example 1. Nucleotide sequence analysis showed that the PCR product from human genomic DNA contained the ECDIIIa insert, flanked immediately on both sides by known HER-2 coding sequence; no mutations or rearrangements were seen. These data show that the ECDIIIa sequence represents a wholly retained intron, likely intron 8 based on the size of products amplified following intron 4 and on the location of intron 8 in the homologous EGFR gene and HER-3 gene (Lee and Maihle, *Oncogene* 16:3243-3252, 1998).

EXAMPLE 3

This example shows that ECDIIIa is the only retained intron within the coding sequence of HER-2 mRNA. To determine whether additional introns were retained in the mRNA containing the ECDIIIa insert sequence, the reverse transcriptase-polymerase chain reaction (RT-PCR) was employed. First, a forward primer identical to 5' HER-2 cDNA sequence at 142-161 which spans the initiation codon, and a reverse primer complementary to the 3' ECDIIIa sequence were employed with SKBR-3 and SKOV-3 cDNA. A product of 1.3 kb was amplified, which is the size expected if the product contained no introns other than intron 8. Amplification of the 3'HER-2 coding sequence was then performed using a forward primer identical to 5' ECDIIIa sequence and a reverse primer complementary to 3'HER-2 cDNA sequence at nucleotides 3898-3919, which spans the p185HER-2 termination codon. A product of 2.9 kb was amplified, which is the size expected from the HER-2 cDNA if no additional introns were retained.

Further characterizations of both the 5'(1.3 kb) and 3'(2.9 kb) amplification products by restriction digest analysis and nucleotide sequencing confirmed the absence of additional retained introns. To determine the size of the products amplified when intron sequences are included, genomic DNA was used as a template for the PCR reactions, which resulted in products of approximately 10 kb for the 5' coding sequence and 5 kb for the 3' coding sequence. These results indicate that the alternative HER-2 transcript, resulting from retention of an intron of 274 bp, was expected to be about 4.8 kb in size, assuming that the 5'untranslated (5'UTR) and 3'untranslated (3'UTR) regions are identical in size to the previously described ~4.5 kb HER-2 cDNA (Coussens et al., *Science* 230:1132-1139, 1985).

EXAMPLE 4

This example illustrates the expression of a protein containing an ECDIIIa sequence. To assess whether the alternative sequence is translated into a protein product, the ECDIIIa sequence was expressed as a polyhistidine-tagged peptide in bacteria, purified the peptide by nickel-affinity chromatography, and raised antisera against the purified peptide. Briefly, the bacterial expression vector was prepared by amplifying the ECDIIIa sequence from the SKOV-3 cDNA library using primer E and a reverse primer complementary to the 3' end of the ECDIIIa insert sequence. The reverse primer contained a BamH1 restriction site sequence, and was identical to that used for template construction in the RPA (described in examples 1 and 2). The PCR amplification product of ~280 bp was digested with Kpn1 and BamH1, gel purified (Qiaex II, Qiagen, Chatsworth, Calif.), and cloned into the pET30a vector, which encodes a six histidine tag at the amino-terminus of the expressed protein (Novagen, Madison, Wis.). The resulting expression vector, pET-ECDIIIa, was used for transformation of bacterial strain BL21.

To express the ECDIIIa protein product, BL21 cells transformed with the pET-ECDIIIa expression vector were grown in LB broth with 30 µg/ml Kanamycin for 4 h at 37° C. Expression was induced with 0.1 mM IPTG for 3 h and the harvested cells were lysed by sonication, and then centrifuged at 39,000×g for 20 min. The supernatant was absorbed onto Ni-NTA agarose (Qiagen), by shaking for 60 min at room temperature. The resin was washed with ten volumes of wash buffer (10 mM Tris pH 7.9 and 300 mM NaCl), followed by ten volumes of wash buffer with 50 mM imidazole. The his-tagged ECDIIIa protein was eluted in wash buffer with 250 mM imidazole. The his-tagged protein, which was estimated to be approximately 90% pure by Coomassie Blue staining of gels, was used to generate and characterize antibodies.

Briefly, anti-ECDIIIa antisera were produced by Cocalico Biologicals, Inc. (Reamstown, Pa.) by injection of two rabbits with purified polyhistidine-tagged ECDIIIa peptide (described below). Polyclonal anti-neu (N) was produced against a peptide identical to amino acid residues 151-165 of p185HER-2 (Lin and Clinton, *Oncogene* 6:639-643, 1991). Polyclonal anti-neu (C) was made against a peptide identical to the last 15 residues of the carboxy-terminus of p185HER-2 (Lin et al., *Mol. Cell. Endocrin.* 69:111-119, 1990). Antisera from two immunized rabbits were characterized and found to contain antibodies of high titer that reacted with the purified ECDIIIa peptide.

A Western blot analysis examined whether SKBR-3 cells, which expressed the alternative sequence in its cDNA, produced a protein that reacts with anti-ECDIIIa antibody. A 68 kDa protein from the cell extract and from the extracellular media reacted with anti-ECDIIIa antibody from two different rabbits diluted at least 20,000 fold, but not with preimmune sera. Inspection of the cDNA sequence of the alternative transcript (FIG. 1) predicted a secreted protein product of 65-70 kDa if all 5 consensus N-linked glycosylation sites in the N-terminal p185HER-2 sequence were glycosylated (Stern et al., *Mol. Cell. Biol.* 6:1729-1740, 1986).

If the 68 kDa ECDIIIa protein [SEQ ID NO. 2] is the translation product of the alternative HER-2 mRNA, then its N-terminal residues should be identical to the N-terminal 340 residues of p185HER-2. Therefore, cell extract from SKBR-3 cells was immunoprecipitated with anti-peptide antibody against an N-terminal sequence of HER-2, anti-neu (N) (Lin and Clinton, *Oncogene* 6:639-643, 1991) or with anti-ECDIIIa, and the immune complexes were examined by Western blot analysis with both antibodies. Briefly, three to 5 µl of antisera were added to 2 mg of protein from cell lysates prepared in M-RIPA buffer (1% Nonidet P-40, 50 mM Tris pH 7.4, 0.1% sodium deoxycholate, 150 mM NaCl, 1 mM PMSF, 1% aprotinin), which had been centrifuged to remove nuclei. Immunoprecipitation was for 2 h with shaking at 4° C. as described (Lin et al., *Mol. Cell. Endocrin.* 69:111-119, 1990). The immune complexes were bound to Protein G Sepharose (Pharmacia) by incubation for 1 h at 4° C. with shaking, collected by centrifugation, and washed four times with M-RIPA. The proteins were released from the immune complex by incubation at 95° C. for 2 min in SDS-PAGE sample buffer and resolved by SDS-PAGE in 7.5% gels (Mini-Protean II electrophoresis cell, Bio-Rad).

Western blotting was conducted following SDS-PAGE. Proteins were electroblotted onto nitrocellulose (Trans-blot, BioRad) using a semi-dry transfer unit (Bio-Rad) at 15 V for 20 min per gel (0.75 mm thick) equilibrated with 25 mM Tris pH 8.3, 192 mM glycine, 50 mM NaCl, and 20% methanol. The membranes were blocked with 5% nonfat dry milk at 25° C. for one hour. The blots were then incubated with primary antibody, washed twice for 15 min, and four times for 5 min with TBS-Tween (Tris-buffered saline containing 0.05% Tween), and then incubated for 40 min with goat anti-rabbit secondary antibody, conjugated to horseradish peroxidase (Bio-Rad), diluted 1:10,000 in TBS-Tween. After incubation with secondary antibody, the membranes were washed as described above and reacted with chemiluminescent reagent (Pierce) and then were exposed to Kodak X-OMAT BLU film.

As expected, p68HER-2 was detected when anti-ECDIIIa was used for immunoprecipitation and for Western blot analysis. When anti-ECDIIIa was used for immunoprecipitation and anti-neu (N) was the probe in the Western blot, a 68 kDa protein was detected, indicating that p68ECDIIIa contained the N-terminal sequence of p185HER-2. Further, anti-neu (N) precipitated p68HER-2, which was detected by probing with anti-ECDIIIa antibody. These results demonstrate that p68HER-2 contains both ECDIIIa and the N-terminal sequence of HER-2.

Several other cell lines were examined for expression of p68ECDIIIa. The carcinoma cell lines which contained ECDIIIa sequence in their cDNA (BT474, SKOV-3) also had p68HER-2. Of several cell lines examined, HEK293 cells, derived from normal human embryonic kidney cells, expressed the highest levels of p68ECDIIIa in the cell extract and in the extracellular media, at about 5 to 10-fold higher amounts than SKBR-3 cells. In comparison to the carcinoma cell lines examined (SKBR-3, SKOV-3, and BT474) which overexpress p185HER-2, the HEK293 cells contained about 20 fold lower amounts of p185HER-2. Therefore, the relative proportion of p68HER-2 to p185HER-2 was at least 100 fold greater in HEK293 cells than in the three carcinoma cell lines studied. Reactivity with p68HER-2 as well as with a protein of 120 kDa, particularly apparent in the HEK293 extracts, was blocked by preincubation of the antisera with purified ECDIIIa peptide demonstrating sequence-specific reactivity. The larger protein may be a dimer of p68HER-2. Therefore, p68HER-2 was expressed and secreted from several carcinoma cell lines and is at 5-10 fold elevated levels in HEK293.

EXAMPLE 5

This example illustrates expression of an alternative HER-2 transcript containing the ECDIIIa intron sequence. Results of the RT-PCR analysis indicated that the ECDIIIa sequence was inserted into an otherwise normal-sized HER-2 mRNA. These data suggest an alternative transcript of ~4.8 kb. To examine the size and expression of the ECDIIIa alternative transcript, Northern blot analysis was conducted using an ECDIIIa-specific probe. Briefly, a template for antisense RNA probe synthesis was constructed from SKOV-3 cDNA by PCR amplification of a 389 bp sequence spanning the entire ECDIIIa insert sequence and containing adjacent 5'HER-2 exon sequence. The PCR was done using the forward primer C [SEQ ID NO. 5] that is identical to HER-2 cDNA sequence at nt 1131-1152 and a reverse primer (5'-GCACGGATCCATAGCAGACTGAG GAGG-3' [SEQ ID NO. 9]) which contains a 3' BamH1 restriction endonuclease site and is complementary to the sequence spanning the 3' splice site of the ECDIIIa sequence. The PCR product was then digested with BamH1, liberating a 375 bp fragment, which was cloned into pBluescript SK (Stratagene). The plasmid was sequenced by the Vollum Institute Core Sequencing Facility (Portland, Oreg.) with m13 forward and reverse primers. An antisense RNA probe complimentary to the entire ECDIIIa sequence and to 87 nt of HER-2 exon sequence 5' to the insert was transcribed from 1 μg of linearized template using ($\alpha$-$^{32}$P) CTP, T7 RNA polymerase, and the T7/SP6 Riboprobe Synthesis System (Promega, Madison, Wis.). This probe was expected to protect a 370 nt fragment when hybridized with mRNA containing ECDIIIa and adjacent HER-2 exon sequence, and to protect an 87 nt fragment when hybridized with fully spliced HER-2 mRNA.

To prepare the RNA hybrids, 30 μg of RNA were hybridized with approximately 50,000 cpm of antisense RNA probe at 48° C. for 16 h. RNA hybrids were digested for 30 min at 37° C. with 40 μg/ml RNaseA (Boerhinger Mannheim) and 2 μg/ml RNase T1 (Life Technologies) in a solution of 250 mM NaCl, 5 mM EDTA, and 10 mM Tris pH 7.5. Proteinase K (100 μg) (Life Technologies) in 20 μl 10% SDS was added to stop the digestion. Samples were extracted with acid phenol (pH 4.5; Life Technologies) and chloroform, precipitated with two volumes of 100% ethanol, and suspended in 5 μl of RPA sample buffer (88% formamide, 10 mM EDTA pH 8.0, 1 mg/ml xylene cyanol, and 1 mg/ml bromophenol blue). Samples were denatured at 95° C. for 10 min and electrophoresed on a 5% polyacrylamide/urea gel in TBE (89 mM Tris, 89 mM borate, 2 mM EDTA pH 8.3). Gels were dried under vacuum and subjected to phosphorimager analysis for quantitation of the protected fragments (IP Lab Gel, Molecular Dynamics).

An alternative transcript of approximately 4.8 kb was detected in HEK293 cells which expressed the highest levels of p68ECDIIIa. However an alternative transcript could not be detected by Northern analysis of the SKBR-3, BT474, or SKOV-3 carcinoma cell lines. Therefore, the more sensitive ribonuclease protection assay (RPA) was employed to examine the expression levels of the alternative transcript relative to the fully spliced 4.5 kb transcript. RNA from ovarian (SKOV-3) and breast (SKBR-3 and BT474) carcinoma cell lines, which contained detectable levels of p68ECDIIIa, and a control cell line, 17-3-1, stably transfected with HER-2 cDNA, were hybridized with an antisense $^{32}$P-labeled RNA probe which spanned the entire ECDIIIa (intron 8) sequence and 5' HER-2 exon sequence flanking intron 8. Following RNase digestion, electrophoresis, and autoradiography, a band of 370 nucleotides was detected in each cell line except for 17-3-1, which corresponds to the expected size protected by an ECDIIIa-containing HER-2 mRNA. In addition, an 87 nucleotide protected fragment was detected in all cells and is the size expected for the fully-spliced HER-2 message which is overexpressed by more than 100 fold in these carcinoma cell lines compared to normal control cell lines (Kraus et al., *EMBO J.* 6:605-610, 1987). The amounts of each protected fragment were quantitated and normalized for size to estimate the relative abundance of the alternative transcript, expressed as a percentage of the p185HER-2 mRNA. The alternative HER-2 mRNA with the ECDIIIa insert was at 4.2% the level of the fully spliced transcript in SKOV-3; 5.4% in SKBR-3, and 0.8% in BT474 cells.

EXAMPLE 6

This example shows that alternative transcripts containing the ECDIIIa insert were expressed in human embryonic kidney and liver. A Northern blot was conducted to examine whether an alternative transcript, which contains the ECDIIIa sequence, was expressed in normal human tissue. PolyA$^+$ mRNA from a variety of human fetal tissues prepared as a Northern blot was hybridized with a radiolabeled probe specific for the unique ECDIIIa sequence. A 4.8 kb mRNA was detected in kidney and a 2.6 kb transcript was detected in liver (FIG. 2). The 4.8 kb transcript likely corresponded to the full length 4.5 kb transcript with the 274 bp insert and the 2.6 kb transcript may have corresponded to a previously described 2.3 kb alternative transcript (Yamamoto et al., Nature 319: 230-234, 1986; and Scott et al., Mol. Cell. Biol. 13:2247-2257, 1993) with the 274 bp ECDIIIa insert. When the blot was stripped and hybridized with a probe specific for the 5' HER-2 coding sequence, a broad band representing the 4.8 and 4.5 kb mRNAs was detected in fetal kidney tissues and the truncated 2.6 kb transcript was detected in liver showing that these alternative transcripts contain sequences that encode the HER-2 ECD. Because the inserted ECDIIIa sequence contained a termination codon, the same protein product may be produced from each of these mRNAs.

Several cell lines were also investigated for the ECDIIIa-containing alternative transcript by Northern blot analysis. The 4.8 kb alternative transcript was detected in the human embryonic kidney cell line, HEK-293 (FIG. 2). Although the ECDIIIa sequence was detected by RT-PCR analysis of SKBR-3, BT474, and SKOV-3 carcinoma cell lines, which all contain HER-2 gene amplification, an ECDIIIa-containing alternative transcript could not be detected by Northern analysis of these cells. Therefore, the more sensitive ribonuclease protection assay (RPA) was employed using an antisense probe which spanned the entire ECDIIIa sequence and 5' HER-2 exon sequence flanking the ECDIIIa sequence. The alternative HER-2 mRNA with the ECDIIIa insert was detected at less than 5% of the fully spliced transcript in SKOV-3, SKBR-3, and BT474 cells. These findings show that two alternative transcripts containing the ECDIIIa sequence were expressed in a tissue-specific manner in normal human tissues, that the 4.8 kb alternative transcript was expressed in the HEK-293 cell line, and that the carcinoma cells with gene amplification express reduced amounts of the alternative transcript at less than 5% of the 4.5 kb HER-2 transcript.

EXAMPLE 7

This example illustrates expression of a protein containing the ECDIIIa sequence. To assess whether the alternative sequence was translated into a protein product, the ECDIIIa sequence, as a polyhistidine-tagged peptide in bacteria, was expressed and purified by nickel-affinity chromatography, and raised antisera against the purified peptide. The HEK-293 cells, which expressed the 4.8 kb ECDIIIa alternative transcript, were examined for expression of an ECDIIIa-containing protein by Western analysis. A 68 kDa protein from the cell extract and from the extracellular media reacted with the anti-ECDIIIa antibody (FIG. 3) but not with preimmune sera and reactivity was blocked by preincubation of the antisera with purified ECDIIIa peptide (FIG. 3). The larger protein of 125 kDa detected in some cell extracts may be an aggregate of p68HER-2. The cDNA sequence of the alternative transcript (FIG. 1) predicts a secreted protein product of 65-70 kDa if all 5 consensus N-linked glycosylation sites in the N-terminal p185HER-2 sequence are glycosylated (Stern et al., Mol. Cell. Biol. 6:1729-1740, 1986). Several other cell lines were examined for expression of p68ECDIIIa. The carcinoma cell lines which contained ECDIIIa sequence in their cDNA (BT474, SKOV-3, SKBR-3) also had detectable levels of p68HER-2.

EXAMPLE 8

Figure 4:
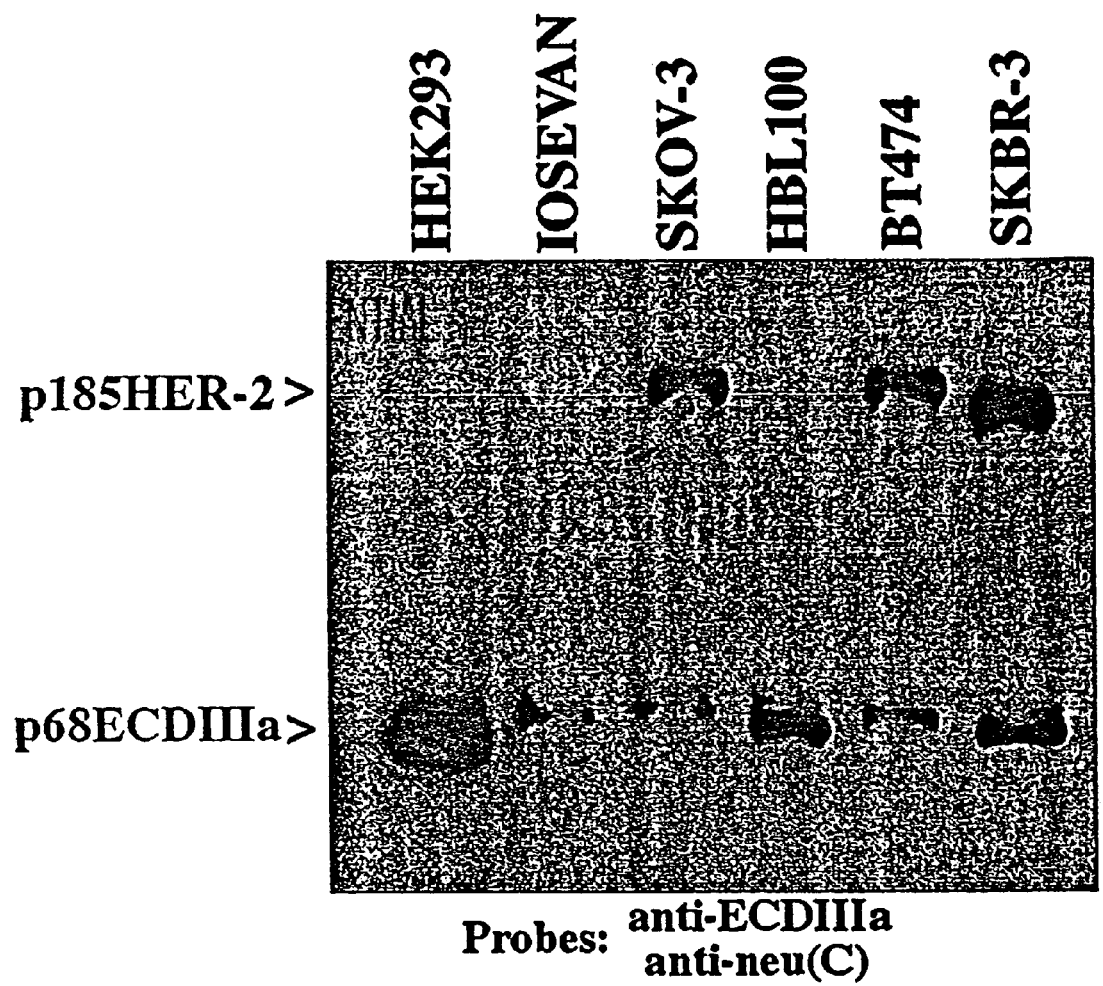
FIG. 4 shows the expression of p185HER-2, relative to p68ECDIIIa expression, is markedly elevated in carcinoma cell lines in which the HER-2 gene is amplified. Cell extracts (15 µg of protein) from human embryonic kidney cell line (HEK293), nontumorigenic ovarian surface epithelial cell line (IOSEVAN), ovarian carcinoma cell line with HER-2 gene amplification (SKOV-3), nontumorigenic breast epithelial cell line (HBL100), and breast carcinoma cell lines with HER-2 gene amplification (BT474 and SKBR-3), were resolved by SDS-PAGE in 7.5% acrylamide gels and analyzed as a Western blot. The Western blot was probed with both antibodies specific for p68HER-2 (anti-ECDIIIa) and for p185HER-2 (anti-neu(C)).

This example illustrates the expression of p68HER-2 relative to p185HER-2 was markedly reduced in carcinoma cell lines in which the HER-2 gene is amplified. Because the p68HER-2 mRNA was expressed at very low levels relative to the p185HER-2 mRNA in carcinoma cell lines with HER-2 gene amplification, the relative proportions of p68HER-2 and p185HER-2 proteins in several cell lines were examined with and without HER-2 gene amplification. Western blots were prepared and probed with both antisera specific for p68HER-2 and for p185HER-2. FIG. 4 shows that p185HER-2 was readily detected in the carcinoma cells lines that have their HER-2 gene amplified about 8 times (Kraus et al., EMBO J. 6:605-610, 1987). However, there was not a corresponding elevation in p68HER-2. In comparison, p68HER-2 was the only HER-2 protein detected in the HEK-293, IOSEVAN, and HBL100 nontumorigenic cells, although p185HER-2 was expressed at very low levels in these cells (Kraus et al., EMBO J. 6:605-610, 1987) and was detected in overexposed blots. These data show that p68HER-2 was low in proportion to p185HER-2 in carcinoma cells with HER-2 gene amplification and suggests that a mechanism may exist to maintain low levels of p68HER-2 when p185HER-2 is overexpressed.

EXAMPLE 9

This example illustrates that p68HER-2 and the ECDIIIa peptide specifically bind to p185HER-2. Because p68HER-2 is secreted and contains subdomains I and II identical to p185HER-2, in addition to a novel sequence, the possibility that p68HER-2 may interact with p185HER-2 was investigated. Antipeptide antibody against the N-terminus of p185HER-2 and p68HER-2, anti-neu (N), or antibody specific for p185HER-2, anti-neu(C), were used for immunoprecipitations of SKBR-3 carcinoma cells, which express low levels of p68HER-2 and overexpress p185HER-2. The immunoprecipitated material was prepared as a Western blot and probed with both anti-ECDIIIa specific for p68HER-2 and with anti-neu(C). Anti-neu (N) immunoprecipitated both p68HER-2 and p185HER-2 (FIG. 5A). In addition, antibodies specific for the C-terminus of p185HER-2 immunoprecipitated p185HER-2 and coprecipitated p68HER-2 (FIG. 5A), suggesting an interaction between the two proteins.

Since binding interactions between ECD sequences are very weak (Tzahar et al., EMBO J. 16:4938-4950, 1997; Fitzpatrick et al., FEBS Letters 431:102-106, 1998), the possibility that binding may be conferred by the novel proline rich ECDIIIa domain was examined. The unique 79 amino acid domain, purified as a His-tagged protein, was immobilized on nickel agarose and used in a pull-down assay. For controls, two purified His-tagged peptides unrelated to ECDIIIa, a 600 residue fragment of the Wilson's disease membrane protein, and a 70 residue fragment containing the DNA binding domain of the CREB protein, were likewise immobilized on nickel agarose resin. The immobilized peptides were incubated with protein extracts prepared from: HER-2 transfected 3T3 cells (17-3-1). Following extensive washes, the bound proteins were eluted and prepared as a Western blot which was probed with an antibody specific for p185HER-2. Equal amounts of His-tagged ECDIIIa peptide and control peptide were bound to the resin as confirmed by elution with 1M imidazole and Coomassie staining of the eluted material in SDS-gels. While no p185HER-2 was retained by resin without peptide or with control peptide, p185HER-2 was selectively retained by the ECDIIIa peptide (FIG. 5B).

Since the ECDIIIa domain bound to p185HER-2 in a pull-down assay, the question of whether the ECDIIIa domain preferentially binds to cells that overexpress p185HER-2 was examined. This was investigated using monolayer cultures of 17-3-1 cells transfected with HER-2 compared to the parental 3T3 cells. The cells were incubated with different concentrations of the His-ECDIIIa peptide, washed, and extracted in denaturing buffer with protease inhibitors. To detect any bound peptide, the cell extracts were examined by Western blot analysis using antibodies specific for ECDIIIa. In addition, equal aliquots of the ECDIIIa peptide treated cells were reacted as a Western blot with antibodies specific for p185HER-2, demonstrating the overexpression of p185HER-2 in the transfected 17-3-1 cells. The ECDIIIa peptide preferentially bound to intact 17-3-1 cells at nM concentrations (FIG. 5C) whereas little or no peptide was found to bind to equivalent amounts of parental 3T3 cells suggesting a specific interaction with the extracellular domain of p185HER-2.

EXAMPLE 10

Figure 6:
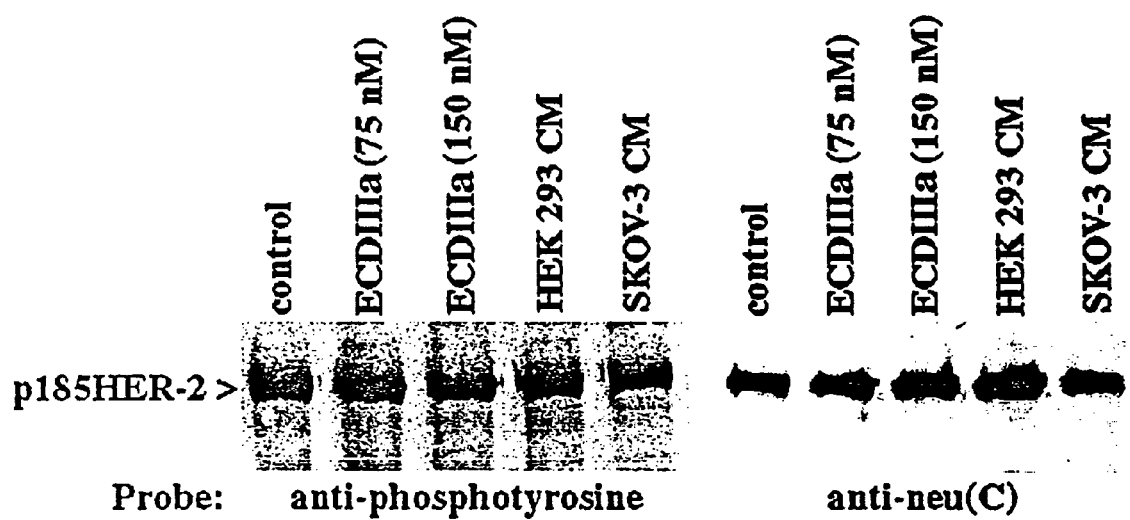
FIG. 6 shows that neither p68-rich conditioned media nor the ECDIIIa peptide stimulate tyrosine phosphorylation of p185HER-2. Monolayer cultures of 5 HER-2 transfected 17-3-1 cells were washed twice with PBS, incubated in serum-free media at 37° C. for 24 hrs, and then treated for 10 minutes with 75 or 150 µM His-tagged ECDIIIa or with 50×CM from HEK-293 cells that secrete high levels of p68 or 50×CM from SKOV-3 cells that have no detectable p68HER-2. The treated cells were extracted with denaturing buffer containing the phosphotyrosine phosphatase inhibitor vanadate (2 mM) and 20 µg/ml of cell extract protein from each sample were analyzed by Western blot analysis with monoclonal antibodies against phosphotyrosine (Sigma). The blot was stripped by incubation at 55° C. for 30 min in 62.5 mM Tris pH 6.7, 2% SDS, and 100 mM 2-mercaptoethanol and then reprobed with anti-neu(C) specific for p185HER-2.

Effect of p68ECDIIIa and the ECDIIIa peptide on tyrosine phosphorylation of p185HER-2 was examined. Tyrosine phosphorylation of RTKs is the initial indication of ligand activation and signal transduction. Tyrosine phosphorylation in 17-3-1 cells treated with different amounts of the purified ECDIIIa peptide, with conditioned media (CM) from HEK293 cells that contained high levels of p68HER-2 (FIG. 2A), or with control, conditioned media from SKOV-3 cells that had no detectable p68HER-2 were examined. There was no increase in the tyrosine phosphorylation signal at 10 minutes (FIG. 6) or 2 hrs of treatment with His-ECDIIIa or with concentrated CM suggesting that p185HER-2 was not activated. Neither p68HER-2-containing CM nor the ECDIIIa peptide detectably altered the phosphotyrosine signal corresponding to p185HER-2 from SKOV-3 cells in which p185HER-2 tyrosine phosphorylation levels were low. Additionally, p68HER-2 and the ECDIIIa peptide had no discernable effect on in vitro self-phosphorylation activity of p185HER-2 immunoprecipitated from 17-3-1 cell extracts. These results support the conclusion that p68HER-2 did not activate p185HER-2 signal transduction.

EXAMPLE 11

This example illustrates that the sequence of intron 8 is polymorphic. Intron 8 of the human HER-2 gene is alternatively retained in mRNA, and encodes a novel 79-residue domain at the C-terminus of a part of the extracellular domain of p185HER-2. The product, "herstatin," of the alternative transcript with the retained intron functions as an autoinhibitor of the HER-2 oncogene. The intron 8 encoded domain, alone, was shown to bind with mM affinity to p185HER-2. (Doherty et al., *Proc. Natl. Acad. Sci. USA* 96:10,869-10,874, 1999).

Additionally, polymorphisms in the nucleotide and deduced amino acid sequence of intron 8 in the HER-2 gene were identified by sequencing genomic DNA from 15 different individuals. FIG. 8 and SEQ ID NO:1 show the most common nucleotide and corresponding amino acid sequences, respectively, of intron 8. This region contains 10 different polymorphisms (marked by the letters W (2×), Y (3×), R, N, M (2×), and S (1×) in SEQ ID NO:10; or marked by an "X" in FIG. 8) that result in nonconservative amino acid substitutions (see legend to TABLE 1). For example, the polymorphism (C→G) at nucleotide position 161 (FIG. 8; TABLE 1) would result in a substitution of Arginine (R) for Proline (P) at amino acid residue #54 of SEQ ID NO:1, or residue #394 of SEQ ID NO:2. The N-terminal Glycine (G), designated as position 1 in FIG. 8 or SEQ ID NO:10, corresponds to amino acid residue #341 in the "herstatin" sequence (Doherty et al., *Proc. Natl. Acad. Sci. USA* 96:10,869-10,874, 1999). The nucleotide sequence shown in FIG. 1(A) is a polymorphic form that differs at amino acid residues #6 and #73 from the most commonly detected sequence shown here in FIG. 8.

This result demonstrates that in the human population there are several variations in the intron-8 encoded domain that could lead to altered biochemical and biological properties among ECDIIIa-containing protein variants. Some identified variants are summarized in Table 1:

TABLE 1

|  | X(4) | X(14) | X(17) | X(47) | X(52) | X(62) | X(106) | X(161) | X(191) | X(217) |
|---|---|---|---|---|---|---|---|---|---|---|
| Variant 1 | T | | | | | | | | | |
| Variant 2 | | C | | | | | | | | |
| Variant 3 | | | T | | | | | | | |
| Variant 4 | | | | A | | | | | | |
| Variant 5 | | | | | C | | | | | |
| Variant 6 | | | | | | C, T, A | | | | |
| Variant 7 | | | | | | | A | | | |
| Variant 8 | | | | | | | | G | | |
| Variant 9 | | | | | | | | | T | |
| Variant 10 | | | | | | | | | | A |
| Variant 11 | | | T | | | | | | | A |

Table 1. Sequence variants in the intron-8 encoded domain found in the human population (based on 15 different individuals). Sequence variants 1-11 are listed, showing the base changes at a particular "X" positions relative to that found in the most common DNA sequence shown in FIG. 8. The numbers in parenthesis after each X correspond to the nucleotide position in the DNA sequence shown in FIG. 8. The DNA sequence variants listed here correspond to the variable amino acid positions ("Xaa") of SEQ ID NO:1 as follows: X(4) to Xaa(2); X(14) to Xaa(5); X(17) to Xaa(6); X(47) to Xaa(16); X(52) to Xaa(18); X(62) to Xaa(21); X(106) to Xaa(36); X(161) to Xaa(54); X(191) to Xaa(64); X(217) to Xaa(73); and to the variable amino acid positions of SEQ ID NO:2 as follows: X(4) to Xaa(342); X(14) to Xaa(345); X(17) to Xaa(346); X(47) to Xaa(356); X(52) to Xaa(358); X(62) to Xaa(361); X(106) to Xaa(376); X(161) to Xaa(394); X(191) to Xaa(404); X(217) to Xaa(413). The specific amino acid changes (relative to the most common DNA sequence of FIG. 8) for the variable amino acid positions in SEQ ID NO:1 are: Variant 1, Xaa(2)(Thr→Ser); Variant 2, Xaa(5) (Leu→Pro); Variant 3, Xaa(6) (Pro→Leu); Variant 4, Xaa(16) (Leu→Gln); Variant 5, Xaa(18) (Met→Leu); Variant 6, Xaa

(21) (Gly→Asp, Alu or Val); Variant 7, Xaa(36) (Leu→Ile); Variant 8, Xaa(54) (Pro→Arg); Variant 9, Xaa(64) (Pro→Leu); Variant 10, Xaa(73) (Asp→Asn), and Variant 11, Xaa(6) (Pro→Leu) and Xaa(73) (Asp→Asn). The same substitutions apply to the corresponding variable amino acid positions in SEQ ID NO:2.

EXAMPLE 12

Co-Expression of Herstatin in Transfected Cells (1) Inhibited p185HER-2 Levels by Inhibiting Colony Formation, and (2) Inhibited p185HER-2 Tyrosine Phosphorylation The effects of the herstatin/p185HER-2 binding interaction were further characterized by co-transfecting Cos-7 cells with herstatin and p185HER-2-expressing vectors, and measuring the resulting p185HER-2 levels, and the extent of post-transfection colony formation and p185HER-2 tyrosine phosphorylation.

Methods. Transfection of Cos-7 cells. Cos-7 cells were plated at $2\times10^5$ cell/well into 6-well plates and transfected using Lipofectamine (BioRrad). The cells were transfected with 1.5 µg of herstatin expression vector plus 1.5 µg of HER-2 expression vector, or with 1.5 µg of HER-2 expression vector (all pcDNA3.1 from Invitrogen). The total amount of DNA in each case was adjusted to 3 µg with control empty vector. The transfected cells were analyzed after 48 hrs by Western blot analysis, and protein was detected with antibodies against p185HER-2, anti-neu (C), or with antibodies against the intron 8-encoded C-terminal sequence of herstatin (anti-Hst). For β-galactosidase marker expression reactions, transfections were conducted in triplicate using the indicated plasmids with the inclusion of 0.5 µg of β-galactosidase expression plasmid driven by a CMV promoter. At 48 hrs, the cells were extracted, cell protein was quantitated by BioRad protein dye kit, and the β-galactosidase activity was measured. The β-galactosidase activity was normalized to protein amounts and the mean results with the standard deviations are plotted. A similar result was obtained when β-galactosidase activity was normalized to the number of cells originally plated into each well.

Colony formation measurements. CHO cells were seeded at $2\times10^5$ cells/well in 6-well plates and triplicate wells were transfected with 3 mg of control empty plasmid (pcDNA 3.1; Invitrogen), 1.5 mg of p185HER-2 expression plasmid plus 1.5 mg of control DNA; 1.5 mg of p185HER-2 plus 1.5 mg of herstatin; or 1.5 mg of herstatin plus 1.5 mg of control DNA. At 48 hours after addition of DNA, the cells were trypsinized and diluted 1:10 into 6-well plates in the presence of 0.6 mg/ml of G418. The media was changed every two days. At 14 days, the plates were stained with crystal violet and washed. The crystal violet-stained plates were extracted by shaking at room temperature for 30 minutes with 1 ml of 0.1 M sodium phosphate, pH 4.5, in 50% ethanol. The extracted crystal violet, diluted 10-fold, was quantitated by measuring the absorbency at 515 nM. Dilutions of 10-fold gave readings of 0.1 to 1.0, which were in the linear range of absorbency versus cell number, determined in pilot studies.

Measurement of the inhibition of p185HER-2 tyrosine-phosphorylation. Cos-7 cells were plated into 6-well plates and transfected as above. Cells in duplicate wells were transfected with 0.25, 0.5, 1.0, and 3 zg of fluorescent green protein ("FGP") expression plasmid. Empty vector was added to make the total amount of DNA equal to 3 µg in each well. After 48 hrs, the fluorescent signal was quantified at a wavelength of 520 mM for emission and 490 nM for excitation using a fluorescent plate reader. Alternatively, cells were transfected with 0.5 µg of FGP plasmid, with or without 1.5 µg of HER-2 plasmid, and with the indicated amounts of herstatin expression plasmid. Empty vector was added to make the total amount of DNA at 5 µg in each well. After 48 hrs, the cells were washed twice with PBS, extracted in 100 µl of modified RIPA containing 1 mM phenylmethylsulfonylfluoride and 2 mM orthovanadate. The protein concentration in the clarified extracts was determined using the BioRad protein dye kit. The extracted protein, 20 µg, was resolved using 7.5% polyacrylamide-SDS gels and analyzed as a Western blot, first using 1 µg/ml of anti-phosphotyrosine antibody ("anti-Ptyr") (Panel C [?]). The blot was stripped and then was reacted with antibodies against p185HER-2 (anti-neu (C)). The blots were developed using chemiluminescent reagent (Pierce) and exposed to Kodak film.

(1) Ectopic herstatin expression decreased p185HER-2 levels in transfected Cos-7 cells by decreasing post-transfection survival. Levels of p185HER-2 were decreased about 5-fold when herstatin was co-expressed with p185HER-2 in Cos-7 cells, compared to cells transfected with p185HER-2 alone (FIG. 9). Expression of α-galactosidase ("β-gal") activity from a marker plasmid was monitored as an internal control.

FIG. 10 shows that the β-gal activity was greatest when the β-gal marker plasmid was co-transfected with p185HER-2 (about 35% higher than when β-gal plasmid was co-transfected with empty plasmid, "pcDNA"). By contrast, the level of β-gal activity was reduced about 3-fold in cells that were co-transfected with herstatin in combination with p185HER-2 and the β-gal plasmid. A similar reduction was observed in two additional cell lines, CHO and HEK-293. Additionally, a similar level of inhibition of marker-gene expression was observed when an alternative marker, fluorescent green protein ("FGP"), was examined in cells co-transfected with herstatin and HER-2. Thus, co-transfection of marker plasmids with p185HER-2 alone increased the level of co-transfected marker expression, while co-transfection marker plasmids with herstatin and p185HER-2 reduced the marker signal.

The above-identified decrease in the level of p185HER-2 and marker gene expression was consistent with either a general reduction in the level of p185HER-2 (or marker) per transfected cell, or with a decrease in the survival of post-transfected cells (i.e., whereby survival was enhanced by expression of p185HER-2, and inhibited by co-expression of herstatin and p185HER-2).

CHO cells (suitable for displaying rapid growth of stably transfected cells) were transfected, subjected to selection with G418 for 20 days, and the surviving cell colonies were stained and quantitated to directly measure effects of co-transfections on colony formation. Transfection with p185HER-2 enhanced colony growth by about 60% relative to the control transfected cells, while herstatin, expressed alone, did not significantly alter growth (FIG. 11). By contrast, co-transfection of herstatin dramatically reduced colony formation of HER-2 transfected cells by about 7-fold (FIG. 11).

The affect of herstatin expression on p185HER-2 in transfected cells was further evaluated by varying the relative proportion of transfected herstatin and p185HER-2 expression plasmids. When the herstatin plasmid was introduced at 5-fold lower level relative to the p185HER-2 plasmid, there was essentially no effect on the level of p185HER-2. As the amount of the herstatin plasmid was increased relative to the p185HER-2 plasmid, p185HER-2 levels were reduced (FIG. 14 panel B) and the expression of co-transfected marker GFP plasmid was reduced as in FIG. 9. In contrast, transfection with the control GFP expression plasmid alone, which does not affect cell survival, resulted in GFP expression that was proportional to the amount of plasmid added (FIG. 13).

Therefore, the reduction in the level of p185HER-2 in cells co-transfected with herstatin was attributable to a decrease in the extent of colony formation of post-transfected cells, and not to a decrease in the level of p185HER-2 per transfected cell. Moreover, survival of the transfected cells was dependent upon the relative amount of expressed herstatin and p185HER-2. Stated alternatively, the survivability of p185HER-2-expressing cells was substantially reduced upon exposure to herstatin.

(2) Herstatin expression inhibits p185HER-2 tyrosine-phosphorylation. Under 4 circumstances where co-transfection with herstatin resulted in a 3-fold reduction in p185HER-2 levels, p185HER-2 tyrosine phosphorylation signal was diminished by 25-fold. This amounts to an approximate 8-fold decrease in the level of tyrosine phosphorylation of p185HER-2 per cell (FIG. 15).

As in the case of cell survival, the extent of inhibition of p185HER-2 tyrosine phosphorylation was affected by the ratio of herstatin to p185HER-2 expression plasmid. The greatest effect was observed at a ratio of 2 to 1 (herstatin: p185HER-2). Transfection of the herstatin plasmid alone reduced the phosphotyrosine signal associated with an endogenous 185 kDa protein by about 2-fold (compare lanes 1 and 2 panel C). The p185 protein co-migrated with p185HER-2 expressed from the transfected p185HER-2 expression plasmid and likely corresponds to endogenous p185HER-2.

Ectopic expression of herstatin reduced the tyrosine phosphorylation of exogenous and endogenous p185HER-2. Furthermore, the ratio of herstatin to p185HER-2 expression plasmid affects the extent of inhibition of p185HER-2 tyrosine phosphorylation and the level of expression of p185. Therefore, reduced p185HER-2 tyrosine phosphorylation was correlated with diminished colony formation of cells co-transfected with HER-2 and herstatin.

EXAMPLE 13

Co-Expression of Herstatin in Transfected Cells (1) Reduced EGF Receptor Levels and Suppressed EGF-Mediated Enhancement of Post-Transfection Cell Survival (2) Inhibited EGF-Mediated EGF Receptor Down-Regulation and (3) Inhibited Activation of EGF Receptors as Determined by Measuring Tyrosine Phosphorylation The group I receptor tyrosine kinases include, in addition to p185HER-2 (erbB-2), the EGF-receptor (HER-1, erbB-1), HER-3 (erbB-3), and HER-4 (erbB-4). The affects of herstatin on the EGF receptor in CHO cells, which do not contain endogenous EGF receptors, were examined to determine if other group I receptors might be affected.

Methods. Measurement of EGF receptor activation. CHO cells at $2\times10^5$ cells/well were plated into 6-well plates and 24 hrs later duplicate wells were transfected with 0.5 µg of FGP marker plasmid, with or without 1.5 µg of EGF receptor expression plasmid, and with the indicated amounts of herstatin expression plasmid. After 24 hours, the cells were twice washed with PBS, and cultured in serum-free media for an additional 24 hrs. The cultures were incubated in the absence or presence of 100 ng/ml of EGF for 20 minutes, and then extracted in modified RIPA as in FIG. 15. Approximately 20 µg of protein from each well was resolved using 7% poly-acrylamide-SDS-gels and analyzed by Western blotting, first with 1 µg/ml of anti-phosphotyrosine antibody. The blot was then stripped and probed with anti-EGF receptor antibody. Alternatively, the cultures were incubated in the absence or presence of 100 ng/ml of EGF for 24 hours, and the cell extracts analyzed by Western blotting and detection with anti-EGF receptor antibody.

Measurement of the effects of the EGF receptor and herstatin on colony growth. CHO cells were plated in 6-well plates and triplicate wells were transfected with 1.5 µg of empty vector, with 1.5 µg of the EGF receptor expression plasmid, with 1.5 µg of the EGF receptor plus 1.5 µg of herstatin plasmid, or with 1.5 µg of herstatin plasmid. Empty vector was added to bring the total amount of DNA to 3 µg in each well. At 48 hrs after DNA was added, the cells in each well were collected by trypsinization and diluted 1:10 into 6-well plates in media containing 600 µg/ml of G418. The media was changed every two days and at 14 days, the cultures were stained with crystal violet. The dye from the stained cultures was extracted as above and quantified by absorbency at 415 nM. The mean value of triplicate wells was determine as a percentage of the control-transfected wells, and the standard deviation was plotted. Similar results were obtained in three separate experiments.

Measurement of stable complex formation between herstatin and p185HER-2 and p175EGF receptors. About 100 µl of a 50% suspension of S-protein agarose (Novagen) was incubated with no peptide, with 50 µg of TBpex14 peptide (provided by Dr. B. Ullman, OHSU), 50 µg of intron 8-encoded peptide, or 50 µg full-length recombinant herstatin at room temperature for 1 hr. Each of these peptides contained an S-protein tag encoded by the pET 30 expression plasmid (Novagen). The agarose samples were twice washed with PBS and incubated at room temperature for 1 hr with 100 µg of A431 cell extract (for the EGF receptor) or 17-3-1 extract (for p185HER-2) solubilized in PBS containing 1% nonidet-p40 (PBSNP-40). After incubation with the cell extracts, the agarose samples were twice washed with 500 Pl of PBS-NP40 and the proteins associated with the resin were eluted at 92° C. for 2 min in 40 µl of SDS sample buffer. To ensure that equal amounts of the original peptides were adhered to the agarose, an aliquot extracted in SDS sample buffer was analyzed by SDS-PAGE and Coomassie staining (a 17% poly-acrylamide gel for TBpex14 and intron 8-encoded peptide, and a10% polyacrylamide gel for p50 herstatin). To analyze receptor binding, an aliquot eluted from the agarose was analyzed by Western blotting and detected using anti-EGFR or anti-p185HER-2.

(1)-(3) Ectopic herstatin expression decreased p175EGF receptor levels in transfected CHO cells, and suppressed EGF-mediated enhancement of post-transfection survival. As described above for the p185HER-2 receptor, FIG. 16 shows that introduction of 2-fold more herstatin plasmid than EGF-receptor plasmid reduced the level of EGF receptor, whether in the presence or absence of the ligand EGF. GFP marker expression was coordinately reduced. When the amount of herstatin plasmid was 3-fold lower than the receptor plasmid, the amount of p175EGF receptor was similar to that in cells transfected with EGF receptor alone (see FIG. 16, lanes 2 and 3, in comparison with lanes 6 and 7).

Figure 17:
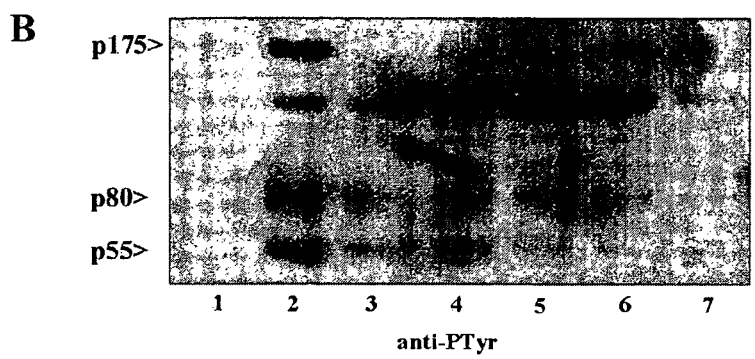

Herstatin expression inhibits p175EGF receptor down-regulation, and p175EGF receptor activation as determined by measurement of tyrosinephosphorylation. The impact of herstatin on EGF activation of the p175EGF receptor was examined. As shown in FIG. 17, Lanes 2 and 3, EGF induced p175EGF receptor tyrosine phosphorylation and enhanced the phosphotyrosine signal associated with proteins of 80 and 55 kDa. In the presence of herstatin, no detectable increase in p175EGF receptor tyrosine phosphorylation, or in the tyrosine phosphorylation of p80 or p55 kDa proteins was observed following addition of saturating amounts of EGF (FIG. 17, lanes 6 and 7).

Figure 18:
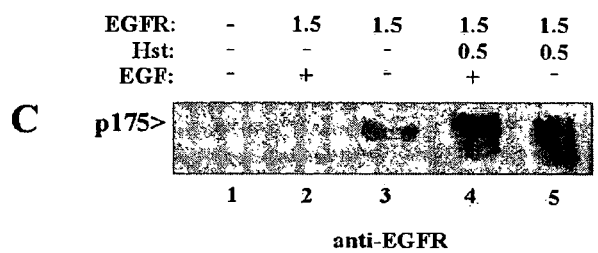
Figure 19:
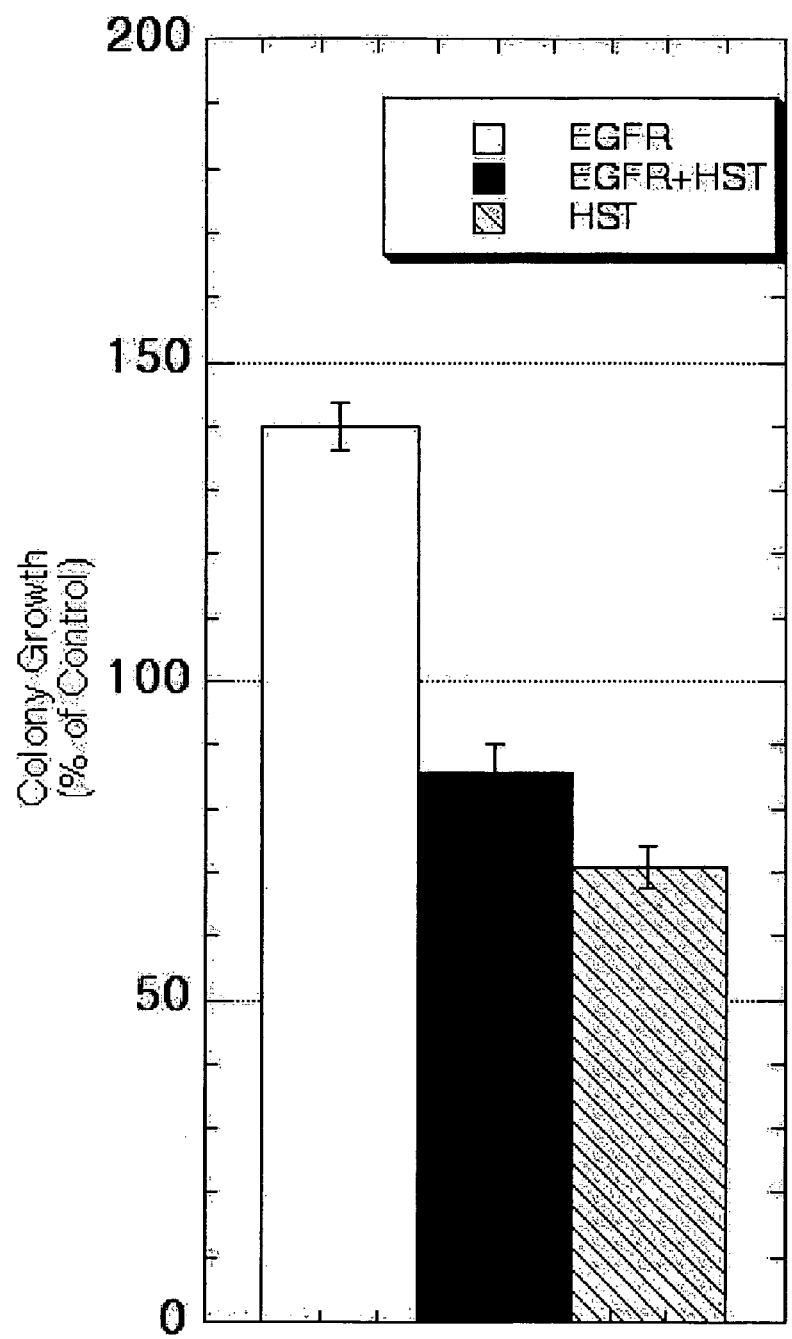
FIG. 19 shows the effects of the EGF receptor alone and in combination with herstatin on colony growth. CHO cells were plated in 6 well plates and triplicate wells were transfected with 1.5 ÿg of empty vector, with 1.5 μg of the EGF receptor expression plasmid, with 1.5 μg of the EGF receptor plus 1.5 μg of herstatin plasmid, or with 1.5 μg of herstatin plasmid. Empty vector was added to bring the total amount of DNA to 3 μg in each well. At 48 hrs after DNA was added, the cells in each well were collected by trypsinization and diluted 1:10 into 6 well plates in media containing 600 μg/ml of G418. The media was changed every two days and at 14 days, the cultures were stained with crystal violet. The dye from the stained cultures was extracted as in FIG. 1 and quantitated by absorbance at 415 nM. The mean value of triplicate wells was determine as the % of the control transfected wells and the standard deviation are plotted. A similar result was obtained in three separate experiments.

An additional known effect of EGF is down-regulation of the EGF-receptor. FIG. 18 shows, as expected that after 48 hrs of treatment with EGF, the level of the p175EGF receptor was greatly reduced (lanes 2 and 3). However, when herstatin was introduced, down-regulation of the EGF receptor was diminished as shown in lanes 4 and 5.

Herstatin inhibits growth of cells that over-express the EGF receptor. The impact of herstatin in combination with the EGF receptor on colony formation was examined. CHO cells were transfected and selected with G418 as in FIG. 11. When the p175EGF receptor alone was over-expressed, there was a 40% increase in the cell survival compared to the effects of the control (empty vector transfected cells as shown in FIG. 11). Herstatin alone caused an approximate 20% reduction in survival of transfected CHO cells compared to the control-transfected cells. This was not significantly different from the effects of herstatin shown in FIG. 11.

Figure 16:
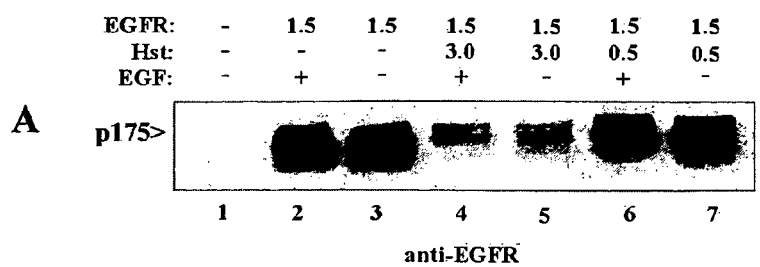
FIGS. 16, 17, and 18 show Herstatin expression inhibits EGF activation of the EGF receptor in transfected cells. CHO cells at $2\times10^5$ cell/well were plated into 6 well plates and 24 hrs later duplicate wells were transfected with 0.5 μg of FGP marker plasmid with or without 1.5 μg of EGF receptor expression plasmid with the indicated amounts of herstatin expression plasmid. At 24 hours, the cells were washed twice with PBS and cultured in serum free media for an additional 24 hrs.

The co-expression of herstatin with the EGF receptor reduced the survival conferred by the EGF receptor alone. As determined above for the p185HER-2 receptor, this inhibition correlated with herstatin-mediated interference with EGF activation of the p175EGF receptor, as shown in FIGS. 16, 17 and 18.

Herstatin Formed a Stable Complex with Both p185HER-2 and EGF Receptors

According to the present invention both full-length herstatin and its intron 8-encoded C-terminal domain (expressed as recombinant peptides) bind to p185 HER-2 with nM-range affinity. Further experiments were performed to determine if there was, in addition to the herstatin/p185HER-2 binding interaction disclosed above, a binding interaction between herstatin and the p175EGF receptor (based on the ability of herstatin to interfere with EGF activation of the EGF receptor).

Herstatin forms a stable complex with both p185HER-2 and the EGF receptor. The herstatin/EGF receptor interaction was examined in a "pull-down" assay using purified intron 8-encoded polypeptide identical to the C-terminus of herstatin, the full-length recombinant herstatin protein, and a control peptide with irrelevant sequence all immobilized on protein S agarose (Novagen). Agarose, derivatized with one of these proteins, was then incubated with extracts of A431 cells, washed, analyzed by Western blotting and detected with antibodies specific for the p175EGF receptor.

The data shown in FIG. 20 show that the p175EGF receptor was specifically associated with intron 8-encoded peptide and with herstatin, but not with the protein S agarose with or without control irrelevant peptide. For comparison, extracts of 17-3-1 cells, which are stably transfected with p185HER-2, were also examined in the pull-down assay. As previously seen using nickle affinity resin (Doherty et al., 1999), p185HER-2 was associated with intron 8-encoded peptide and herstatin, but not to an irrelevant peptide. These results show that both the p175EGF receptor and p185HER-2 are formed a stable complex with herstatin and with its C-terminal intron 8-encoded domain.

In summary, both the p175EGF receptor and p185HER-2 formed a stable complex with herstatin. Herstatin expression strongly inhibited colony formation of cells that over-express p185HER-2. Additionally, herstatin reduced EGF receptor levels, and suppressed the increased cell survival provided by over-expression of the EGF receptor. Diminished cell survival was correlated to a reduction in tyrosine phosphorylation of p185HER-2, and to interference with EGF-mediated activation of the EGF receptor. Thus, the negative regulatory activity of herstatin was extended to a second member of the group I family of receptor tyrosine kinases, the EGF receptor.

We claim:

1. A method for treating a solid tumor characterized by expression of EGF receptor, comprising administering, to a subject in need thereof determined to have a tumor expressing the EGF receptor, an agent that binds to the extracellular domain of EGF receptor, wherein the agent is selected from the group consisting of (a) an isolated polypeptide comprising the amino acid sequence of SEQ ID NOS:11, 15 or 17-26, or fragments thereof of about 50 to 79 contiguous residues in length, wherein the polypeptide binds to the extracellular domain of EGF receptor with an affinity binding constant of at least $10^8$ $M^{-1}$, (b) an isolated and glycosylated polypeptide comprising the amino acid sequence of SEQ ID NOS:12, 38 or 27-36, or fragments thereof of about 80 to 419 contiguous residues in length, wherein the C-terminal 79 contiguous amino acids are present, wherein at least one N-linked glycosylation site is present, and wherein the polypeptide binds to the extracellular domain of EGF receptor with an affinity binding constant of at least $10^8$ $M^{-1}$, (c) a monoclonal antibody that binds to the extracellular domain of EGF receptor, and (d) combinations thereof, with the proviso that where the composition comprises the monoclonal antibody it also comprises at least one of the agents of (a) or (b).

2. The method of claim 1, wherein the solid tumor that expresses EGF receptor is selected from the group consisting of squamous cell carcinoma, lung carcinoma, colon carcinoma, and glial cell tumors.

3. The method of claim 1, wherein the agent is the isolated polypeptide comprising an amino acid sequence selected from the group consisting of SEQ ID NOS:11, 15 and 17-26, and fragments thereof of about 50 to 79 contiguous residues in length, wherein the polypeptide binds to the extracellular domain of EGF receptor with an affinity binding constant of at least $10^8$ $M^{-1}$.

4. The method of claim 1, wherein the agent comprises a combination of the isolated polypeptide comprising an amino acid sequence selected from the group consisting of SEQ ID NOS:11, 15 and 17-26, and fragments thereof of about 50 to 79 contiguous residues in length, wherein the polypeptide binds to the extracellular domain of EGF receptor with an affinity binding constant of at least $10^8$ $M^{-1}$, and the monoclonal antibody that binds to the extracellular domain of EGF receptor.

5. The method of claim 1, wherein the agent is the isolated and glycosylated polypeptide comprising an amino acid sequence selected from the group consisting of SEQ ID NOS: 12, 38 and 27-36, and fragments thereof of about 80 to 419 contiguous residues in length, wherein the C-terminal 79 contiguous amino acids are present, wherein at least one N-linked glycosylation site is present, and wherein the polypeptide binds to the extracellular domain of EGF receptor with an affinity binding constant of at least $10^8$ $M^{-1}$.

6. The method of claim 1, wherein the agent is a combination of the isolated and glycosylated polypeptide comprising an amino acid sequence selected from the group consisting of SEQ ID NOS:12, 38 and 27-36, and fragments thereof of about 80 to 419 contiguous residues in length, wherein the C-terminal 79 contiguous amino acids are present, wherein at least one N-linked glycosylation site is present, and wherein the polypeptide binds to the extracellular domain of EGF receptor with an affinity binding constant of at least $10^8$ $M^{-1}$, and the monoclonal antibody that binds to the extracellular domain of EGF receptor.

7. The method of claim 1, wherein the isolated polypeptide of (a) comprises an amino acid sequence selected from the group consisting of SEQ ID NOS:11, 15 and 17-26.

8. The method of claim 1, wherein the isolated polypeptide of (b) comprises an amino acid sequence selected from the group consisting of SEQ ID NOS:12, 38 and 27-36.

9. The method of claim 1, wherein the isolated polypeptide of (a) consists of an amino acid sequence selected from the group consisting of SEQ ID NOS:11, 15 and 17-26.

10. The method of claim 1, wherein the isolated polypeptide of (b) consists of an amino acid sequence selected from the group consisting of SEQ ID NOS:12, 38 and 27-36.

11. A method for treating a solid tumor characterized by expression of EGF receptor, comprising administering, to a subject in need thereof, an agent that binds to the extracellular domain of EGF receptor; wherein the agent comprises the amino acid sequence of SEQ ID NO:11.

12. A method for treating a solid tumor characterized by expression of EGF receptor, comprising administering, to a subject in need thereof, an agent that binds to the extracellular domain of EGF receptor, wherein the agent comprises the amino acid sequence of SEQ ID NO:12.

13. The method of claim 11, wherein the agent consists of the amino acid sequence of SEQ ID NO:11.

14. The method of claim 12, wherein the agent consists of the amino acid sequence of SEQ ID NO:12.

15. A method for treating a solid tumor characterized by expression of EGF receptor, comprising administering, to a subject in need thereof determined to have a tumor expressing the EGF receptor, an agent that binds to the extracellular domain of EGF receptor, wherein the agent is selected from the group consisting of (a) an isolated polypeptide comprising the amino acid sequence of SEQ ID NO:1, or fragments thereof of about 50 to 79 contiguous residues in length, wherein the polypeptide binds to the extracellular domain of EGF receptor with an affinity binding constant of at least $10^8$ $M^{-1}$, (b) an isolated and glycosylated polypeptide comprising the amino acid sequence of SEQ ID NO:2, or fragments thereof of about 80 to 419 contiguous residues in length, wherein the C-terminal 79 contiguous amino acids are present, wherein at least one N-linked glycosylation site is present, and wherein the polypeptide binds to the extracellular domain of EGF receptor with an affinity binding constant of at least $10^8$ $M^{-1}$, (c) a monoclonal antibody that binds to the extracellular domain of EGF receptor, and (d) combinations thereof, with the proviso that where the composition comprises the monoclonal antibody it also comprises at least one of the agents of (a) or (b).

16. The method of claim 15, wherein the solid tumor that expresses EGF receptor is selected from the group consisting of squamous cell carcinoma, lung carcinoma, colon carcinoma, and glial cell tumors.

17. The method of claim 15, wherein the agent is the isolated polypeptide comprising an amino acid sequence selected from the group consisting of SEQ ID NO 1, and fragments thereof of about 50 to 79 contiguous residues in length, wherein the polypeptide binds to the extracellular domain of EGF receptor with an affinity binding constant of at least $10^8$ $M^{-1}$.

18. The method of claim 15, wherein the agent comprises a combination of the isolated polypeptide comprising an amino acid sequence selected from the group consisting of SEQ ID NO:1, and fragments thereof of about 50 to 79 contiguous residues in length, wherein the polypeptide binds to the extracellular domain of EGF receptor with an affinity binding constant of at least $10^8$ $M^{-1}$, and the monoclonal antibody that binds to the extracellular domain of EGF receptor.

19. The method of claim 15 wherein the agent is the isolated and glycosylated polypeptide comprising an amino acid sequence selected from the group consisting of SEQ ID NO:2, and fragments thereof of about 80 to 419 contiguous residues in length, wherein the C-terminal 79 contiguous amino acids are present, wherein at least one N-linked glycosylation site is present, and wherein the polypeptide binds to the extracellular domain of EGF receptor with an affinity binding constant of at least $10^8$ $M^{-1}$.

20. The method of claim 15, wherein the agent is a combination of the isolated and glycosylated polypeptide comprising an amino acid sequence selected from the group consisting of SEQ ID NO:2, and fragments thereof of about 80 to 419 contiguous residues in length, wherein the C-terminal 79 contiguous amino acids are present, wherein at least one N-linked glycosylation site is present, and wherein the polypeptide binds to the extracellular domain of EGF receptor with an affinity binding constant of at least $10^8$ $M^{-1}$, and the monoclonal antibody that binds to the extracellular domain of EGF receptor.

* * * * *

SEQUENCE LISTING

```
<160> NUMBER OF SEQ ID NOS: 38

<210> SEQ ID NO 1
<211> LENGTH: 79
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Applicants herein disclose Thr and Ser sequence
      variants at this position
<220> FEATURE:
<221> NAME/KEY: MISC_FEATURE
<222> LOCATION: (5)..(5)
<223> OTHER INFORMATION: Applicants herein disclose Leu and Pro sequence
      variants at this position
<220> FEATURE:
<221> NAME/KEY: MISC_FEATURE
<222> LOCATION: (6)..(6)
<223> OTHER INFORMATION: Applicants herein disclose Pro and Leu sequence
      variants at this position
<220> FEATURE:
<221> NAME/KEY: MISC_FEATURE
<222> LOCATION: (16)..(16)
<223> OTHER INFORMATION: Applicants herein disclose Leu and Gln sequence
      variants at this position
<220> FEATURE:
<221> NAME/KEY: MISC_FEATURE
<222> LOCATION: (18)..(18)
```

<223> OTHER INFORMATION: Applicants herein disclose Met and Leu sequence
      variants at this position
<220> FEATURE:
<221> NAME/KEY: MISC_FEATURE
<222> LOCATION: (21)..(21)
<223> OTHER INFORMATION: Applicants herein disclose Gly, Asp, Ala and
      Val sequence variants at this position
<220> FEATURE:
<221> NAME/KEY: MISC_FEATURE
<222> LOCATION: (36)..(36)
<223> OTHER INFORMATION: Applicants herein disclose Leu and Ile sequence
      variants at this position
<220> FEATURE:
<221> NAME/KEY: MISC_FEATURE
<222> LOCATION: (54)..(54)
<223> OTHER INFORMATION: Applicants herein disclose Pro and Arg sequence
      variants at this position
<220> FEATURE:
<221> NAME/KEY: MISC_FEATURE
<222> LOCATION: (64)..(64)
<223> OTHER INFORMATION: Applicants herein disclose Pro and Leu sequence
      variants at this position
<220> FEATURE:
<221> NAME/KEY: MISC_FEATURE
<222> LOCATION: (73)..(73)
<223> OTHER INFORMATION: Applicants herein disclose Asp and Asn sequence
      variants at this position

<400> SEQUENCE: 1

Gly Xaa His Ser Xaa Xaa Pro Arg Pro Ala Ala Val Pro Val Pro Xaa
1               5                   10                  15

Arg Xaa Gln Pro Xaa Pro Ala His Pro Val Leu Ser Phe Leu Arg Pro
            20                  25                  30

Ser Trp Asp Xaa Val Ser Ala Phe Tyr Ser Leu Pro Leu Ala Pro Leu
        35                  40                  45

Ser Pro Thr Ser Val Xaa Ile Ser Pro Val Ser Val Gly Arg Gly Xaa
    50                  55                  60

Asp Pro Asp Ala His Val Ala Val Xaa Leu Ser Arg Tyr Glu Gly
65                  70                  75

<210> SEQ ID NO 2
<211> LENGTH: 419
<212> TYPE: PRT
<213> ORGANISM: Homo sapiens
<220> FEATURE:
<221> NAME/KEY: MISC_FEATURE
<222> LOCATION: (342)..(342)
<223> OTHER INFORMATION: Applicants herein disclose Thr and Ser sequence
      variants at this position
<220> FEATURE:
<221> NAME/KEY: MISC_FEATURE
<222> LOCATION: (345)..(345)
<223> OTHER INFORMATION: Applicants herein disclose Leu and Pro sequence
      variants at this position
<220> FEATURE:
<221> NAME/KEY: MISC_FEATURE
<222> LOCATION: (346)..(346)
<223> OTHER INFORMATION: Applicants herein disclose Pro and Leu sequence
      variants at this position
<220> FEATURE:
<221> NAME/KEY: MISC_FEATURE
<222> LOCATION: (356)..(356)
<223> OTHER INFORMATION: Applicants herein disclose Leu and Gln sequence
      variants at this position
<220> FEATURE:
<221> NAME/KEY: MISC_FEATURE
<222> LOCATION: (358)..(358)
<223> OTHER INFORMATION: Applicants herein disclose Met and Leu sequence
      variants at this position
<220> FEATURE:
<221> NAME/KEY: MISC_FEATURE
<222> LOCATION: (361)..(361)
<223> OTHER INFORMATION: Applicants herein disclose Gly, Asp, Ala and

```
        Val sequence variants at this position
<220> FEATURE:
<221> NAME/KEY: MISC_FEATURE
<222> LOCATION: (376)..(376)
<223> OTHER INFORMATION: Applicants herein disclose Leu and Ile sequence
      variants at this position
<220> FEATURE:
<221> NAME/KEY: MISC_FEATURE
<222> LOCATION: (394)..(394)
<223> OTHER INFORMATION: Applicants herein disclose Pro and Arg sequence
      variants at this position
<220> FEATURE:
<221> NAME/KEY: MISC_FEATURE
<222> LOCATION: (404)..(404)
<223> OTHER INFORMATION: Applicants herein disclose Pro and Leu sequence
      variants at this position
<220> FEATURE:
<221> NAME/KEY: MISC_FEATURE
<222> LOCATION: (413)..(413)
<223> OTHER INFORMATION: Applicants herein disclose Asp and Asn sequence
      variants at this position

<400> SEQUENCE: 2

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
```

```
                290               295              300
    Ser Thr Asp Val Gly Ser Cys Thr Leu Val Cys Pro Leu His Asn Gln
    305                 310              315                  320

Glu Val Thr Ala Glu Asp Gly Thr Gln Arg Cys Glu Lys Cys Ser Lys
                    325              330                  335

Pro Cys Ala Arg Gly Xaa His Ser Xaa Xaa Pro Arg Pro Ala Ala Val
                    340              345              350

Pro Val Pro Xaa Arg Xaa Gln Pro Xaa Pro Ala His Pro Val Leu Ser
                355              360                  365

Phe Leu Arg Pro Ser Trp Asp Xaa Val Ser Ala Phe Tyr Ser Leu Pro
        370              375              380

Leu Ala Pro Leu Ser Pro Thr Ser Val Xaa Ile Ser Pro Val Ser Val
    385              390              395                  400

Gly Arg Gly Xaa Asp Pro Asp Ala His Val Ala Val Xaa Leu Ser Arg
                    405              410              415

Tyr Glu Gly

<210> SEQ ID NO 3
<211> LENGTH: 19
<212> TYPE: DNA
<213> ORGANISM: Artificial Sequence
<220> FEATURE:
<223> OTHER INFORMATION: HER-2-specific oligonucleotide primer

<400> SEQUENCE: 3
tgagcaccat ggagctggc                                              19

<210> SEQ ID NO 4
<211> LENGTH: 22
<212> TYPE: DNA
<213> ORGANISM: Artificial Sequence
<220> FEATURE:
<223> OTHER INFORMATION: HER-2-specific oligonucleotide primer

<400> SEQUENCE: 4
tccggcagaa atgccaggct cc                                          22

<210> SEQ ID NO 5
<211> LENGTH: 22
<212> TYPE: DNA
<213> ORGANISM: Artificial Sequence
<220> FEATURE:
<223> OTHER INFORMATION: HER-2 cDNA-specific oligonucleotide primer

<400> SEQUENCE: 5
aacacagcgg tgtgagaagt gc                                          22

<210> SEQ ID NO 6
<211> LENGTH: 21
<212> TYPE: DNA
<213> ORGANISM: Artificial Sequence
<220> FEATURE:
<223> OTHER INFORMATION: HER-2 ECDIIIa-region-specific oligonucleotide
      primer

<400> SEQUENCE: 6
ataccgggac aggtcaacag c                                           21

<210> SEQ ID NO 7
<211> LENGTH: 20
<212> TYPE: DNA
<213> ORGANISM: Artificial Sequence
```

```
<220> FEATURE:
<223> OTHER INFORMATION: HER-2 ECDIIIa-region-specific oligonucleotide
      primer

<400> SEQUENCE: 7
tctgggtacc cactcactgc                                                    20

<210> SEQ ID NO 8
<211> LENGTH: 22
<212> TYPE: DNA
<213> ORGANISM: Artificial Sequence
<220> FEATURE:
<223> OTHER INFORMATION: HER-2 exon-specific oligonucleotide primer

<400> SEQUENCE: 8
ttcacactgg cacgtccaga cc                                                 22

<210> SEQ ID NO 9
<211> LENGTH: 27
<212> TYPE: DNA
<213> ORGANISM: Artificial Sequence
<220> FEATURE:
<223> OTHER INFORMATION: HER-2 cDNA-specific oligonucleotide primer

<400> SEQUENCE: 9
gcacggatcc atagcagact gaggagg                                            27

<210> SEQ ID NO 10
<211> LENGTH: 240
<212> TYPE: DNA
<213> ORGANISM: Homo sapiens
<220> FEATURE:
<221> NAME/KEY: exon
<222> LOCATION: (1)..(240)
<223> OTHER INFORMATION: ECDIIIa region coding sequence
<220> FEATURE:
<221> NAME/KEY: misc_feature
<222> LOCATION: (62)..(62)
<223> OTHER INFORMATION: Applicants disclose C, T, A and G variants at
      this position

<400> SEQUENCE: 10 ggt wcc cac tca cyg cyc ccg agg cca gct gca gtt cct gtc cct cwg         48
Gly Xaa His Ser Xaa Xaa Pro Arg Pro Ala Ala Val Pro Val Pro Xaa
1               5                   10                  15 cgc mtg cag cct gnc cca gcc cac cct gtc cta tcc ttc ctc aga ccc         96
Arg Xaa Gln Pro Xaa Pro Ala His Pro Val Leu Ser Phe Leu Arg Pro
            20                  25                  30 tct tgg gac mta gtc tct gcc ttc tac tct cta ccc ctg gcc ccc ctc        144
Ser Trp Asp Xaa Val Ser Ala Phe Tyr Ser Leu Pro Leu Ala Pro Leu
        35                  40                  45 agc cct aca agt gtc cst ata tcc cct gtc agt gtg ggg agg ggc cyg        192
Ser Pro Thr Ser Val Xaa Ile Ser Pro Val Ser Val Gly Arg Gly Xaa
    50                  55                  60 gac cct gat gct cat gtg gct gtt rac ctg tcc cgg tat gaa ggc tga        240
Asp Pro Asp Ala His Val Ala Val Xaa Leu Ser Arg Tyr Glu Gly
65                  70                  75

<210> SEQ ID NO 11
<211> LENGTH: 79
<212> TYPE: PRT
<213> ORGANISM: Homo sapiens

<400> SEQUENCE: 11

Gly Thr His Ser Leu Pro Pro Arg Pro Ala Ala Val Pro Val Pro Leu
1               5                   10                  15
```

```
Arg Met Gln Pro Gly Pro Ala His Pro Val Leu Ser Phe Leu Arg Pro
            20                  25                  30

Ser Trp Asp Leu Val Ser Ala Phe Tyr Ser Leu Pro Leu Ala Pro Leu
        35                  40                  45

Ser Pro Thr Ser Val Pro Ile Ser Pro Val Ser Val Gly Arg Gly Pro
        50                  55                  60

Asp Pro Asp Ala His Val Ala Val Asp Leu Ser Arg Tyr Glu Gly
65                  70                  75

<210> SEQ ID NO 12
<211> LENGTH: 419
<212> TYPE: PRT
<213> ORGANISM: Homo sapiens

<400> SEQUENCE: 12

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
```

```
                305                 310                 315                 320
Glu Val Thr Ala Glu Asp Gly Thr Gln Arg Cys Glu Lys Cys Ser Lys
                    325                 330                 335
Pro Cys Ala Arg Gly Thr His Ser Leu Pro Pro Arg Pro Ala Ala Val
                340                 345                 350
Pro Val Pro Leu Arg Met Gln Pro Gly Pro Ala His Pro Val Leu Ser
            355                 360                 365
Phe Leu Arg Pro Ser Trp Asp Leu Val Ser Ala Phe Tyr Ser Leu Pro
        370                 375                 380
Leu Ala Pro Leu Ser Pro Thr Ser Val Pro Ile Ser Pro Val Ser Val
385                 390                 395                 400
Gly Arg Gly Pro Asp Pro Asp Ala His Val Ala Val Asp Leu Ser Arg
                405                 410                 415
Tyr Glu Gly

<210> SEQ ID NO 13
<211> LENGTH: 287
<212> TYPE: DNA
<213> ORGANISM: Homo sapiens

<400> SEQUENCE: 13
cccgaggtac ccactcactg ctcccgaggc cagctgcagt tcctgtccct ctgcgcatgc      60
agcctggccc agcccaccct gtcctatcct tcctcagacc ctcttgggac ctagtctctg     120
ccttctactc tctaccccctg gccccccctca gccccacaag tgtccctata tcccctgtca    180
gtgtggggag gggcccggac cctgatgctc atgtggctgt taacctgtcc cggtatgaag     240
gctgagacgg ccccttcccc cacccacccc cacctcctca gtgtgct                   287

<210> SEQ ID NO 14
<211> LENGTH: 276
<212> TYPE: DNA
<213> ORGANISM: Homo sapiens

<400> SEQUENCE: 14
ggtacccact cactgctccc gaggccagct gcagttcctg tccctctgcg catgcagcct      60
ggcccagccc accctgtcct atccttcctc agaccctctt gggacctagt ctctgccttc     120
tactctctac ccctggcccc cctcagcccc acaagtgtcc ctatatcccc tgtcagtgtg     180
ggagggggcc cggaccctga tgctcatgtg gctgttaacc tgtcccggta tgaaggctga     240
gacggcccct tccccaccc accccacct cctcag                                 276

<210> SEQ ID NO 15
<211> LENGTH: 79
<212> TYPE: PRT
<213> ORGANISM: Homo sapiens

<400> SEQUENCE: 15

Gly Thr His Ser Leu Leu Pro Arg Pro Ala Ala Val Pro Val Pro Leu
1               5                   10                  15
Arg Met Gln Pro Gly Pro Ala His Pro Val Leu Ser Phe Leu Arg Pro
                20                  25                  30
Ser Trp Asp Leu Val Ser Ala Phe Tyr Ser Leu Pro Leu Ala Pro Leu
            35                  40                  45
Ser Pro Thr Ser Val Pro Ile Ser Pro Val Ser Val Gly Arg Gly Pro
        50                  55                  60
Asp Pro Asp Ala His Val Ala Val Asn Leu Ser Arg Tyr Glu Gly
```

-continued

```
65                    70                  75

<210> SEQ ID NO 16
<211> LENGTH: 240
<212> TYPE: DNA
<213> ORGANISM: Homo sapiens

<400> SEQUENCE: 16
ggtacccact cactgccccc gaggccagct gcagttcctg tccctctgcg catgcagcct    60
ggcccagccc accctgtcct atccttcctc agaccctctt gggacctagt ctctgccttc   120
tactctctac ccctggcccc cctcagccct acaagtgtcc ctatatcccc tgtcagtgtg   180
gggaggggcc cggaccctga tgctcatgtg gctgttgacc tgtcccggta tgaaggctga   240

<210> SEQ ID NO 17
<211> LENGTH: 79
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Applicants disclose Thr and Ser sequence
      variants at this position

<400> SEQUENCE: 17

Gly Xaa His Ser Leu Pro Pro Arg Pro Ala Ala Val Pro Val Pro Leu
1               5                   10                  15

Arg Met Gln Pro Gly Pro Ala His Pro Val Leu Ser Phe Leu Arg Pro
                20                  25                  30

Ser Trp Asp Leu Val Ser Ala Phe Tyr Ser Leu Pro Leu Ala Pro Leu
            35                  40                  45

Ser Pro Thr Ser Val Pro Ile Ser Pro Val Ser Val Gly Arg Gly Pro
        50                  55                  60

Asp Pro Asp Ala His Val Ala Val Asp Leu Ser Arg Tyr Glu Gly
65                  70                  75

<210> SEQ ID NO 18
<211> LENGTH: 79
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Applicants disclose Leu and Pro variants at
      this position

<400> SEQUENCE: 18

Gly Thr His Ser Xaa Pro Pro Arg Pro Ala Ala Val Pro Val Pro Leu
1               5                   10                  15

Arg Met Gln Pro Gly Pro Ala His Pro Val Leu Ser Phe Leu Arg Pro
                20                  25                  30

Ser Trp Asp Leu Val Ser Ala Phe Tyr Ser Leu Pro Leu Ala Pro Leu
            35                  40                  45

Ser Pro Thr Ser Val Pro Ile Ser Pro Val Ser Val Gly Arg Gly Pro
        50                  55                  60

Asp Pro Asp Ala His Val Ala Val Asp Leu Ser Arg Tyr Glu Gly
65                  70                  75

<210> SEQ ID NO 19
<211> LENGTH: 79
<212> TYPE: PRT
<213> ORGANISM: Homo sapiens
```

```
<220> FEATURE:
<221> NAME/KEY: MISC_FEATURE
<222> LOCATION: (6)..(6)
<223> OTHER INFORMATION: Applicants disclose Pro and Leu variants at
      this position

<400> SEQUENCE: 19

Gly Thr His Ser Leu Xaa Pro Arg Pro Ala Ala Val Pro Val Pro Leu
1               5                   10                  15

Arg Met Gln Pro Gly Pro Ala His Pro Val Leu Ser Phe Leu Arg Pro
            20                  25                  30

Ser Trp Asp Leu Val Ser Ala Phe Tyr Ser Leu Pro Leu Ala Pro Leu
        35                  40                  45

Ser Pro Thr Ser Val Pro Ile Ser Pro Val Ser Val Gly Arg Gly Pro
    50                  55                  60

Asp Pro Asp Ala His Val Ala Val Asp Leu Ser Arg Tyr Glu Gly
65                  70                  75

<210> SEQ ID NO 20
<211> LENGTH: 79
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: Applicants disclose Leu and Gln variants at
      this position

<400> SEQUENCE: 20

Gly Thr His Ser Leu Pro Pro Arg Pro Ala Ala Val Pro Val Pro Xaa
1               5                   10                  15

Arg Met Gln Pro Gly Pro Ala His Pro Val Leu Ser Phe Leu Arg Pro
            20                  25                  30

Ser Trp Asp Leu Val Ser Ala Phe Tyr Ser Leu Pro Leu Ala Pro Leu
        35                  40                  45

Ser Pro Thr Ser Val Pro Ile Ser Pro Val Ser Val Gly Arg Gly Pro
    50                  55                  60

Asp Pro Asp Ala His Val Ala Val Asp Leu Ser Arg Tyr Glu Gly
65                  70                  75

<210> SEQ ID NO 21
<211> LENGTH: 79
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: Applicants disclose Met and Leu variants at
      this position

<400> SEQUENCE: 21

Gly Thr His Ser Leu Pro Pro Arg Pro Ala Ala Val Pro Val Pro Leu
1               5                   10                  15

Arg Xaa Gln Pro Gly Pro Ala His Pro Val Leu Ser Phe Leu Arg Pro
            20                  25                  30

Ser Trp Asp Leu Val Ser Ala Phe Tyr Ser Leu Pro Leu Ala Pro Leu
        35                  40                  45

Ser Pro Thr Ser Val Pro Ile Ser Pro Val Ser Val Gly Arg Gly Pro
    50                  55                  60

Asp Pro Asp Ala His Val Ala Val Asp Leu Ser Arg Tyr Glu Gly
65                  70                  75
```

```
<210> SEQ ID NO 22
<211> LENGTH: 79
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: Applicants disclose Gly, Asp, Ala and Val
      variants at this position

<400> SEQUENCE: 22

Gly Thr His Ser Leu Pro Pro Arg Pro Ala Ala Val Pro Val Pro Leu
1               5                   10                  15

Arg Met Gln Pro Xaa Pro Ala His Pro Val Leu Ser Phe Leu Arg Pro
            20                  25                  30

Ser Trp Asp Leu Val Ser Ala Phe Tyr Ser Leu Pro Leu Ala Pro Leu
        35                  40                  45

Ser Pro Thr Ser Val Pro Ile Ser Pro Val Ser Val Gly Arg Gly Pro
    50                  55                  60

Asp Pro Asp Ala His Val Ala Val Asp Leu Ser Arg Tyr Glu Gly
65                  70                  75

<210> SEQ ID NO 23
<211> LENGTH: 79
<212> TYPE: PRT
<213> ORGANISM: Homo sapiens
<220> FEATURE:
<221> NAME/KEY: MISC_FEATURE
<222> LOCATION: (36)..(36)
<223> OTHER INFORMATION: Applicants disclose Leu and Ile variants at
      this position

<400> SEQUENCE: 23

Gly Thr His Ser Leu Pro Pro Arg Pro Ala Ala Val Pro Val Pro Leu
1               5                   10                  15

Arg Met Gln Pro Gly Pro Ala His Pro Val Leu Ser Phe Leu Arg Pro
            20                  25                  30

Ser Trp Asp Xaa Val Ser Ala Phe Tyr Ser Leu Pro Leu Ala Pro Leu
        35                  40                  45

Ser Pro Thr Ser Val Pro Ile Ser Pro Val Ser Val Gly Arg Gly Pro
    50                  55                  60

Asp Pro Asp Ala His Val Ala Val Asp Leu Ser Arg Tyr Glu Gly
65                  70                  75

<210> SEQ ID NO 24
<211> LENGTH: 79
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: Applicants disclose Pro and Arg variants at
      this position

<400> SEQUENCE: 24

Gly Thr His Ser Leu Pro Pro Arg Pro Ala Ala Val Pro Val Pro Leu
1               5                   10                  15

Arg Met Gln Pro Gly Pro Ala His Pro Val Leu Ser Phe Leu Arg Pro
            20                  25                  30

Ser Trp Asp Leu Val Ser Ala Phe Tyr Ser Leu Pro Leu Ala Pro Leu
        35                  40                  45

Ser Pro Thr Ser Val Xaa Ile Ser Pro Val Ser Val Gly Arg Gly Pro
```

```
                   50                  55                  60

Asp Pro Asp Ala His Val Ala Val Asp Leu Ser Arg Tyr Glu Gly
 65                  70                  75

<210> SEQ ID NO 25
<211> LENGTH: 79
<212> TYPE: PRT
<213> ORGANISM: Homo sapiens
<220> FEATURE:
<221> NAME/KEY: MISC_FEATURE
<222> LOCATION: (64)..(64)
<223> OTHER INFORMATION: Applicants disclose Pro and Leu variants at
      this position

<400> SEQUENCE: 25

Gly Thr His Ser Leu Pro Pro Arg Pro Ala Ala Val Pro Val Pro Leu
 1               5                  10                  15

Arg Met Gln Pro Gly Pro Ala His Pro Val Leu Ser Phe Leu Arg Pro
                20                  25                  30

Ser Trp Asp Leu Val Ser Ala Phe Tyr Ser Leu Pro Leu Ala Pro Leu
            35                  40                  45

Ser Pro Thr Ser Val Pro Ile Ser Pro Val Ser Val Gly Arg Gly Xaa
        50                  55                  60

Asp Pro Asp Ala His Val Ala Val Asp Leu Ser Arg Tyr Glu Gly
 65                  70                  75

<210> SEQ ID NO 26
<211> LENGTH: 79
<212> TYPE: PRT
<213> ORGANISM: Homo sapiens
<220> FEATURE:
<221> NAME/KEY: MISC_FEATURE
<222> LOCATION: (73)..(73)
<223> OTHER INFORMATION: Applicants disclose Asp and Asn variants at
      this position

<400> SEQUENCE: 26

Gly Thr His Ser Leu Pro Pro Arg Pro Ala Ala Val Pro Val Pro Leu
 1               5                  10                  15

Arg Met Gln Pro Gly Pro Ala His Pro Val Leu Ser Phe Leu Arg Pro
                20                  25                  30

Ser Trp Asp Leu Val Ser Ala Phe Tyr Ser Leu Pro Leu Ala Pro Leu
            35                  40                  45

Ser Pro Thr Ser Val Pro Ile Ser Pro Val Ser Val Gly Arg Gly Pro
        50                  55                  60

Asp Pro Asp Ala His Val Ala Val Xaa Leu Ser Arg Tyr Glu Gly
 65                  70                  75

<210> SEQ ID NO 27
<211> LENGTH: 419
<212> TYPE: PRT
<213> ORGANISM: Homo sapiens
<220> FEATURE:
<221> NAME/KEY: MISC_FEATURE
<222> LOCATION: (342)..(342)
<223> OTHER INFORMATION: Applicants disclose Thr and Ser variants at
      this position

<400> SEQUENCE: 27

Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                20                  25                  30
```

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Xaa His Ser Leu Pro Pro Arg Pro Ala Ala Val
            340                 345                 350

Pro Val Pro Leu Arg Met Gln Pro Gly Pro Ala His Pro Val Leu Ser
        355                 360                 365

Phe Leu Arg Pro Ser Trp Asp Leu Val Ser Ala Phe Tyr Ser Leu Pro
    370                 375                 380

Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Asp Leu Ser Arg
                405                 410                 415

Tyr Glu Gly

<210> SEQ ID NO 28
<211> LENGTH: 419
<212> TYPE: PRT

-continued

```
<213> ORGANISM: Homo sapiens
<220> FEATURE:
<221> NAME/KEY: MISC_FEATURE
<222> LOCATION: (345)..(345)
<223> OTHER INFORMATION: Applicant disclose Leu and Pro variants at
      this position

<400> SEQUENCE: 28
```

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Xaa Pro Pro Arg Pro Ala Ala Val
            340                 345                 350

Pro Val Pro Leu Arg Met Gln Pro Gly Pro Ala His Pro Val Leu Ser
        355                 360                 365

Phe Leu Arg Pro Ser Trp Asp Leu Val Ser Ala Phe Tyr Ser Leu Pro

```
                370                 375                 380
Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Asp Leu Ser Arg
                405                 410                 415

Tyr Glu Gly

<210> SEQ ID NO 29
<211> LENGTH: 419
<212> TYPE: PRT
<213> ORGANISM: Homo sapiens
<220> FEATURE:
<221> NAME/KEY: MISC_FEATURE
<222> LOCATION: (346)..(346)
<223> OTHER INFORMATION: Applicants disclose Pro and Leu variants at
      this position

<400> SEQUENCE: 29

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300
```

```
Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Leu Xaa Pro Arg Pro Ala Ala Val
            340                 345                 350

Pro Val Pro Leu Arg Met Gln Pro Gly Pro Ala His Pro Val Leu Ser
        355                 360                 365

Phe Leu Arg Pro Ser Trp Asp Leu Val Ser Ala Phe Tyr Ser Leu Pro
    370                 375                 380

Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Asp Leu Ser Arg
                405                 410                 415

Tyr Glu Gly

<210> SEQ ID NO 30
<211> LENGTH: 419
<212> TYPE: PRT
<213> ORGANISM: Homo sapiens
<220> FEATURE:
<221> NAME/KEY: MISC_FEATURE
<222> LOCATION: (356)..(356)
<223> OTHER INFORMATION: Applicants disclose Leu and Gln variants at
      this position

<400> SEQUENCE: 30

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Leu Pro Arg Pro Ala Ala Val
            340                 345                 350

Pro Val Pro Xaa Arg Met Gln Pro Gly Pro Ala His Pro Val Leu Ser
            355                 360                 365

Phe Leu Arg Pro Ser Trp Asp Leu Val Ser Ala Phe Tyr Ser Leu Pro
    370                 375                 380

Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Asp Leu Ser Arg
                405                 410                 415

Tyr Glu Gly

<210> SEQ ID NO 31
<211> LENGTH: 419
<212> TYPE: PRT
<213> ORGANISM: Homo sapiens
<220> FEATURE:
<221> NAME/KEY: MISC_FEATURE
<222> LOCATION: (358)..(358)
<223> OTHER INFORMATION: Applicants disclose Met and Leu variants at
      this position

<400> SEQUENCE: 31

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
```

-continued

```
                145                 150                 155                 160
Leu Cys Tyr Gln Asp Thr Ile Leu Trp Lys Asp Ile Phe His Lys Asn
                    165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
        210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Leu Pro Pro Arg Pro Ala Ala Val
                340                 345                 350

Pro Val Pro Leu Arg Xaa Gln Pro Gly Pro Ala His Pro Val Leu Ser
            355                 360                 365

Phe Leu Arg Pro Ser Trp Asp Leu Val Ser Ala Phe Tyr Ser Leu Pro
        370                 375                 380

Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Asp Leu Ser Arg
                405                 410                 415

Tyr Glu Gly

<210> SEQ ID NO 32
<211> LENGTH: 419
<212> TYPE: PRT
<213> ORGANISM: Homo sapiens
<220> FEATURE:
<221> NAME/KEY: MISC_FEATURE
<222> LOCATION: (361)..(361)
<223> OTHER INFORMATION: Applicants disclose Gly, Asp, Ala and Val
      variants at this position

<400> SEQUENCE: 32

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80
```

```
Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
            165                 170                 175

Asn Gln Leu Ala Leu Thr Leu Ile Asp Thr Asn Arg Ser Arg Ala Cys
        180                 185                 190

His Pro Cys Ser Pro Met Cys Lys Gly Ser Arg Cys Trp Gly Glu Ser
    195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Gly Thr His Ser Leu Pro Arg Pro Ala Ala Val
        340                 345                 350

Pro Val Pro Leu Arg Met Gln Pro Xaa Pro Ala His Pro Val Leu Ser
    355                 360                 365

Phe Leu Arg Pro Ser Trp Asp Leu Val Ser Ala Phe Tyr Ser Leu Pro
370                 375                 380

Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Asp Leu Ser Arg
            405                 410                 415

Tyr Glu Gly

<210> SEQ ID NO 33
<211> LENGTH: 419
<212> TYPE: PRT
<213> ORGANISM: Homo sapiens
<220> FEATURE:
<221> NAME/KEY: MISC_FEATURE
<222> LOCATION: (376)..(376)
<223> OTHER INFORMATION: Applicant disclose Leu and Ile variants at this
      position

<400> SEQUENCE: 33
```

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Leu Pro Pro Arg Pro Ala Ala Val
            340                 345                 350

Pro Val Pro Leu Arg Met Gln Pro Gly Pro Ala His Pro Val Leu Ser
        355                 360                 365

Phe Leu Arg Pro Ser Trp Asp Xaa Val Ser Ala Phe Tyr Ser Leu Pro
    370                 375                 380

Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Asp Leu Ser Arg
                405                 410                 415

Tyr Glu Gly
```

<210> SEQ ID NO 34
<211> LENGTH: 419
<212> TYPE: PRT
<213> ORGANISM: Homo sapiens
<220> FEATURE:
<221> NAME/KEY: MISC_FEATURE
<222> LOCATION: (394)..(394)
<223> OTHER INFORMATION: Applicants disclose Pro and Arg variants at
      this position

<400> SEQUENCE: 34

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Leu Pro Pro Arg Pro Ala Ala Val
            340                 345                 350

```
Pro Val Pro Leu Arg Met Gln Pro Gly Pro Ala His Pro Val Leu Ser
            355                 360                 365

Phe Leu Arg Pro Ser Trp Asp Leu Val Ser Ala Phe Tyr Ser Leu Pro
            370                 375                 380

Leu Ala Pro Leu Ser Pro Thr Ser Val Xaa Ile Ser Pro Val Ser Val
385                 390                 395                 400

Gly Arg Gly Pro Asp Pro Asp Ala His Val Ala Val Asp Leu Ser Arg
            405                 410                 415

Tyr Glu Gly

<210> SEQ ID NO 35
<211> LENGTH: 419
<212> TYPE: PRT
<213> ORGANISM: Homo sapiens
<220> FEATURE:
<221> NAME/KEY: MISC_FEATURE
<222> LOCATION: (404)..(404)
<223> OTHER INFORMATION: Applicants disclose Pro and Leu variants at
      this position

<400> SEQUENCE: 35

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270
```

```
Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Leu Pro Pro Arg Pro Ala Ala Val
            340                 345                 350

Pro Val Pro Leu Arg Met Gln Pro Gly Pro Ala His Pro Val Leu Ser
        355                 360                 365

Phe Leu Arg Pro Ser Trp Asp Leu Val Ser Ala Phe Tyr Ser Leu Pro
    370                 375                 380

Leu Ala Pro Leu Ser Pro Thr Ser Val Pro Ile Ser Pro Val Ser Val
385                 390                 395                 400

Gly Arg Gly Xaa Asp Pro Asp Ala His Val Ala Val Asp Leu Ser Arg
                405                 410                 415

Tyr Glu Gly

<210> SEQ ID NO 36
<211> LENGTH: 419
<212> TYPE: PRT
<213> ORGANISM: Homo sapiens
<220> FEATURE:
<221> NAME/KEY: MISC_FEATURE
<222> LOCATION: (413)..(413)
<223> OTHER INFORMATION: Applicants disclose Asp and Asn variants at
      this position

<400> SEQUENCE: 36

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
```

-continued

```
            195                 200                 205
Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Leu Pro Arg Pro Ala Ala Val
            340                 345                 350

Pro Val Pro Leu Arg Met Gln Pro Gly Pro Ala His Pro Val Leu Ser
        355                 360                 365

Phe Leu Arg Pro Ser Trp Asp Leu Val Ser Ala Phe Tyr Ser Leu Pro
    370                 375                 380

Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Xaa Leu Ser Arg
                405                 410                 415

Tyr Glu Gly
```

```
<210> SEQ ID NO 37
<211> LENGTH: 1255
<212> TYPE: PRT
<213> ORGANISM: Homo sapiens
<300> PUBLICATION INFORMATION:
<301> AUTHORS: Coussens,L., Yang-Feng,T.L., Liao,Y.-C., Chen,E.,
      Gray,A.,
<302> TITLE: Tyrosine kinase receptor with extensive homology to EGF
      receptor
<303> JOURNAL: Science
<304> VOLUME: 230
<305> ISSUE: 4730
<306> PAGES: 1132-1139
<307> DATE: 1985-06-12

<400> SEQUENCE: 37

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95
```

-continued

```
Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Thr Thr Pro
        115                 120                 125

Val Thr Gly Ala Ser Pro Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
                195                 200                 205

Ser Glu Asp Cys Gln Ser Leu Thr Arg Thr Val Cys Ala Gly Gly Cys
        210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
```

-continued

```
            515                 520                 525
Val Asn Cys Ser Gln Phe Leu Arg Gly Gln Glu Cys Val Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
        770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
        930                 935                 940
```

```
Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Ala Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 38
<211> LENGTH: 419
<212> TYPE: PRT
<213> ORGANISM: Homo sapiens

<400> SEQUENCE: 38

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
```

-continued

```
              35                  40                  45
Leu Tyr Gln Gly Cys Gln Val Val Gln Gly Asn Leu Glu Leu Thr Tyr
    50                  55                  60
Leu Pro Thr Asn Ala Ser Leu Ser Phe Leu Gln Asp Ile Gln Glu Val
65                  70                  75                  80
Gln Gly Tyr Val Leu Ile Ala His Asn Gln Val Arg Gln Val Pro Leu
                85                  90                  95
Gln Arg Leu Arg Ile Val Arg Gly Thr Gln Leu Phe Glu Asp Asn Tyr
                100                 105                 110
Ala Leu Ala Val Leu Asp Asn Gly Asp Pro Leu Asn Asn Thr Thr Pro
                115                 120                 125
Val Thr Gly Ala Ser Pro Gly Gly Leu Arg Glu Leu Gln Leu Arg Ser
    130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
                180                 185                 190
His Pro Cys Ser Pro Met Cys Lys Gly Ser Arg Cys Trp Gly Glu Ser
                195                 200                 205
Ser Glu Asp Cys Gln Ser Leu Thr Arg Thr Val Cys Ala Gly Gly Cys
                210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
                275                 280                 285
Tyr Thr Phe Gly Ala Ser Cys Val Thr Ala Cys Pro Tyr Asn Tyr Leu
                290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Gly Thr His Ser Leu Leu Pro Arg Pro Ala Ala Val
                340                 345                 350
Pro Val Pro Leu Arg Met Gln Pro Gly Pro Ala His Pro Val Leu Ser
                355                 360                 365
Phe Leu Arg Pro Ser Trp Asp Leu Val Ser Ala Phe Tyr Ser Leu Pro
    370                 375                 380
Leu Ala Pro Leu Ser Pro Thr Ser Val Pro Ile Ser Pro Val Ser Val
385                 390                 395                 400
Gly Arg Gly Pro Asp Pro Asp Ala His Val Ala Val Asn Leu Ser Arg
                405                 410                 415
Tyr Glu Gly
```